(12) United States Patent
Hanson et al.

(10) Patent No.: US 7,960,420 B2
(45) Date of Patent: Jun. 14, 2011

(54) DIAZONAMIDE ANALOGS WITH IMPROVED SOLUBILITY

(75) Inventors: Gunnar James Hanson, Chapel Hill, NC (US); Qi Wei, Dallas, TX (US); Ming Zhou, Coppell, TX (US)

(73) Assignee: Joyant Pharmaceuticals, Inc, Dallas, TX (US)

( * ) Notice: Subject to any disclaimer, the term of this patent is extended or adjusted under 35 U.S.C. 154(b) by 302 days.

(21) Appl. No.: 12/340,143

(22) Filed: Dec. 19, 2008

(65) Prior Publication Data

US 2009/0163446 A1     Jun. 25, 2009

Related U.S. Application Data

(60) Provisional application No. 61/016,334, filed on Dec. 21, 2007.

(51) Int. Cl.
*C07D 263/30* (2006.01)
*A61K 38/00* (2006.01)

(52) U.S. Cl. ........................ 514/375; 540/457
(58) Field of Classification Search .................. 540/457; 514/375
See application file for complete search history.

(56) References Cited

U.S. PATENT DOCUMENTS

| | | |
|---|---|---|
| 4,261,989 A | 4/1981 | Sasaki et al. |
| 5,387,584 A | 2/1995 | Schnur |
| 5,624,677 A | 4/1997 | El-Rashidy et al. |
| 5,932,566 A | 8/1999 | Schnur et al. |
| 7,022,720 B2 | 4/2006 | Harran et al. |
| 2006/0089397 A1 | 4/2006 | Harran et al. |
| 2007/0149583 A1 | 6/2007 | Harran et al. |
| 2009/0005572 A1 | 1/2009 | Hanson et al. |

FOREIGN PATENT DOCUMENTS

| | | |
|---|---|---|
| WO | WO-02/036075 | 5/2002 |
| WO | WO-03/106438 | 12/2003 |
| WO | WO-2005/028434 | 3/2005 |
| WO | WO-2008/154441 | 12/2008 |

OTHER PUBLICATIONS

Berge et al., J. Pharm. Sci. (1977) 66:1-10.
Cheung et al., Bioorg. Med. Chem. Lett. (2005) 15:3338-3343.
Chiosis et al., ACS Chemical Biology (2006) 1(5):279-284.
Cruz-Monserrate et al., Mol. Pharmacol. (2003) 63:1273-1280.
Hellman, Cancer: Principles and Practice of Oncology (1993) 4$^{th}$ ed. vol. 1 248-275.
Lindquist et al., JACS (1991) 113:2303-2304.
Moulin et al., JACS (2005) 127:6999-7004.
Soga et al., Curr. Cancer Drug Targets (2003) 3:359-369.
Yamamoto et al., Angew. Chem. (2003) 42:1280-1284.
Dabydeen et al. Comparison of the Activities of the Truncated Halichondrin B Analog NSC 707389 (E7389) with Those of the Parent Compound and a Proposed Binding Site on Tubulin, Mol Pharm 70, 1866-75, 2006.
International Search Report and Written Opinion in counterpart PCT/US2008/87783, 2008.

*Primary Examiner* — Bruck Kifle
(74) *Attorney, Agent, or Firm* — Richard Aron Osman

(57) ABSTRACT

Diazonamide A analogs, and the salts, esters and conjugates thereof, having improved aqueous solubility are provided. Also provided are pharmaceutical compositions, and methods for preparing and using such compounds and compositions for the treatment of proliferative diseases.

27 Claims, 2 Drawing Sheets

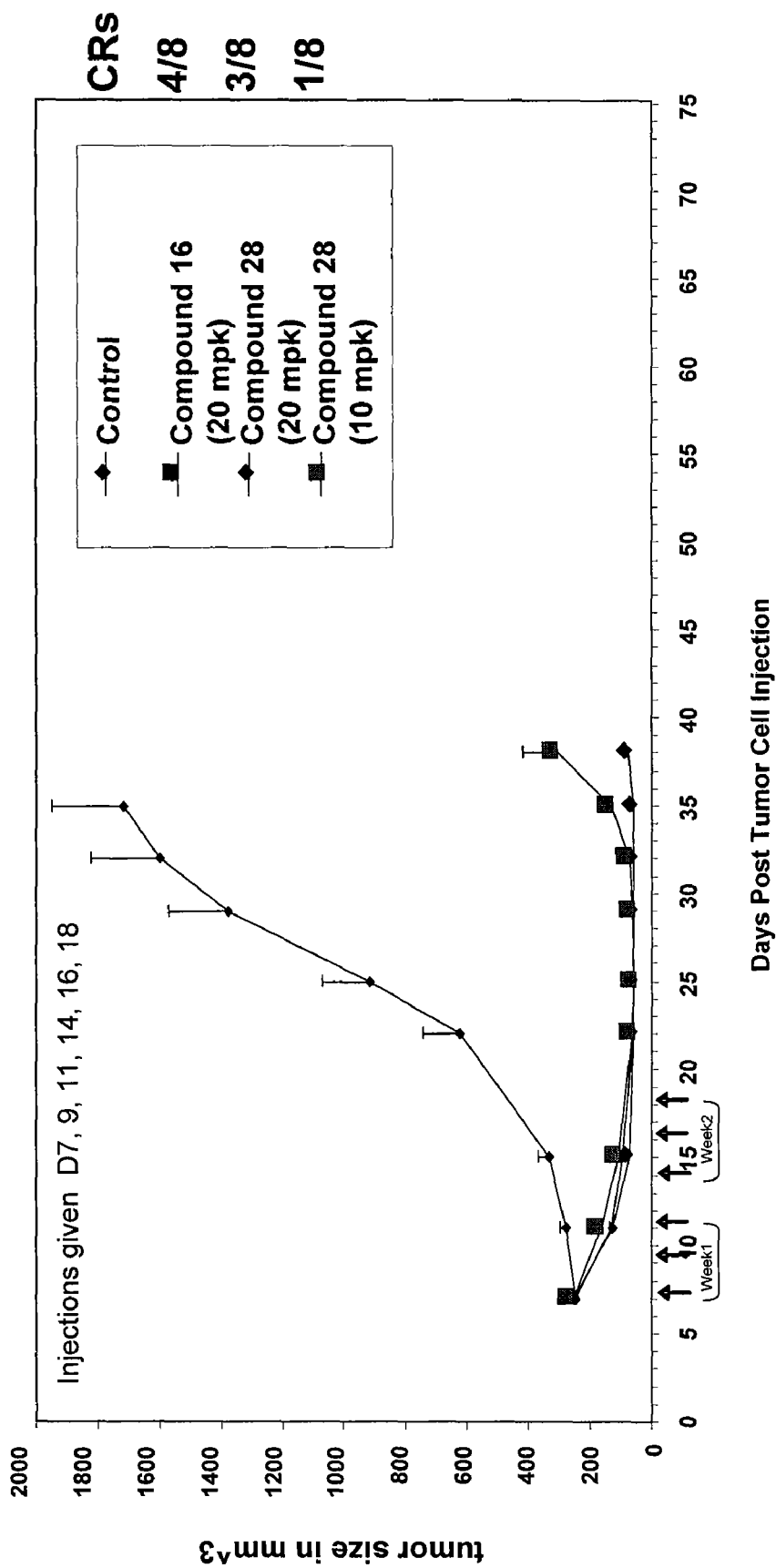

DIAZONAMIDE ANALOGS WITH IMPROVED SOLUBILITY

RELATED APPLICATIONS

This application claims benefit of priority to U.S. Provisional Application Ser. No. 61/016,334 filed 21 Dec. 2007, the contents of which are incorporated herein by reference in their entirety.

TECHNICAL FIELD

The invention relates to analogs of diazonamide A having improved aqueous solubility, and to pharmaceutical compositions thereof. The invention also relates to methods of using such compounds and compositions for the treatment of proliferative diseases. A synthetic route for the preparation of such analogs is also disclosed.

BACKGROUND ART

Diazonamide A is a mitotic spindle-disrupting agent first isolated from the marine organism *Diazona angulata*, having the structure:

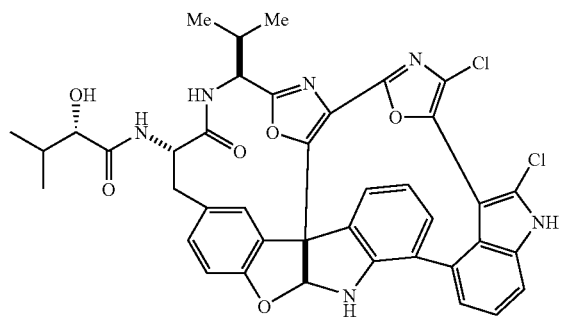

Numerous attempts have been made to synthesize this compound and its analogs. PCT publication WO 03/106438 describes a putative synthetic route; however, the structure identified as diazonamide A provided in that publication is incorrect. U.S. Pat. No. 7,022,720 correctly discloses the structure of diazonamide A and describes the synthesis of some of its analogs through the combined use of catalytic Heck endocyclization, stereo-controlled ring-contracting Pinacol rearrangement, and indole arylation via internal photo-induced electron transfer. Generic structures of some analogs are provided. U.S. application Ser. No. 11/264,502, a continuation-in-part of U.S. Ser. No. 10/227,509 (now U.S. Pat. No. 7,022,720) was filed 31 Oct. 2005, and is published as 2006/0089397. U.S. Ser. No. 11/591,016, a continuation-in-part of U.S. application Ser. No. 11/264,502, was filed 31 Oct. 2006, and is published as U.S. application 2007/0149583.

Diazonamide A demonstrated potent antineoplastic activity. Lindquist et al. *J. Am. Chem. Soc.,* 1991, 113:2303 2304. In HCT-116 cells, a human colorectal carcinoma line, diazonamide A exhibited $GI_{50}$ values (50% growth inhibitory concentration) of less than 15 ng/ml. Diazonamide A has also been found to inhibit microtubule assembly. Cruz-Monserrate et al., *Mol. Pharmacol.,* 2003, 63:1273-1280. An analog of diazonamide A having improved antitumor activity was disclosed in U.S. application 2007/0149583. Thus, diazonamide A and its analogs represent a promising new class of antitumor agents.

Limited aqueous solubility poses difficulties in the formulation and administration of many anticancer agents. In particular, intravenous administration of an anticancer agent with low aqueous solubility may require the infusion of a large volume of liquid in order to achieve a therapeutic dose. Increasing the solubility of anticancer agents has been an important practical objective of many drug development programs. Orally administered compounds can be relatively less soluble than those administered intravenously, but must be soluble enough to be absorbed.

One obstacle to the development of diazonamide A for pharmaceutical use is its relatively low solubility in pharmaceutically acceptable solvents, in particular water. As a result, there is a need for diazonamide analogs having improved solubility which are suitable for pharmaceutical administration. In particular, there is a desire to design diazonamide analogs having improved aqueous solubility as well as antitumor activity.

SUMMARY OF THE INVENTION

The present invention is directed to diazonamide analogs having improved aqueous solubility, and to synthetic intermediates thereof, as well as to methods for the synthesis and use of such compounds in the treatment of cell proliferative diseases and disorders.

In one aspect, the invention provides a compound of Formula I:

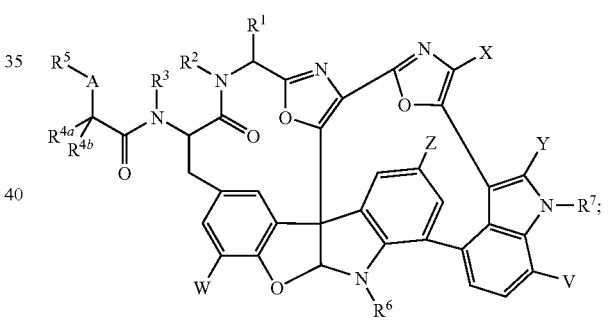

or a pharmaceutically acceptable salt, ester or conjugate thereof;

wherein $R^1$ is H, or C1-C8 alkyl, C2-C8 alkenyl, C2-C8 alkynyl, or a heteroform of one of these, C6-C12 aryl, C7-C20 arylalkyl, C5-C12 heteroaryl, or C6-C20 heteroarylalkyl, each of which may be optionally substituted;

$R^2$ is H or C1-C4 alkyl; or $R^1$ and $R^2$ may be taken together with the atoms to which they are attached to form an optionally substituted 5- to 7-membered azacyclic ring, optionally containing an additional heteroatom selected from N, O and S as a ring member;

$R^3$ is H or C1-C4 alkyl;

each of $R^{4a}$ and $R^{4b}$ is independently H, or C1-C8 alkyl, C2-C8 alkenyl, C2-C8 alkynyl, or a heteroform of one of these, C6-C12 aryl, C7-C20 arylalkyl, C5-C12 heteroaryl, or C5-C20 heteroarylalkyl, each of which may be optionally substituted; or $R^{4a}$ and $R^{4b}$ may be taken together with the carbon to which they are attached to form a C3-C8 cycloalkyl or a C3-C8 heterocyclyl ring, each of which may be optionally substituted;

$R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, alkylsulfonyl, arylsulfonyl, trialkylsilyl, or alkoxycarbonyl, each of which may be optionally substituted;

V is H, halo, or $OR^{10}$, where $R^{10}$ is H, C1-C6 acyl, C6-C12 aroyl, alkylsulfonyl, arylsulfonyl, —$PO_3H_2$, —$SO_3H$, —$C(O)CR^8{}_2NH_2$, —C(O)-L-COOH, or -L-O—$PO_3H_2$;

each of $R^5$ and $R^7$ is independently H, or C1-C8 alkyl, C1-C8 heteroalkyl, C6-C14 arylalkyl, C6-C14 heteroarylalkyl, C1-C6 acyl, C6-C12 aroyl, alkylsulfonyl, arylsulfonyl, trialkylsilyl, or alkoxycarbonyl, each of which may be optionally substituted; or —$PO_3H_2$, —$SO_3H$, —$C(O)CR^8{}_2NH_2$, —C(O)-L-COOH, or -L-O—$PO_3H_2$;

each $R^8$ is independently H or C1-C8 alkyl, C2-C8 alkenyl, C2-C8 alkynyl, or a heteroform of one of these, C6-C12 aryl, C7-C20 arylalkyl, C5-C12 heteroaryl, or C6-C20 heteroarylalkyl, each of which may be optionally substituted; and L is a C1-C4 alkylene or C2-C4 alkenylene linker;

provided at least one of $R^5$, $R^7$ and $R^{10}$ is —$PO_3H_2$, —$SO_3H$, —$C(O)CR^8{}_2NH_2$, —C(O)-L-COOH, or -L-O—$PO_3H_2$;

A is O or NR, where R is hydrogen or C1-4 alkyl;

each of W and Z is independently H, halo, OH or C1-C4 alkoxy; and each of X and Y is independently H, halo, C1-C8 alkyl, C2-C8 alkenyl, C2-C8 alkynyl, C6-C12 aryl, or C5-C12 heteroaryl, each of which may be optionally substituted, or $COOR^9$ or $CONR^9{}_2$, where each $R^9$ is independently H or C1-C4 alkyl.

In another aspect, the invention provides a compound of Formula II:

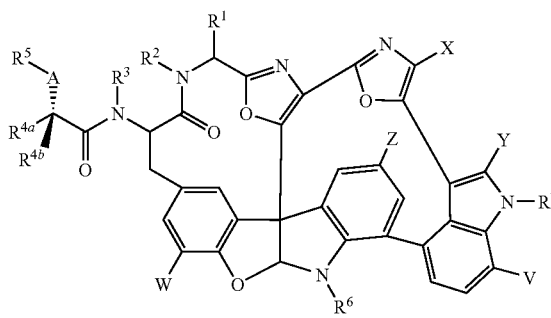

II or a pharmaceutically acceptable salt, ester or conjugate thereof;

wherein $R^1$ is H, or C1-C8 alkyl, C2-C8 alkenyl, C2-C8 alkynyl, or a heteroform of one of these, C6-C12 aryl, C7-C20 arylalkyl, C5-C12 heteroaryl, or C6-C20 heteroarylalkyl, each of which may be optionally substituted;

$R^2$ is H or C1-C4 alkyl; or $R^1$ and $R^2$ may be taken together with the atoms to which they are attached to form an optionally substituted 5- to 7-membered azacyclic ring, optionally containing an additional heteroatom selected from N, O and S as a ring member;

$R^3$ is H or C1-C4 alkyl;

each of $R^{4a}$ and $R^{4b}$ is independently H, or C1-C8 alkyl, C2-C8 alkenyl, C2-C8 alkynyl, or a heteroform of one of these, C6-C12 aryl, C7-C20 arylalkyl, C5-C12 heteroaryl, or C5-C20 heteroarylalkyl, each of which may be optionally substituted; or $R^{4a}$ and $R^{4b}$ may be taken together with the carbon to which they are attached to form a C3-C8 cycloalkyl or a C3-C8 heterocyclyl ring, each of which may be optionally substituted;

$R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, alkylsulfonyl, arylsulfonyl, trialkylsilyl, or alkoxycarbonyl, each of which may be optionally substituted;

V is H, halo, or $OR^{10}$, where $R^{10}$ is H, C1-C6 acyl, C6-C12 aroyl, alkylsulfonyl, arylsulfonyl, —$PO_3H_2$, —$SO_3H$, —$C(O)CR^8{}_2NH_2$, —C(O)-L-COOH, or -L-O—$PO_3H_2$;

each of $R^5$ and $R^7$ is independently H, or C1-C8 alkyl, C1-C8 heteroalkyl, C6-C14 arylalkyl, C6-C14 heteroarylalkyl, C1-C6 acyl, C6-C12 aroyl, alkylsulfonyl, arylsulfonyl, trialkylsilyl, or alkoxycarbonyl, each of which may be optionally substituted; or —$PO_3H_2$, —$SO_3H$, —$C(O)CR^8{}_2NH_2$, —C(O)-L-COOH, or -L-O—$PO_3H_2$;

each $R^8$ is independently H or C1-C8 alkyl, C2-C8 alkenyl, C2-C8 alkynyl, or a heteroform of one of these, C6-C12 aryl, C7-C20 arylalkyl, C5-C12 heteroaryl, or C6-C20 heteroarylalkyl, each of which may be optionally substituted; and L is a C1-C4 alkylene or C2-C4 alkenylene linker;

provided at least one of $R^5$, $R^7$ and $R^{10}$ is —$PO_3H_2$, —$SO_3H$, —$C(O)CR^8{}_2NH_2$, —C(O)-L-COOH, or -L-O—$PO_3H_2$;

A is O or NR, where R is hydrogen or C1-4 alkyl;

each of W and Z is independently H, halo, OH or C1-C4 alkoxy; and each of X and Y is independently H, halo, C1-C8 alkyl, C2-C8 alkenyl, C2-C8 alkynyl, C6-C12 aryl, or C5-C12 heteroaryl, each of which may be optionally substituted, or $COOR^9$ or $CONR^9{}_2$, where each $R^9$ is independently H or C1-C4 alkyl.

In another aspect, the invention provides a compound of Formula III-A or III-B

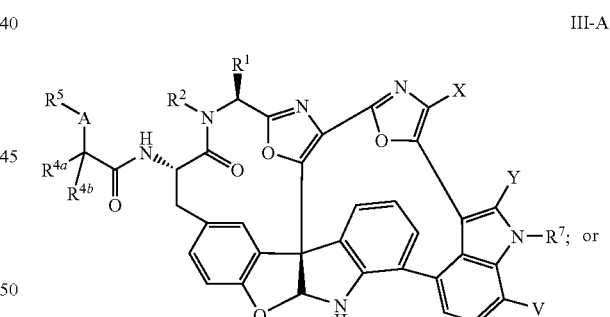

III-A

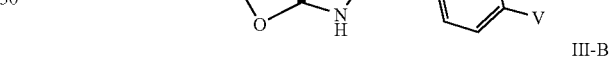

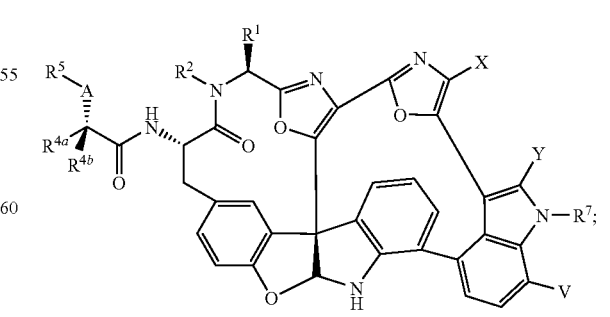

III-B or a pharmaceutically acceptable salt, ester or conjugate thereof;

wherein $R^1$, $R^2$, $R^{4a}$, $R^{4b}$, $R^5$, $R^7$, A, V, X and Y are defined as for Formula I.

In a further aspect, the invention provides a compound of Formula IV-A or IV-B

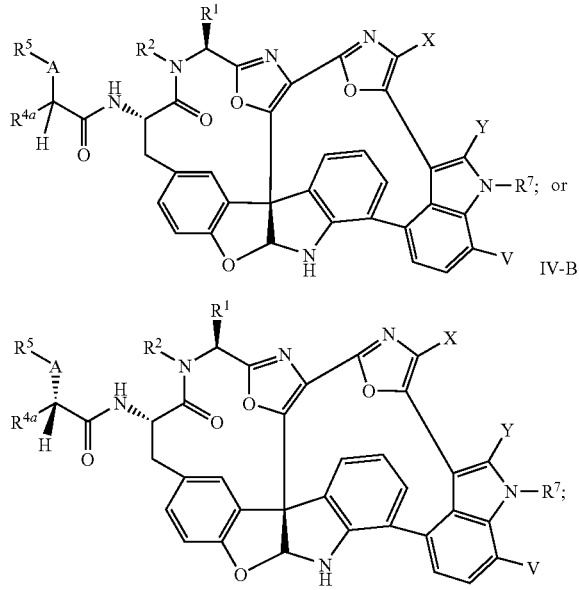

IV-A

IV-B or a pharmaceutically acceptable salt, ester or conjugate thereof;

wherein $R^1$, $R^2$, $R^{4a}$, $R^{4b}$, $R^5$, $R^7$, A, V, X and Y are defined as for Formula I.

In another aspect, the invention provides a compound of Formula V or VI:

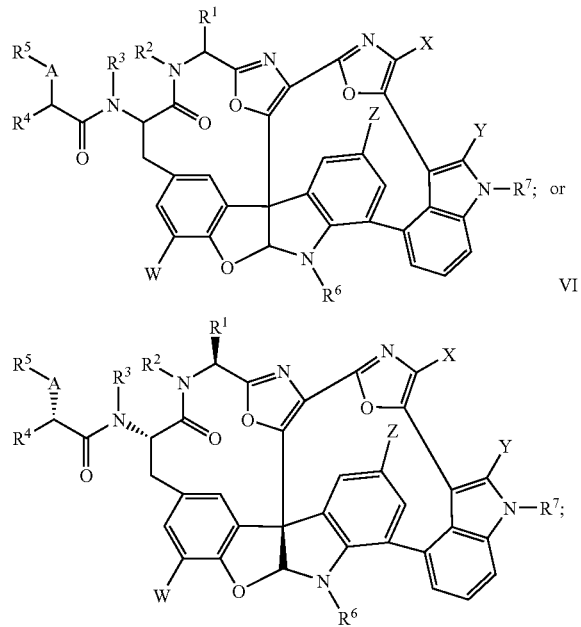

V

VI or a pharmaceutically acceptable salt, ester or conjugate thereof;

wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

$R^2$ is H or C1-C4 alkyl; or $R^1$ and $R^2$ may be taken together with the atoms to which they are attached to form a 5- or 6-membered heterocyclic ring containing one nitrogen atom;

$R^3$ is H or C1-C4 alkyl;

each of $R^5$, $R^6$ and $R^7$ is independently H, or C1-C8 alkyl, C1-C8 heteroalkyl, C6-C14 arylalkyl, C6-C14 heteroarylalkyl, optionally fluorinated C1-C6 acyl, C6-C12 aroyl, alkylsulfonyl, arylsulfonyl, trialkylsilyl, or alkoxycarbonyl, each of which may be optionally substituted; or —$PO_3H_2$, —$SO_3H$, —$C(O)CR^8{}_2NH_2$, or —C(O)-L-COOH;

wherein at least one of $R^5$ and $R^7$ is —$PO_3H_2$, —$SO_3H$, —$C(O)CR^8{}_2NH_2$, or —C(O)-L-COOH;

$R^4$ is H, or C1-C8 alkyl, C2-C8 alkenyl, C2-C8 alkynyl, C5-C6 aryl, C6-C12 arylalkyl, or a heteroform of one of these, each of which may be optionally substituted;

each $R^8$ is independently H or C1-C8 alkyl, C2-C8 alkenyl, C2-C8 alkynyl, C5-C6 aryl, C6-C12 arylalkyl, or a heteroform of one of these, each of which may be optionally substituted;

L is a C1-C4 alkylene or alkenylene linker;

A is O or NR, where R is hydrogen or C1-4 alkyl; and each of W, X, Y and Z is independently H, or halo.

In another aspect, the invention is directed to a pharmaceutical composition comprising at least one compound of Formula I, II, III-A, III-B, IV-A, IV-B, V or VI, and/or a pharmaceutically acceptable salt, ester or conjugate thereof, and at least one pharmaceutically acceptable excipient. In certain embodiments, the pharmaceutical composition may be in unit dosage form.

In another aspect, the invention provides a conjugate of Formula I, II, III-A, III-B, IV-A, IV-B, V or VI coupled to a stabilizing agent or a targeting agent.

In a further aspect, the invention is directed to the use of a compound of Formula I, II, III-A, III-B, IV-A, IV-B, V or VI for the preparation of a medicament, useful for the treatment of proliferative diseases. In certain embodiments, the medicament may be in unit dosage form.

In a further aspect, the invention is directed to a method of treating a cell proliferative disorder, comprising administering to a subject in need thereof a therapeutically effective amount of a compound of the invention, or a pharmaceutically acceptable salt, ester, conjugate, or a pharmaceutical composition thereof, thereby treating the cell proliferative disorder. In certain embodiments, the symptoms and/or the pathology of the disease are inhibited or reduced; for example, tumor growth, tumor size, and/or metastasis may be inhibited and/or decreased. In other embodiments, the recurrence of the disease may be delayed or inhibited, e.g., by increasing the duration of a period of remission in a proliferative disorder such as a cancer. The cell proliferative disorder may be a tumor or a cancer in a human or animal subject. In specific embodiments, the cell proliferative disorder is a paclitaxel-resistant tumor or cancer. In preferred embodiments, the subject is human.

In another aspect, the invention provides a method for reducing cell proliferation and/or inducing cell death in a system, comprising contacting the system with an effective amount of a compound of the invention, or a salt, ester, conjugate, or pharmaceutical composition thereof, thereby reducing cell proliferation and/or inducing cell death (e.g., apoptosis or apoptotic cell death) in the system. The system may be a cell or a tissue. In some embodiments, the system includes a cell from a subject or a cultured cell (e.g., in vitro or ex vivo).

In another aspect, the invention provides a method for ameliorating a cell proliferative disorder, comprising administering to a subject in need thereof a therapeutically effective amount of a compound of the invention, or a pharmaceutically acceptable salt, ester, conjugate, or a pharmaceutical composition thereof, thereby ameliorating the cell proliferative disorder. In some embodiments, cell proliferation may be reduced, and/or cell death, such as apoptosis or apoptotic cell death, may be induced. The cell proliferative disorder may be a tumor or a cancer in a human or animal subject.

The compounds and pharmaceutical compositions described herein may be used alone, or in conjunction with or in combination with an additional therapeutic having anticancer effects in the methods described herein. Such additional therapeutic can be a chemotherapeutic agent, an immunotherapeutic agent, or a radiotherapy or surgical procedure. Where a compound of the invention is utilized in conjunction with or in combination with another therapeutic agent or procedure, the two agents and or/procedures may be co-administered, or they may be administered separately where their administration is timed so the two agents act concurrently or sequentially.

In yet another aspect, the invention is directed to a method to synthesize a compound of the invention, or a pharmaceutically acceptable salt, ester or conjugate thereof, as well as to synthetic intermediates useful for the synthesis of such compounds.

DESCRIPTION OF THE FIGURES

FIG. 2 shows data for compound 28 versus compound 16 in an HCC461 human NSCLC xenograft. Compound 16 was administered at 20 mg/kg per dose, and compound 28 was administered at doses of 10 mg/kg or 20 mg/kg per dose. Injections were given at days 7, 9, 11, 14, 16 and 18 days post tumor cell injection.

MODES OF CARRYING OUT THE INVENTION

Figure 1:
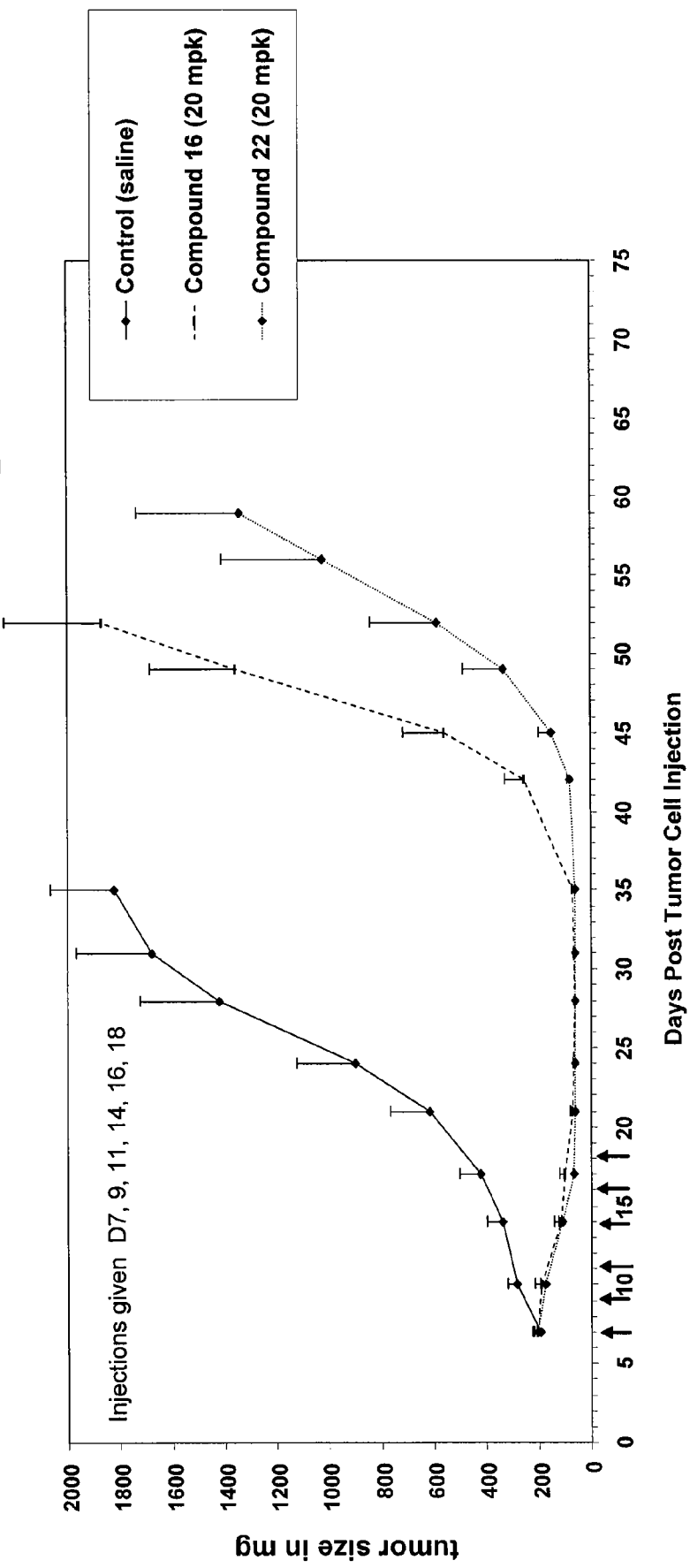
FIG. 1 shows activity of compound 22 versus compound 16 in an HCC461 human NSCLC xenograft. Compounds were administered at 20 mg/kg per dose. Injections were given at days 7, 9, 11, 14, 16 and 18 days post tumor cell injection. No weight loss was observed in the treated group. There were no tumor free animals in either group.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular forms "a", "an", and "the" include plural references unless indicated otherwise.

As used herein, the term "subject" refers to a human or animal subject. In preferred embodiments, the subject is human. In further embodiments, the "subject," is in need of treatment, that is, the subject can be afflicted with, is likely to be afflicted with, or might be afflicted with a disease which is treatable by administration of a compound of the invention, or pharmaceutically acceptable salt, ester, or conjugate thereof, or composition comprising the same.

As used herein, the terms "treat", "treating" or "treatment" refer to inhibiting a disease, condition or disorder in a subject who is experiencing or displaying the symptoms or pathology of the disease, condition or disorder; delaying or inhibiting the recurrence of the disease, condition or disorder, for example, by increasing the duration of a period of remission in a proliferative disorder such as a cancer; or ameliorating the disease, condition or disorder in a subject who is experiencing or displaying the symptoms or pathology of the disease, condition or disorder. Treatment of subject is typically carried out by administration of a compound of the invention to the patient in a therapeutically effective amount. Where specifically indicated, "treatment" may also relate to preventing a disease, condition or disorder in a subject who may be predisposed to the disease, condition or disorder but is not yet experiencing or displaying the symptoms or pathology of the disease, condition or disorder.

As used herein, the phrase "therapeutically effective amount" refers to the amount of active compound or pharmaceutical agent that elicits the biological or medicinal response that is being sought in a tissue, system, animal, or human by a researcher, veterinarian, medical doctor or other clinician, such as prevent or inhibit a particular disease, condition or disorder. The biological or medicinal response, can include, but is not limited to, inhibition of and/or decreased tumor growth, tumor size, metastasis, and the like, and can be readily assessed by a methods known to those of skill in the art, including, e.g., such methods as disclosed herein.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isopropyl, isobutyl, tert-butyl, cyclohexyl, cyclopentylethyl, 2-propenyl, 3-butynyl, and the like. The total number of carbon atoms in each such group is sometimes described herein, e.g., when the group can contain up to ten carbon atoms it may be described as 1-10C or as C1-C10 or as C1-10 or as $C_{1-10}$. When heteroatoms (typically N, O and S) are allowed to replace carbon atoms of an alkyl, alkenyl or alkynyl group, as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described. Alkyl, alkenyl and alkynyl groups may be optionally fluorinated.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-6C (alkyl) or 2-6C (alkenyl or alkynyl), or 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Preferably, each heteroalkyl, heteroalkenyl and heteroalkynyl group contains only 1-2 heteroatoms as part of the skeleton of backbone of the heteroalkyl group, i.e., not including substituents that may be present. Exemplary heteroalkyls include alkoxyls such as O-alkyl, alkyl ethers, secondary and tertiary alkyl amines, alkyl sulfides, and the like.

The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. Where such groups contain N, the nitrogen atom may be present as NH or it may be substituted if the heteroalkyl or similar group is described as optionally substituted. Where such groups contain S, the sulfur atom may optionally be oxidized to SO or $SO_2$ unless otherwise indicated. For reasons of chemical stability, it is also understood that, unless otherwise specified, such groups do not include more than three contiguous heteroatoms as part of the heteroalkyl chain, although an oxo group may be present on N or S as in a nitro or sulfonyl group. Thus —C(O)NH$_2$ can be a C2 heteroalkyl group substituted with =O; and —SO$_2$NH— can be a C2 heteroalkylene, where S replaces one carbon, N replaces one carbon, and S is substituted with two =O groups.

While "alkyl" as used herein includes cycloalkyl and cycloalkylalkyl groups, the term "cycloalkyl" may be used herein to specifically describe a saturated or partially saturated, monocyclic or fused or spiro polycyclic, carbocycle that is connected via a ring carbon atom, and "cycloalkylalkyl" may be used to describe a carbocyclic non-aromatic group that is connected to the base molecule through an alkyl linker. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. The size of a cycloalkylalkyl or heterocyclylalkyl group describes the total number of carbon atoms or of carbon atoms plus heteroatoms that replace carbon atoms of an alkyl, alkenyl, alkynyl, cycloalkyl, or cycloalkylalkyl portion. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, e.g., —C(=O)R where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl. Also included within the definition of heteroacyl groups are thioacyl substituents, e.g., —C(=S)R, and imine groups, e.g., —C(=NH)R.

Acyl and heteroacyl groups are bonded to any group or molecule to which they are attached through the open valence of the carbonyl carbon atom. Typically, they are C1-C8 acyl groups, which include formyl, acetyl, trifluoroacetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group. Acyl groups may be optionally fluorinated.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least one ring has the characteristics of aromaticity, even though it may be fused to a nonaromatic ring. Typically, the aromatic and heteroaromatic ring systems contain 5-12 ring member atoms. Preferably the monocyclic aryl and heteroaryl groups contain 5-6 ring members, and the bicyclic aryl and heteroaryl groups contain 8-10 ring members. In frequent embodiments, aryl groups are C6-C12 and heteroaryl groups are C5-C12.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moieties.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl. Preferably, an arylalkyl group includes one or two optionally substituted phenyl rings and a C1-C4 alkylene that is unsubstituted or is substituted with one or two C1-C4 alkyl groups or C1-C4 heteroalkyl groups, where the alkyl or heteroalkyl groups can optionally cyclize to form a ring such as cyclopropane, dioxolane, or oxacyclopentane, and wherein the alkyl or heteroalkyl groups may be optionally fluorinated. Examples of arylalkyl groups include optionally substituted benzyl, phenylethyl, diphenylmethyl, and triphenylmethyl groups. Optional substituents when present on the aryl ring of an arylalkyl group are the same as those described herein for an aryl ring.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. For example, heteroaryl groups include pyridylmethyl, pyridylethyl, —O-benzyl, and the like. In frequent embodiments, arylalkyl groups are C7-C20 and heteroarylalkyl groups are C6-C20; sometimes they are C7-C12 and C6-C12, respectively.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as —(CH$_2$)$_3$—, i.e., the specified length represents the number of atoms linking the attachment points rather than the total number of atoms in the hydrocarbyl group: —C(Me)$_2$- would thus be a one-atom linker, since the available valences are separated by only one atom. Where an alkylene group is substituted, the substituents include those typically present on alkyl groups as described herein, thus —C(=O)— is an example of a one-carbon substituted alkylene. Where it is described as unsaturated, the alkylene may contain one or more double or triple bonds.

"Heteroalkylene" as used herein is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, —C(=O)NH— is an example of a two-carbon substituted heteroalkylene, where N replaces one carbon, and C is substituted with a =O group.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

Unless otherwise indicated, the term "oxo" refers to =O.

"Halo", as used herein, includes fluoro, chloro, bromo and iodo. Fluoro, chloro, and bromo are often preferred "Amino" as used herein refers to NH$_2$, but where an amino is described as "substituted" or "optionally substituted", the term includes NR$_2$ wherein each R is independently H, or is an alkyl, alkenyl, alkynyl, acyl, aryl, or arylalkyl group or a heteroform of one of these groups, each of which may be optionally substituted with the substituents described herein as suitable for the corresponding type of group. The term also includes forms wherein the two R groups on one nitrogen atom are linked together to form a 3-8 membered monocyclic azacyclic ring or an 8-12 membered bicyclic fused azacyclic ring system, each of which may be saturated, unsaturated or aromatic and which may contain 1-3 heteroatoms independently selected from N, O and S as ring members, and which may be optionally substituted with the substituents described as suitable for alkyl groups or, if NR$_2$ comprises an aromatic group, it may be optionally substituted with the substituents described as typical for heteroaryl groups.

Amino and hydroxyl groups may optionally be in a protected or unprotected form. One of skill in the art would appreciate that appropriate amine and hydroxyl protecting groups may vary depending on the functionality present in the particular molecule and the nature of the group. Suitably protected amines may include, for example, amines protected as carbamates (e.g., tert-butoxycarbonyl (Boc), benzyloxycarbonyl (Cbz), fluorenylmethyloxy-carbonyl (Fmoc), allyloxycarbonyl (Alloc) or (trialkylsilyl)ethoxycarbonyl), carboxamides (e.g., formyl, acetyl, trifluoroacetyl, or benzoyl), sulfonamides, phthalimides, succinimides, Schiff's base derivatives, and the like. Also included are alkyl, allylic and benzylic amines, as well as trialkylsilyl protected amines. Suitable protecting groups for hydroxyl groups may include, for example, trialkylsilyl ethers, tetrahydropyranyl ethers, alkoxyalkyl ethers (such as MEM, MOM, SEM and the like), O-acyl or O-aroyl esters, or the like.

Where an amine or hydroxyl is present in protected form, it is sometimes desirable to remove the protecting group. Thus, the methods of the present invention also optionally include a step of removing any protecting groups present on an amine, aminoalkyl or hydroxyl group.

The terms "alkylsulfonyl" and "arylsulfonyl" as used herein refer to moieties of the form —SO$_2$alkyl or —SO$_2$aryl, where alkyl and aryl are defined as above. Optionally fluorinated C1-C4 alkyl, and optionally substituted phenyl and pyridyl groups are preferred for sulfonyl moieties. The phenyl groups of an arylsulfonyl moiety may be optionally substituted with one or more substituents suitable for an aryl ring; for example, they may be substituted by halo, alkyl, nitro, alkoxy, amino, or the like. Such sulfonyl moieties, when present on oxygen form sulfonates. Such sulfonyl moieties form sulfonamides when present on nitrogen, and sulfones when present on carbon. Representative sulfonates include, e.g., —OSO$_2$Me (mesylate), —OSO$_2$CF$_3$ (triflate), —OSO$_2$tolyl (tosylate), and the like.

The term "alkoxycarbonyl" as used herein refers to a moiety of the form —COOR', where R' is C1-C8 alkyl, C2-C8 alkenyl, C5-C6 aryl or heteroaryl, or C6-C14 arylalkyl, trialkylsilyl, or the like, each of which may be optionally substituted. When present on nitrogen, such alkoxycarbonyl moieties form carbamates, which are frequently used as nitrogen protecting groups. In some such embodiments, R' may be optionally halogenated C1-C4 alkyl (e.g., tert-butyl, methyl, ethyl, 2,2,2-trichloroethyl, 1,1-dimethyl-2,2,2-trichloroethyl), allyl, optionally substituted benzyl, fluorenylmethyl, or trialkylsilyl (e.g., triisopropylsilyl, triethylsilyl, tert-butyldimethylsilyl). When present on carbon, such moieties may also be referred to as carboxylate esters, carboalkoxy groups, or the like.

The term "substituted" means that the specified group or moiety bears one or more non-hydrogen substituents. The term "unsubstituted" means that the specified group bears no such substituents.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

Alkyl, alkenyl and alkynyl groups are often substituted to the extent that such substitution makes sense chemically. Typical substituents include, but are not limited to, halo, OH, =O, =N—CN, =N—OR, =NR, OR, NR$_2$, SR, SOR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, optionally fluorinated C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C12 aryl, C5-C12 heteroaryl, C7-C20 arylalkyl, or C6-C20 heteroarylalkyl, and each R is optionally substituted with one or more groups selected from halo, OH, =O, =N—CN, =N—OR', =NR', OR', NR'$_2$, SR', SOR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, optionally fluorinated C1-C8 alkyl, C2-C8 heteroalkyl, C1-C8 acyl, C2-C8 heteroacyl, C6-C12 aryl, C5-C12 heteroaryl, C7-C20 arylalkyl, or C6-C20 heteroarylalkyl. Alkyl, alkenyl and alkynyl groups can also be substituted by C1-C8 acyl, C2-C8 heteroacyl, C5-C12 aryl or C5-C12 heteroaryl, each of which can be substituted by the substituents that are appropriate for the particular group. Preferred substituents when present on an alkyl, alkenyl or alkynyl group, or a heteroform of one of these, include halo, OH, =O, OR, SR, and NR$_2$, where R is defined as above, preferably where each R is independently H, optionally fluorinated C1-C4 alkyl, or optionally fluorinated C1-C4 acyl.

Aryl and heteroaryl moieties may be substituted with a variety of substituents including optionally fluorinated C1-C8 alkyl, C2-C8 alkenyl, C2-C8 alkynyl, C5-C12 aryl, C1-C8 acyl, C5-20 arylalkyl, and heteroforms of these, each of which can itself be further substituted; other substituents for aryl and heteroaryl moieties include halo, OH, OR, NR$_2$, SR, SOR, SO$_2$R, SO$_2$NR$_2$, NRSO$_2$R, NRCONR$_2$, NRCOOR, NRCOR, CN, COOR, CONR$_2$, OOCR, C(O)R, and NO$_2$, wherein each R is independently H, optionally fluorinated C1-C8 alkyl, C2-C8 heteroalkyl, C2-C8 alkenyl, C2-C8 heteroalkenyl, C2-C8 alkynyl, C2-C8 heteroalkynyl, C6-C12 aryl, C5-C12 heteroaryl, C7-C20 arylalkyl, or C6-C20 heteroarylalkyl, and each R is optionally substituted as described above for alkyl groups. The substituent groups on an aryl or heteroaryl group may of course be further substituted with the groups described herein as suitable for each type of group that comprises the substituent. Preferred substituents when present on an aryl or heteroaryl group include halo, OH, OR, SR, NR$_2$, CN, COOR, CONR$_2$, and NO$_2$, where R is defined as above, preferably where each R is independently H, optionally fluorinated C1-C4 alkyl, or optionally fluorinated C1-C4 acyl.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

The present invention relates generally to a compound of Formula I, II, III-A, III-B, IV-A, IV-B, V or VI (sometimes referred to collectively herein as compounds of the invention), which have enhanced properties in terms of aqueous solubility, comprising a diazonamide analog which contains a suitable water-solubilizing moiety. Non-limiting examples of suitable water-solubilizing moieties include, e.g., a phosphate monoester (—OPO$_3$H$_2$), phosphoric acid amide (—NRPO$_3$H$_2$), an O-sulfate (—OSO$_3$H), an N-sulfate (—NRSO$_3$H), an ester or amide of an alpha-amino acid (e.g., —OC(O)CR$^8$$_2$NH$_2$ or —NRC(O)CR$^8$$_2$NH$_2$), a hemi-ester or hemi-amide of a dicarboxylic acid (e.g., —OC(O)-L-COOH or —NRC(O)-L-COOH, where L is a suitable linker), a heteroalkyl-linked phosphate monoester (e.g., —O-L-OPO$_3$H$_2$ or —NR-L-OPO$_3$H$_2$, where L is a suitable linker), or an ester or salt form of one of these.

Compounds of the invention wherein the water-solubilizing moiety comprises an ester or amide of an alpha-amino acid can be prepared, for example, by reaction of a free hydroxyl or amino group on the diazonamide core with a suitably amine-protected alpha-amino acid under standard acylation or amidation conditions, which are known to one of skill in the art. For example, esterification can be accomplished by reaction of a free hydroxyl with an activated ester of the protected amino acid, whereas amide bond formation can be accomplished using standard peptide coupling techniques. Suitable amino acids include naturally occurring amino acids, as well as amino acids containing unnatural sidechains. Such amino acids may be of either the D- or L-configuration, or may comprise a racemic mixture of isomers or a mixture of isomers containing any degree of chiral purity.

Compounds of the invention wherein the water-solubilizing moiety comprises a hemi-ester or a hemi-acid can be prepared, for example, by reaction of a hydroxyl or amino group on the diazonamide core with a suitably protected diacid, or an activated ester, acid halide, anhydride, or a mixed anhydride thereof, or through other routes which are well known to one of skill in the art. Dicarboxylic acids suitable for the formation of hemi-esters and hemi-amides include, for example, succinic acid, fumaric acid, maleic acid, and other similar dicarboxylic acids.

Compounds of the invention wherein the water-solubilizing moiety comprises a phosphate monoester or phosphoric acid amide can be prepared, for example, by reaction of a hydroxyl or amino group on the diazonamide core with a suitably protected dialkylphosphoryl chloride reagent or other phosphorylating agent as known to those of skill in the art. Alternatively, the phosphate group can be incorporated by reacting a hydroxyl or amino group on the diazonamide core with a precursor molecule in which the phosphate moiety, preferably in a masked form, has already been incorporated.

Compounds of the invention wherein the water-solubilizing moiety comprises a heteroalkyl-linked phosphate monoester can be prepared, for example, by alkylation of a hydroxyl or amino group on the diazonamide core with an alkylating agent, which may contain a suitably protected phosphate group (e.g., halo-(CH$_2$)$_n$—OP(O)(OBn)$_2$) or may contain a functional group, such as a protected or free hydroxyl group, which can be converted to a phosphate moiety (e.g., LG-(CH$_2$)$_n$—OH or LG-(CH$_2$)$_n$—O-PG, where LG represents a leaving group such as halo, alkylsulfonate, and the like, and PG is a removable protecting group).

For water-solubilizing moieties containing an acidic functionality, such as a phosphate monoester (including heteroalkyl-linked), phosphoric acid amide, O-sulfate, N-sulfate or a dicarboxylate hemi-ester or hemi-amide, the alkali or alkaline earth metal salt forms are particularly well suited. Depending on the particular water-solubilizing moiety selected and the pH of the solution, it will be understood that the water-solubilizing group may be in the form of a mono-metal salt or a di-metal salt. For example, the sodium salt of a phosphate monoester may be in the form of a mono-sodium salt (i.e., —OPO$_3$H$^-$.Na$^+$) or a di-sodium salt (i.e., —OPO$_3$$^{-2}$.2Na$^+$). In some embodiments, the acidic functionality may be present in a suitably protected form, such as an ester. For example, a phosphate monoester solubilizing group (—OPO$_3$H$_2$) may be esterified on one of both of the free hydroxyl groups, to provide an esterified group having the form —OP(O)(OR)(OH) or —OP(O)(OR)(OR'). Similar protection strategies may be employed for phosphoric acid amides and N- and O-sulfates, while free carboxylic acids can be protected as carboxylate esters. Protecting groups may be required to facilitate chemical synthesis or purification. In some embodiments, the protected form may be administered and may act as a prodrug. In other embodiments, some or all protecting groups may be removed prior to administration.

Compounds of the invention wherein the water-solubilizing moiety contains a basic functionality, such as an alpha-amino acid derived ester or amide, can be administered in the form of a free base, or as a pharmaceutically acceptable salt, or as a mixture of the depicted form and a corresponding salt form. In some embodiments, the pharmaceutically acceptable salt may be present in the form of a hydrate. Suitable salts include those of inorganic acids such as hydrochlorides, hydrobromides, sulfates, hydrosulfates, and the like, or organic acid addition salts such as the acetates, formates, maleates, and the like. Pharmaceutically acceptable salts are known in the art. See, e.g., Berge et al., *J. Pharm. Sci.* 2006, 66:1-10. In certain embodiments, the basic functionality may be masked, for instance by incorporation of a suitable protecting group on the amine of an alpha-amino acid derived ester or amide. Protection may be required to facilitate synthesis or purification, and in some embodiments, the protected form may be administered and may act as a prodrug.

Compounds of the present invention demonstrate increased aqueous solubility relative to compounds which lack the water-solubilizing moiety. In frequent embodiments, compounds of the invention demonstrate aqueous solubility of from about 0.5 mg/mL to about 20 mg/mL; sometimes, from about 1 mg/mL to about 10 mg/mL; sometimes from about 2 mg/mL to about 7 mg/mL. The aqueous solubility can be about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, or about 5 mg/mL or greater. In some embodiments, compounds of the invention demonstrate aqueous solubility of greater than 1 mg/mL, greater than 2 mg/mL, greater than 2.5 mg/mL, greater than 3 mg/mL, greater than 3.5 mg/mL, greater than 4 mg/mL, greater than 4.5 mg/mL, and preferably greater than 5 mg/mL, greater than 7.5 mg/mL, greater than 10 mg/mL, greater than 15 mg/mL, or greater than 20 mg/mL.

Unless otherwise indicated, the solubility measurements described herein are determined by dissolving the test compound in de-ionized (DI) water at 25° C. All compounds indicated herein to be water soluble have a solubility of greater than 1 mg/mL under these conditions. In particular, the compounds provided by Examples 22, 23, 28, 30, 31, 37 and 38 are water soluble.

Without wishing to be bound by theory, it is envisioned that in certain embodiments, compounds of the invention may function as water soluble prodrugs, wherein the water-solubilizing group can function as a prodrug moiety that is subsequently cleaved in vivo. In such instances, the diazonamide portion of the molecule may be released from the pro-moiety via hydrolytic, oxidative, and/or enzymatic release mechanisms. In other embodiments, certain compounds of the invention may demonstrate biological activity in their own right.

In compounds of Formula I, $R^1$ is H, or C1-C8 alkyl, C2-C8 alkenyl, C2-C8 alkynyl, or a heteroform of one of these, C6-C12 aryl, C7-C20 arylalkyl, C5-C12 heteroaryl, or C6-C20 heteroarylalkyl, each of which may be optionally substituted. In frequent embodiments, $R^1$ is a group selected from the group of α-sidechains found in naturally occurring amino acids. In some embodiments of Formula I, $R^1$ is a C1-C4 alkyl group. In some such embodiments, $R^1$ is methyl, ethyl, propyl, isopropyl, allyl, propargyl, n-butyl, sec-butyl, isobutyl, or tert-butyl. In certain preferred embodiments, $R^1$ is isopropyl.

In other embodiments of Formula I, each of $R^2$ and $R^3$ is independently H or a C1-C4 alkyl group. In certain preferred embodiments, each of $R^2$ and $R^3$ is independently H or Me. In particularly preferred embodiments, both $R^2$ and $R^3$ are H.

In other embodiments of Formula I, $R^1$ and $R^2$ are taken together to form an optionally substituted 5- to 7-membered azacyclic ring. In some embodiments, the azacyclic ring contains an additional heteroatom selected from N, O, and S. In specific embodiments, $R^1$ and $R^2$ are taken together to form an optionally substituted pyrrolidine, piperidine, piperazine, morpholine, thiomorpholine, homopiperidine, or homopiperazine ring. In a preferred embodiment, $R^1$ and $R^2$ are taken together to form a pyrrolidine ring. In another preferred embodiment, $R^1$ and $R^2$ are taken together to form a piperidine ring.

In certain embodiments of Formula I, each of $R^{4a}$ and $R^{4b}$ is independently H, or C1-C8 alkyl, C2-C8 alkenyl, C2-C8 alkynyl, or a heteroform of one of these, C6-C12 aryl, C7-C20 arylalkyl, C5-C12 heteroaryl, or C5-C20 heteroarylalkyl, each of which may be optionally substituted.

In some embodiments, $R^{4a}$ and $R^{4b}$ are the same. In other embodiments, $R^{4a}$ and $R^{4b}$ are different. In some embodiments, at least one of $R^{4a}$ and $R^{4b}$ is H. In other embodiments, at least one of $R^{4a}$ and $R^{4b}$ is a C1-C4 alkyl group. In certain embodiments, one of $R^{4a}$ and $R^{4b}$ is a C1-C4 alkyl group and the other is H. In some such embodiments, $R^{4a}$ is a C1-C4 alkyl group and $R^{4b}$ is H. In certain preferred embodiments, $R^{4a}$ is isopropyl and $R^{4b}$ is H.

In other embodiments, each of $R^{4a}$ and $R^{4b}$ is a C1-C4 alkyl group. In some such embodiments $R^{4a}$ and $R^{4b}$ are the same. In certain preferred embodiments, $R^{4a}$ and $R^{4b}$ are the same, and each of $R^{4a}$ and $R^{4b}$ is ethyl or methyl.

In further embodiments, $R^{4a}$ and $R^{4b}$ may be taken together with the carbon to which they are attached to form a C3-C8 cycloalkyl or a C3-C8 heterocyclyl ring, each of which may be optionally substituted. In some such embodiments, $R^{4a}$ and $R^{4b}$ are taken together to form an optionally substituted cyclopentane or cyclohexane ring. In specific embodiments, $R^{4a}$ and $R^{4b}$ are taken together to form an unsubstituted cyclopentane or cyclohexane ring (i.e., a ring that contains no additional substitution on the alkylene bridging the positions labeled as $R^{4a}$ and $R^{4b}$).

In compounds of Formula I, $R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, alkylsulfonyl, arylsulfonyl, trialkylsilyl, or alkoxycarbonyl, each of which may be optionally substituted. In some embodiments, $R^6$ is a removable protecting group, such as an acyl, aroyl, alkyl- or arylsulfonyl, trialkylsilyl, or alkoxycarbonyl group, as known to those of skill in the art.

V in compounds of Formula I is H, halo, or $OR^{10}$, where $R^{10}$ is H, C1-C6 acyl, C6-C12 aroyl, alkylsulfonyl, arylsulfonyl, $-PO_3H_2$, $-SO_3H$, $-C(O)CR^8{}_2NH_2$, $-C(O)$-L-COOH, or -L-O—$PO_3H_2$. In some embodiments, V is H. In other embodiments, V is $OR^{10}$, where $R^{10}$ is H or acetyl. In certain embodiments, V is $OR^{10}$, where $R^{10}$ is $-PO_3H_2$, $-SO_3H$, $-C(O)CR^8{}_2NH_2$, $-C(O)$-L-COOH, or -L-O—$PO_3H_2$, or a salt or ester form thereof. In a specific embodiment, V is OR where $R^{10}$ is $-PO_3H_2$, or a salt or ester form thereof.

In compounds of Formula I, each of $R^5$ and $R^7$ is independently H, or C1-C8 alkyl, C1-C8 heteroalkyl, C6-C14 arylalkyl, C6-C14 heteroarylalkyl, C1-C6 acyl, C6-C12 aroyl, alkylsulfonyl, arylsulfonyl, trialkylsilyl, or alkoxycarbonyl, each of which may be optionally substituted; or $-PO_3H_2$, $-SO_3H$, $-C(O)CR^8{}_2NH_2$, $-C(O)$-L-COOH, or -L-O—$PO_3H_2$.

Each $R^8$ is independently H or C1-C8 alkyl, C2-C8 alkenyl, C2-C8 alkynyl, or a heteroform of one of these, C6-C12 aryl, C7-C20 arylalkyl, C5-C12 heteroaryl, or C6-C20 heteroarylalkyl, each of which may be optionally substituted. In some embodiments, at least one $R^8$ is H, and the other $R^8$ is an optionally substituted alkyl, aryl, arylalkyl or heteroarylalkyl group selected from the group of sidechains present in naturally occurring amino acids.

In some embodiments, L is a C1-C4 alkylene or C2-C4 alkenylene linker. In certain embodiments, at least one of $R^5$ and $R^7$ is —C(O)-L-COOH. In some such embodiments, L is an ethylene or ethenylene linker (i.e., —CH$_2$CH$_2$— or —CH=CH—). In other embodiments, at least one of $R^5$ and $R^7$ is -L-O—PO$_3$H$_2$. In some such embodiments, L is a methylene linker (i.e., —CH$_2$—).

In compounds of formula I, at least one of $R^5$, $R^7$ and $R^{10}$ is a water-solubilizing group selected from —PO$_3$H$_2$, —SO$_3$H, —C(O)CR$^8_2$NH$_2$, —C(O)-L-COOH, or -L-O—PO$_3$H$_2$, or a salt or ester form thereof.

In frequent embodiments, the water-solubilizing group is present in salt form. In some such embodiments, the water-solubilizing group comprises an acidic moiety which is present in the form of an alkali or alkaline earth salt. In some such embodiments, the water-solubilizing group comprises a phosphate monoester, which is present in the form of a mono-metal salt or a di-metal salt; sometimes, it is the mono-sodium salt or di-sodium salt. In other embodiments, the water-solubilizing group comprises a basic moiety, and is present in the form of an organic or inorganic acid addition salt. In other embodiments, the water-solubilizing group comprises an acidic moiety which is present in the form of an ester.

In certain embodiments of Formula I, A is O or NR, where R is H or C1-C4 alkyl. In some embodiments, A is O. In some such embodiments, $R^5$ is —PO$_3$H$_2$, —SO$_3$H, —C(O)CR$^8_2$NH$_2$, —C(O)-L-COOH, or -L-O—PO$_3$H$_2$ or a salt or ester form thereof. In other embodiments, A is O and $R^5$ is H, optionally fluorinated C1-C4 alkyl, or optionally fluorinated C1-C4 acyl.

In other embodiments, A is NR, where R is H or C1-C4 alkyl; sometimes A is NH, or NMe. In some such embodiments, $R^5$ is —PO$_3$H$_2$, —SO$_3$H, —C(O)CR$^8_2$NH$_2$, —C(O)-L-COOH, or -L-O—PO$_3$H$_2$ or a salt or ester form thereof. In other embodiments, A is NR and $R^5$ is H, optionally fluorinated C1-C4 alkyl, or optionally fluorinated C1-C4 acyl.

In compounds of Formula I, each of W and Z is independently H, halo, OH or C1-C4 alkoxy group. In certain embodiments, each of W and Z is H; in other embodiments, W is H and Z is halo, preferably chloro.

In compounds of Formula I, each of X and Y is independently H, halo, C1-C8 alkyl, C2-C8 alkenyl, C2-C8 alkynyl, C6-C12 aryl, or C5-C12 heteroaryl, each of which may be optionally substituted, or COOR$^9$ or CONR$^9_2$, where each R$^9$ is independently H or C1-C4 alkyl.

In some embodiments, at least one of X and Y is halo; sometimes, at least one of X and Y is chloro. In certain embodiments, each of X and Y is halo; sometimes, each of X and Y is chloro. In other embodiments, each of X and Y is H. In some embodiments of Formula I, at least one of X and Y is COOR$^9$ or CONR$^9_2$, where each R$^9$ is independently H or C1-C4 alkyl. In some such embodiments, X is COOH or COOMe.

In a preferred embodiment of Formula I, each of W, X, Y and Z is H. In another preferred embodiment, each of W and Z is H, and each of X and Y is chloro. In another preferred embodiment, each of X, Y and Z is chloro, and W is H.

In certain preferred embodiments of Formula I, -A-R$^5$ is —OPO$_3$H$_2$, optionally in the form of a mono- or di-sodium salt. In some such embodiments, -A-R$^5$ is —OPO$_3$H$_2$, and the compound is in the form of a mono-sodium salt (i.e., —OPO$_3$H$^-$.Na$^+$).

In other preferred embodiments of Formula I, $R^7$ is —PO$_3$H$_2$, optionally in the form of a mono- or di-sodium salt. In some such embodiments, -A-R$^5$ is OH; in other such embodiments, -A-R$^5$ is —OPO$_3$H$_2$, optionally in the form of a mono- or di-sodium salt.

In another preferred embodiment, V is OR$^{10}$, where R$^{10}$ is —PO$_3$H$_2$, or a mono- or di-sodium salt thereof.

In further preferred embodiments, $R^7$ is —CH$_2$—OPO$_3$H$_2$, optionally in the form of a mono- or di-sodium salt. In another preferred embodiment, $R^5$ is —CH$_2$—OPO$_3$H$_2$, optionally in the form of a mono- or di-sodium salt.

The same groups described herein for substituent groups $R^1$, $R^2$, $R^3$, $R^{4a}$, $R^{4b}$, $R^5$, $R^6$, $R^7$, $R^8$, $R^9$, $R^{10}$, A, L, V, W, X, Y, and Z in compounds of Formula I are also suitable for the corresponding substituent groups where present in compounds of Formula II, III-A, III-V, IV-A and IV-B. In particular, the preferred embodiments of Formula I are also preferred embodiments of Formula II, III-A, III-V, IV-A and IV-B.

In certain particularly preferred embodiments, the compound is a compound of the formula:

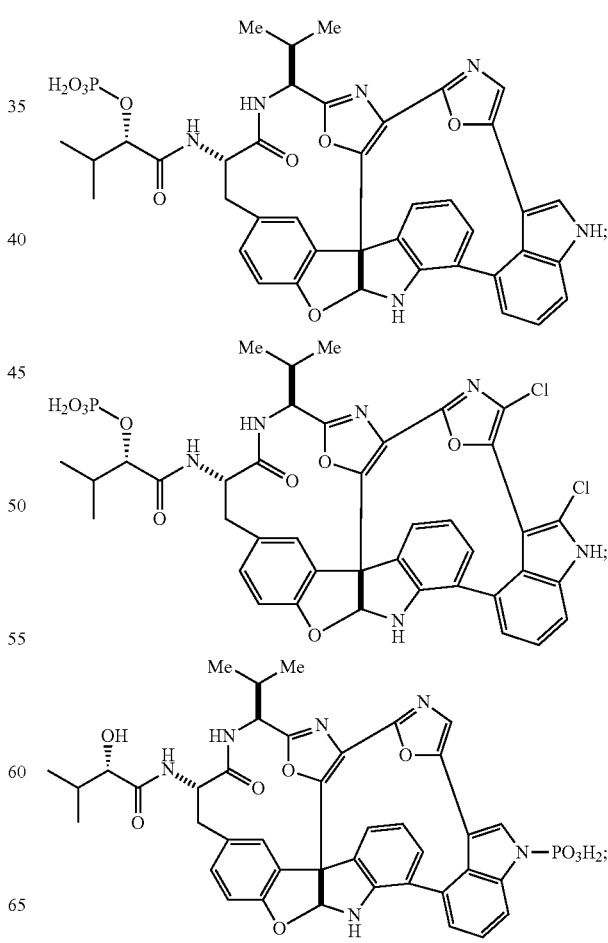

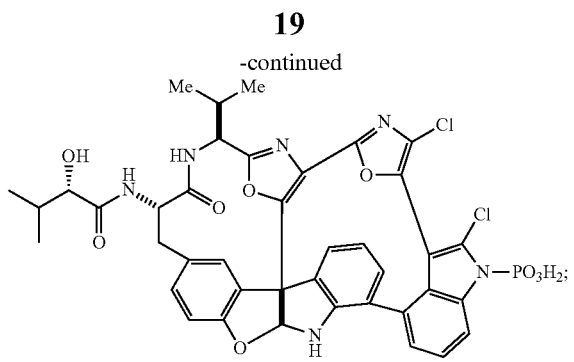
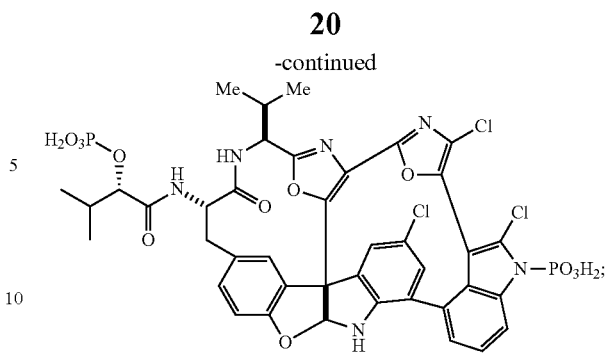
or a pharmaceutically acceptable salt, ester or conjugate thereof.
In other particularly preferred embodiments, the compound is a compound of the formula:
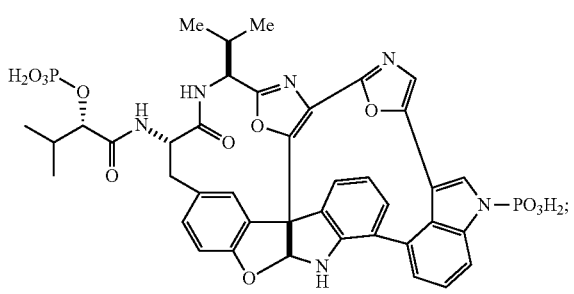
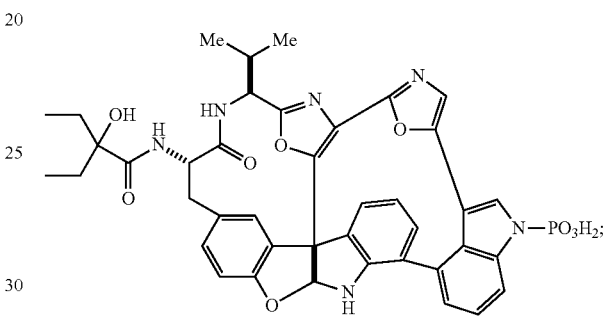
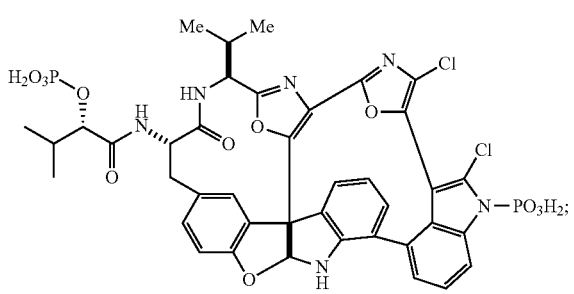
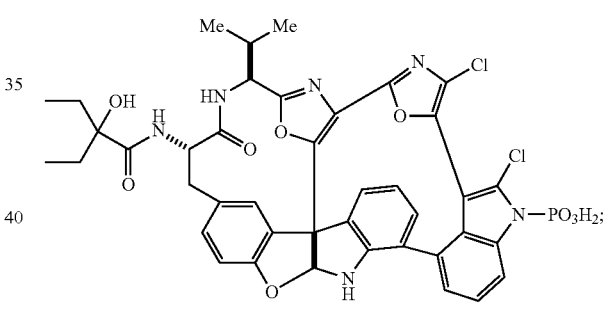
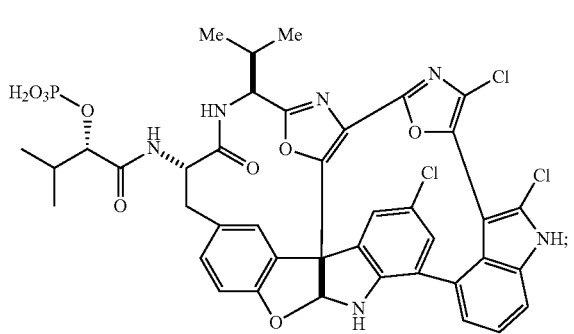
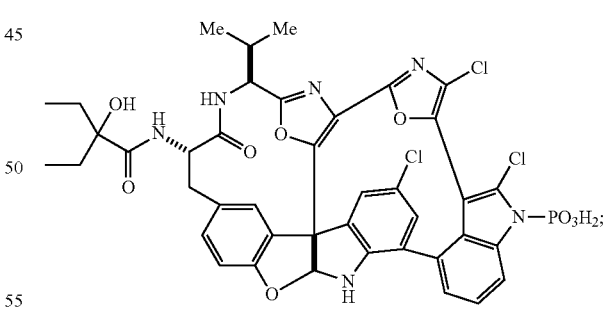
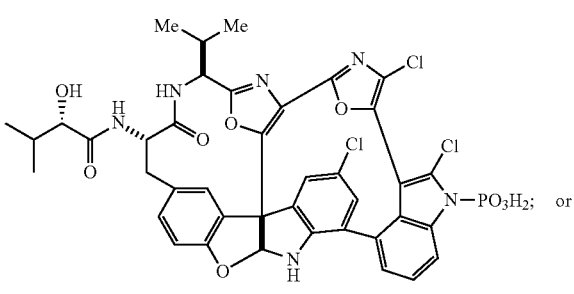
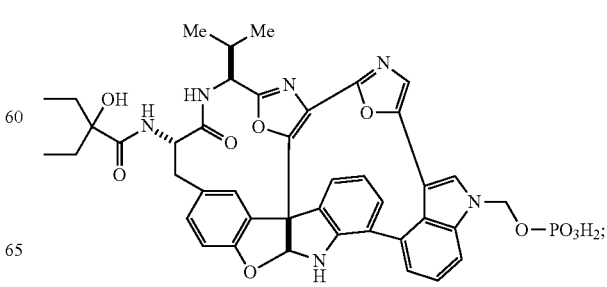

21
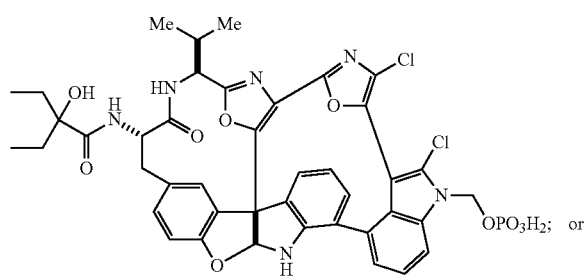
22
or a pharmaceutically acceptable salt, ester or conjugate thereof.
In other particularly preferred embodiments, the compound is selected from:
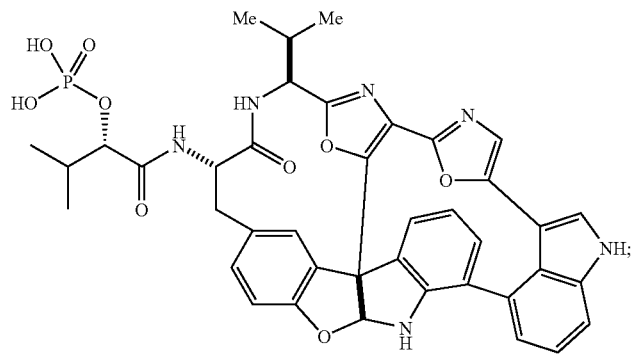
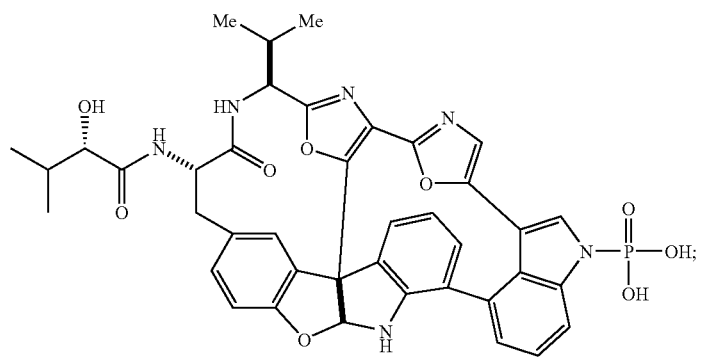
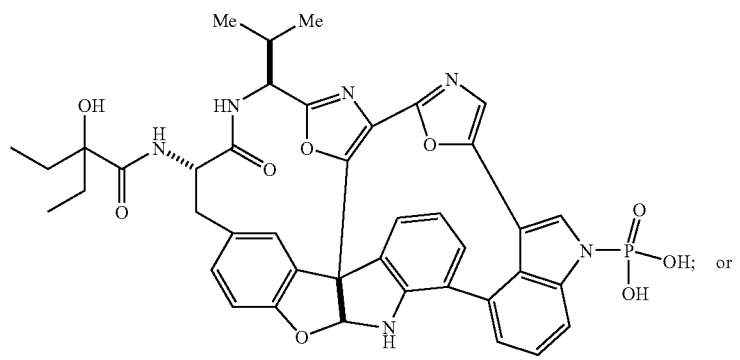

-continued

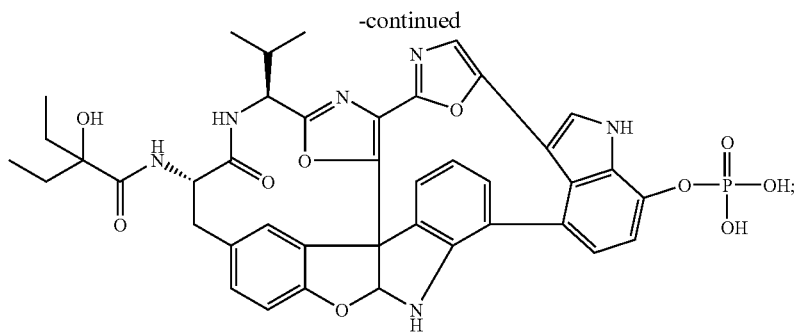

or a pharmaceutically acceptable salt, ester or conjugate thereof.

It will be understood that the features of embodiments described herein may occur in combination with each other. In particular, where certain features are described herein as preferred embodiments, a person of skill in the art will understand that compounds of the invention having combinations of the features specifically described as preferred are also preferred embodiments of the present invention.

The compounds of the invention typically contain one or more chiral centers. The invention expressly includes each diastereomer, as well as each enantiomer of each diastereomer of the compounds described and mixtures thereof, particularly racemic mixtures of single diastereomers such as the ones described, and highly enriched enantiomers having an enantiomeric excess (e.e.) of greater than 90% or greater than about 95%. Substituent groups may also include one or more chiral centers, and each enantiomer and diastereomer of these substituents as well as mixtures thereof are all included within the scope of the invention. Similarly, where double bonds are present, the compounds can exist in some cases as either cis or trans isomers; the invention includes each isomer individually as well as mixtures of isomers.

The compounds of the invention may be isolated as salts where an ionizable group such as a basic amine or a carboxylic acid is present. The invention includes the salts of these compounds that have pharmaceutically acceptable counterions. Such salts are well known in the art, and include, for example, salts of acidic groups formed by reaction with organic or inorganic bases, and salts of basic groups formed by reaction with organic or inorganic acids, as long as the counterions introduced by the reaction are acceptable for pharmaceutical uses. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc.

Examples of organic bases that could be used include trimethylamine, triethylamine, pyridine, picoline, ethanolamine, diethanolamine, triethanolamine, dicyclohexylamine, N,N'-dibenzylethylenediamine, etc. Examples of inorganic acids that could be used include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

In addition, compounds of the invention may be coupled to moieties such as targeting agents. Among such targeting agents are antibodies or immunologically active fragments thereof, including single-chain antibody forms directed against tumor antigens or against receptors or integrins associated with tumors, peptidomimetics directed against these moieties, and the like.

Compounds of the invention may also be coupled to an excipient such as polyethylene glycol (PEG) for altering pharmacokinetics. The selected PEG may be of any convenient molecular weight, and may be linear or branched, and may be optionally conjugated through a linker. The average molecular weight of PEG will preferably range from about 2 kiloDalton (kDa) to about 100 kDa, more preferably from about 5 kDa to about 40 kDa.

The formulations useful in the invention include standard formulations such as those set forth in *Remington's Pharmaceutical Sciences*, latest edition, Mack Publishing Co., Easton, Pa., incorporated herein by reference. Such formulations include those designed for oral delivery, slow release, topical administration, parenteral administration, or any other suitable route as determined by an attending physician or veterinarian. Thus administration may be systemic or local. Suitable vehicles or excipients include liposomes, micelles, nanoparticles, polymeric matrices, buffers, and the full range of formulations known to practitioners. In particular, compounds of the invention are suitable for intravenous administration, owing to their improved water solubility.

Compounds of the invention are useful in treating cell proliferative diseases, in particular, cancer. In some embodiments, the cancer is selected from breast cancer, ovarian cancer, lung cancer, colon cancer, rectal cancer, prostate cancer, pancreatic cancer, melanoma, or glioma.

Compounds of the invention may be used alone, or in conjunction with or in combination with surgical, radiation, chemotherapeutic, immunotherapy, and bone marrow and/or stem cell transplantation methods, or with other palliative agents, such as compounds that aid in nutrition or general health, anti-emetic agents, and the like.

Where an additional chemotherapeutic drug is administered, it is typically one known to have cytostatic, cytotoxic or antineoplastic activity. These agents include, without limitation, antimetabolites (e.g., cytarabine, fludaragine, 5-fluoro-2'-deoxyuridine, gemcitabine, hydroxyurea, methotrexate); DNA active agents (e.g., bleomycin, chlorambucil, cisplatin, cyclophosphamide); intercalating agents (e.g., adriamycin and mitoxantrone); protein synthesis inhibitors (e.g., L-asparaginase, cycloheximide, puromycin); topoisomerase type I inhibitors (e.g., camptothecin, topotecan or irinotecan); topoisomerase type II inhibitors (e.g. etoposide, teniposide anthraquinones, anthracyclines and podophyllotoxin); microtubule inhibitors (e.g., taxanes, such as paclitaxel and docetaxel, colcemid, colchicines, or vinca alkaloids, such as vinblastine and vincristine); kinase inhibitors (e.g. flavopiridol, staurosporin and hydroxystaurosporine), drugs that affect Hsp90 (e.g. geldanomycin and geldanomycin derivatives, radicicol, purine derivatives and antibodies or antibody fragments that selectively bind to Hsp90), TRAIL, a TRAIL receptor antibody, TNF-α or TNF-β, and/or radiation therapy.

In some preferred embodiments, the additional cancer therapeutic agent is TRAIL, a TRAIL receptor antibody, TNF-α or TNF-β. In other preferred embodiments, the additional drugs for co-administration with the compounds of the invention affects Hsp90 (heat-shock protein 90).

Suitable Hsp90 inhibitors include ansamycin derivatives such as geldanomycin and geldanomycin derivatives including 17-(allylamino)-17-desmethoxygeldanamycin (17-AAG), its dihydro derivative, 17-AAGH$_2$, and 17-amino derivatives of geldanomycin such as 17-dimethylaminoethylamino-17-demethoxy-geldanamycin (17-DMAG), 11-oxogeldanamycin, and 5,6-dihydrogeldanamycin, which are disclosed in U.S. Pat. Nos. 4,261,989; 5,387,584; and 5,932,566, each of which is incorporated herein by reference. Other suitable Hsp90 inhibitors include radicicol and oximes and other analogs thereof, disclosed in Soga, et al., *Curr. Cancer Drug Targets,* 3, 359-69 (2003), and in Yamamoto, et al., *Angew. Chem.,* 42, 1280-84 (2003); and in Moulin, et al., *J. Amer. Chem. Soc.*, vol 127, 6999-7004 (2005); purine derivatives such as PU3, PU24FCI and PUH64 (see Chiosis et al., *ACS Chem. Biol.* Vol. 1(5), 279-284 (2006) and those disclosed in PCT Application No. WO 2002/0236075; related heterocyclic derivatives disclosed in PCT Application No. WO 2005/028434; and 3,4-diarylpyrazole compounds disclosed in Cheung, et al., *Bioorg. Med. Chem. Lett.*, vol. 15, 3338-43 (2005). Antibodies or antibody fragments that selectively bind to Hsp90 may also be administered as drugs to cause inhibition of Hsp90, and can be used in combination with the compounds of the invention.

Surgery involves the bulk removal of diseased tissue. While surgery can be effectively used to remove certain tumors, for example, breast, colon, and skin, it cannot be used to treat tumors located in areas that are inaccessible to surgeons. Additionally, surgery cannot typically be successfully used to treat non-localized cancerous indications including but not limited to leukemias and myelomas.

Radiation therapy (using ionizing electromagnetic or particulate radiation) may be used in conjunction with or in combination with a compound of the invention. Radiation therapy involves using high-energy radiation from x-rays, gamma rays, neutrons, and other sources ("radiation") to kill rapidly dividing cells such as cancerous cells and to shrink tumors. Radiation therapy is well known in the art (Hellman, *Cancer: Principles and Practice of Oncology,* 248-275, 4th ed., vol. 1 (1993)). Radiation therapy may be administered from outside the body ("external-beam radiation therapy"). Alternatively, radiation therapy can be administered by placing radioactive materials capable of producing radiation in or near the tumor or in an area near the cancerous cells. Systemic radiation therapy employs radioactive substances including but not limited to radiolabeled monoclonal antibodies that can circulate throughout the body or localize to specific regions or organs of the body. Brachytherapy involves placing a radioactive "seed" in proximity to a tumor. Radiation therapy is non-specific and often causes damage to any exposed tissues. Additionally, radiation therapy frequently causes individuals to experience side effects (such as nausea, fatigue, low leukocyte counts, etc.) that can significantly affect their quality of life and influence their continued compliance with radiation treatment protocols.

Chemotherapy involves administering chemotherapeutic agents that often act by disrupting cell replication or cell metabolism (e.g., by disrupting DNA metabolism, DNA synthesis, DNA transcription, or microtubule spindle function, or by perturbing chromosomal structural integrity by way of introducing DNA lesions). Chemotherapeutics are frequently non-specific in that they affect normal healthy cells as well as tumor cells. The maintenance of DNA integrity is essential to cell viability in normal cells. Chemotherapeutic agents must be potent enough to kill cancerous cells without causing too much damage to normal cells. Therefore, anticancer drugs typically have very low therapeutic indices, i.e., the window between the effective dose and the excessively toxic dose can be extremely narrow because the drugs cause a high percentage of damage to normal cells as well as tumor cells. Additionally, chemotherapy-induced side effects significantly affect the quality of life of an individual in need of treatment, and therefore frequently influence the individual's continued compliance with chemotherapy treatment protocols.

Accordingly, the compounds and methods of the invention may be used to reduce the amount of radiation, immunotherapy or chemotherapy required to control these conditions, and to overcome some of the limitations of these conventional therapies.

Where a compound of the invention is utilized in conjunction with or in combination with another therapeutic, the two agents may be co-administered, or they may be administered separately where their administration is timed so the two agents act concurrently or sequentially.

Accordingly, the compositions of the invention include at least one compound of the invention, and can optionally include one or more additional cytotoxic or cytostatic therapeutic such as, but not limited to, those disclosed above. Similarly, the methods of the invention include methods wherein a subject diagnosed as in need of treatment for cancer is treated with at least one compound or composition of the invention, and is simultaneously or concurrently treated with one or more of the additional therapeutic agents described above.

Formulations of the compounds and compositions of the invention may be prepared in a manner suitable for systemic administration or topical or local administration. Systemic formulations include those designed for injection (e.g., intramuscular, intravenous or subcutaneous injection) and those prepared for transdermal, transmucosal, or oral administration. The formulation will generally include a diluent as well as, in some cases, adjuvants, buffers, preservatives and the like. The compounds can be administered also in liposomal compositions or as microemulsions.

Injection methods are sometimes appropriate routes for administration of the compounds for systemic treatments and sometimes also for localized treatments. These include methods for intravenous, intramuscular, subcutaneous, and other methods for internal delivery that bypass the mucosal and dermal barriers to deliver the composition directly into the subject's living tissues.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised and can be utilized with the compounds of the invention. See, for example, U.S. Pat. No. 5,624,677. The present compositions can be utilized in such controlled-release delivery systems where appropriate.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, and the like as in understood in the art.

Selection of a particular route of administration for a given subject and indication is well within the ordinary level of skill in the art. For example, rectal delivery as a suppository is often appropriate where the subject experiences nausea and vomiting that precludes effective oral delivery. Transdermal patches are commonly capable of delivering a controlled-release dosage over several days or to a specific locus, and are thus suitable for subjects where these effects are desired.

Transmucosal delivery is also appropriate for some of the compositions and methods of the invention. Thus the compositions of the invention may be administered transmucosally using technology and formulation methods that are known in the art.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

For administration to animal or human subjects, the dosage of a compound of the invention is typically 10-2400 mg per administration. However, dosage levels are highly dependent on the nature of the condition, the condition of the patient, the judgment of the practitioner, and the frequency and mode of administration. Selection of a dosage of such compounds is within the skill of an ordinary artisan, and may be accomplished by starting at a relatively low dosage and increasing the dosage until an acceptable effect is achieved.

Frequency of administration of the compounds of the invention can also be readily determined by one skilled in the art using well known techniques. For example, the patient may be administered a low dosage of a compound or composition of the invention at a low frequency such as once per day or less often; and the dosage and/or frequency of administration may be systematically increased until a desired effect is achieved in the patient.

Compounds of the invention may be conveniently synthesized by coupling a suitably activated carboxylic acid compound bearing a water-solubilizing group at $R^5$, optionally in protected form, with a diazonamide core containing a free amino group, such as the diazonamide core shown in Scheme 2, under conditions that are routine in the art. The preparation of such diazonamide core molecules has been previously disclosed by the present applicants in U.S. Provisional Patent Application Ser. No. 60/933,916, to Hanson, et al., which was filed on Jun. 7, 2007, and is entitled METHODS FOR PREPARING DIAZONAMIDES, and U.S. Provisional Patent Application Ser. No. 60/954,275, to Hanson, et al., which was filed on Aug. 6, 2007, and is entitled METHODS FOR PREPARING DIAZONAMIDES, the contents of which are incorporated herein by reference in their entirety.

Those skilled in the art will appreciate that this coupling reaction can also be accomplished with other coupling reagents or by using activated esters, such as by way of example only, N-hydroxysuccinimide ester, perfluorophenyl ester, N-hydroxyphthalimide esters, activated esters generated by the reaction of the carboxylic acid with a carbodiimide, and other activated esters conventionally used for acylation of an amine to form amide bonds; thus the invention provides method to prepare compounds of the invention by coupling an activated carboxylic acid derivative, which may optionally be protected, with the above described amine.

The amine may also optionally be in protected form, i.e. it may have protecting groups on either or both of the indole nitrogen and the indoline nitrogen. Suitable protecting groups for use on the water-solubilizing group will vary depending on the nature of the group. For example, as shown in Scheme 1, the phosphate group may be protected as a bis-benzyloxy derivative. Suitable protecting groups for use on the ring nitrogen atoms of the amine compound, which are not intended to react with the activated ester, may include acyl groups such as carbamates or trifluoroacetate, as well as silyl groups. Suitable protecting groups and methods to attach and remove them are well known in the art, and are described, for example, in T. H. Greene, PROTECTIVE GROUPS IN ORGANIC SYNTHESIS, $2^{nd}$ ed.

Scheme 1 describes the preparation of macrocyclic oxazole intermediate 8, through a series of steps (see Examples 1-8) featuring an electrochemical oxidative cyclization as a key step.

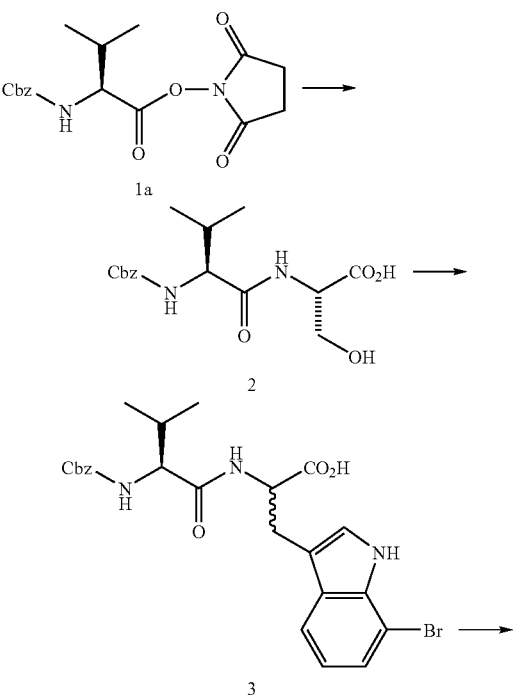

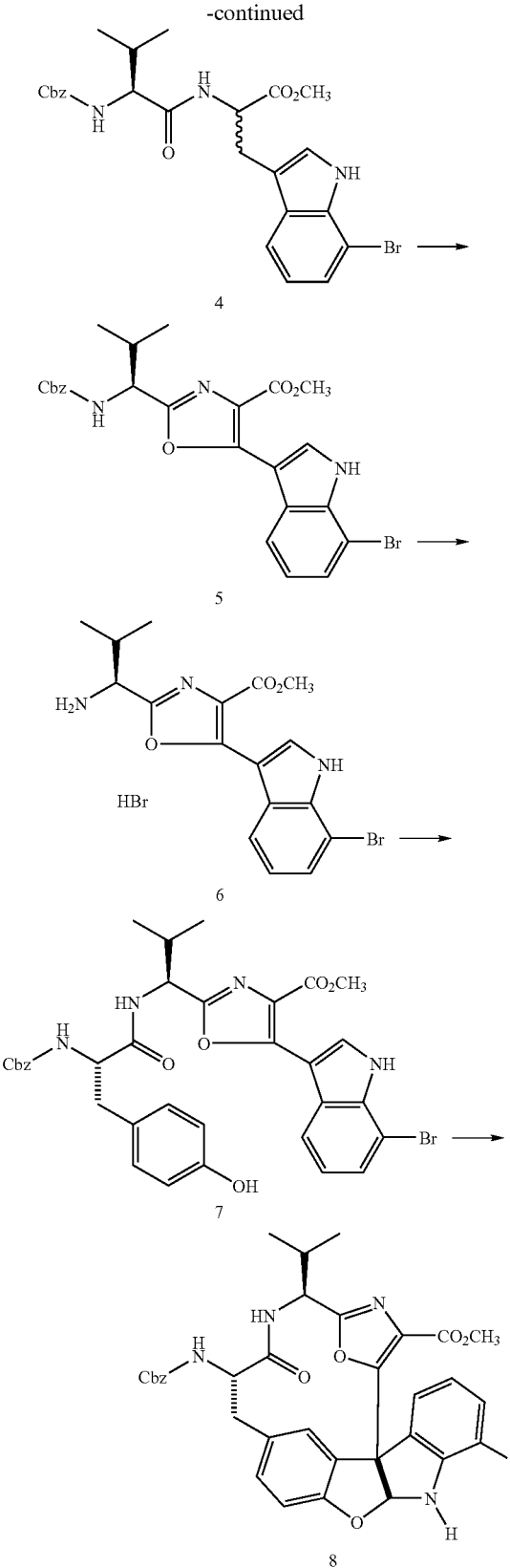
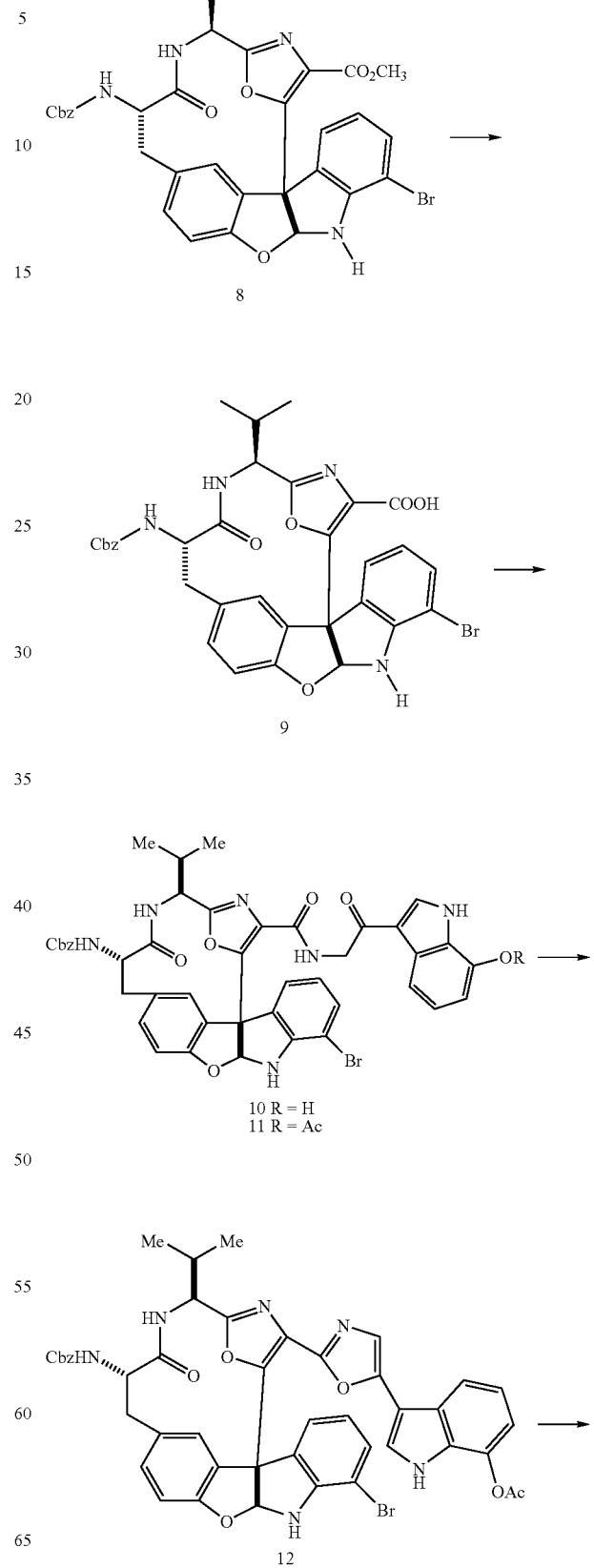
Scheme 2 describes the conversion of compound 8 to compound 16, via the intermediacy of diazonamide core molecule, compound 15 (see Examples 9-16).

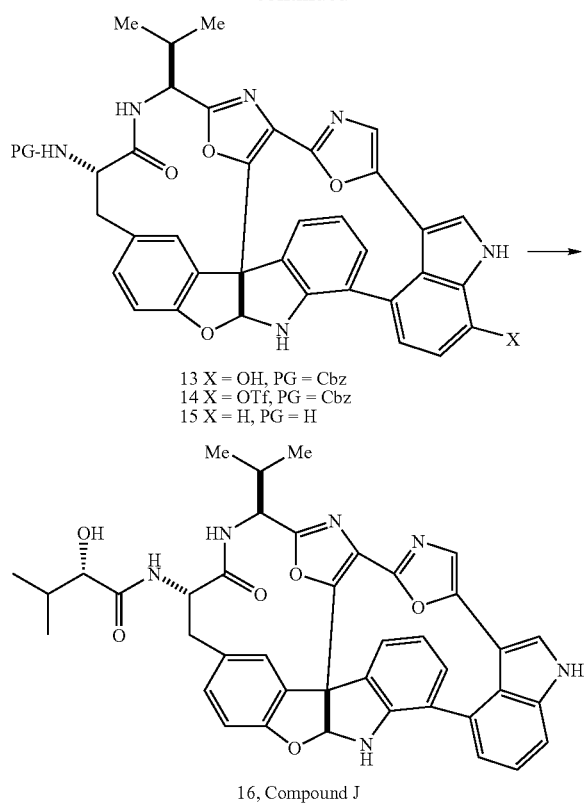

13 X = OH, PG = Cbz
14 X = OTf, PG = Cbz
15 X = H, PG = H

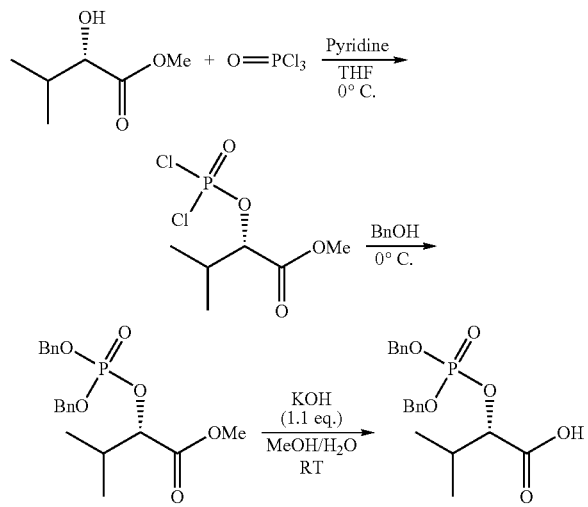

16, Compound J

Scheme 3 provides two routes for the preparation of (S)-2-(bis(benzyloxy)-phosphoryloxy)-3-methylbutanoic acid (see Examples 17-20).

Scheme 3

Route A:

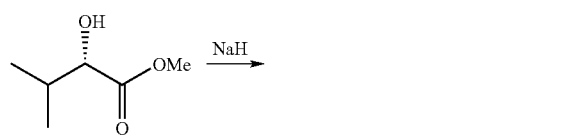

Route B:

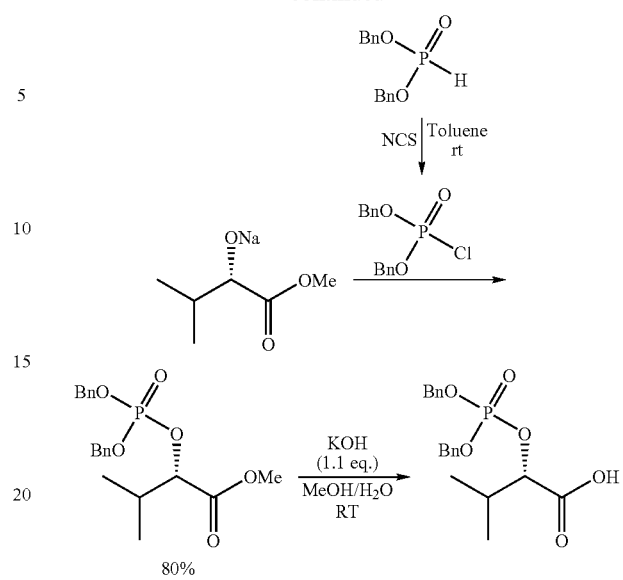

Scheme 4 describes coupling of compound 15 with (S)-2-(bis(benzyloxy)-phosphoryloxy)-3-methylbutanoic acid, followed by deprotection of the bis-benzyl phosphate ester to provide the free acid, which is further converted to its monosodium salt (see Examples 21-23).

Scheme 4.

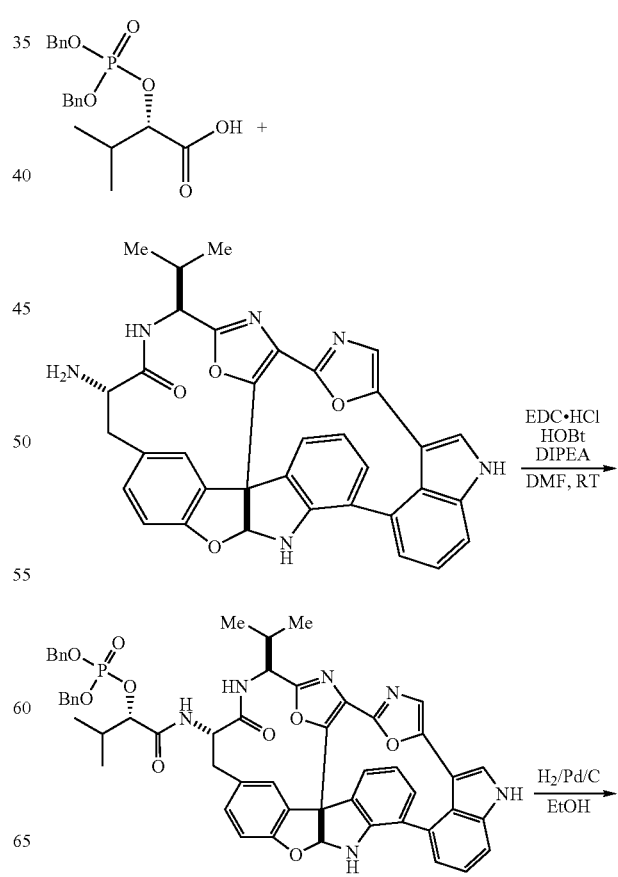

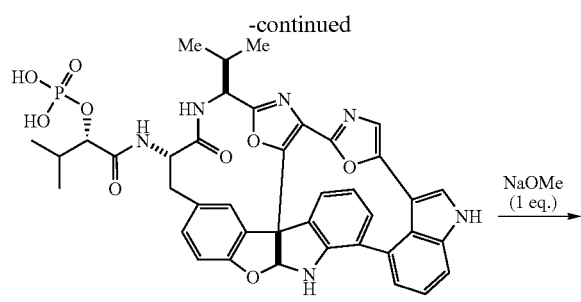

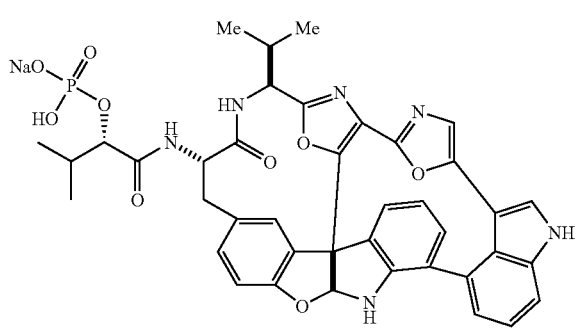

Scheme 5 (see Examples 24-25) describes the preparation of (S)-2-benzyloxy-3-methylbutanoic acid.

Scheme 5.

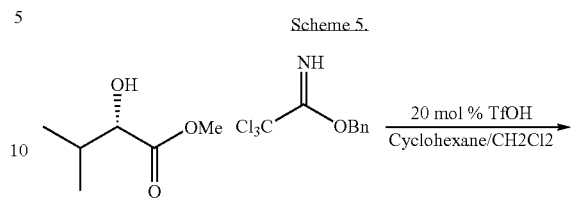

Scheme 6 describes the coupling of (S)-2-benzyloxy-3-methylbutanoic acid with compound 15 as shown in to give intermediate, compound 26. Phosphorylation of the indole nitrogen, followed by deprotection of all protecting groups, provided the indole phosphoric acid amide, compound 28 (see Examples 24-28).

Scheme 6.

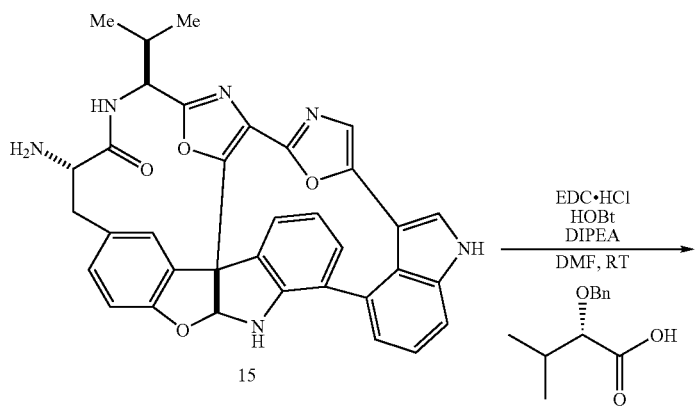

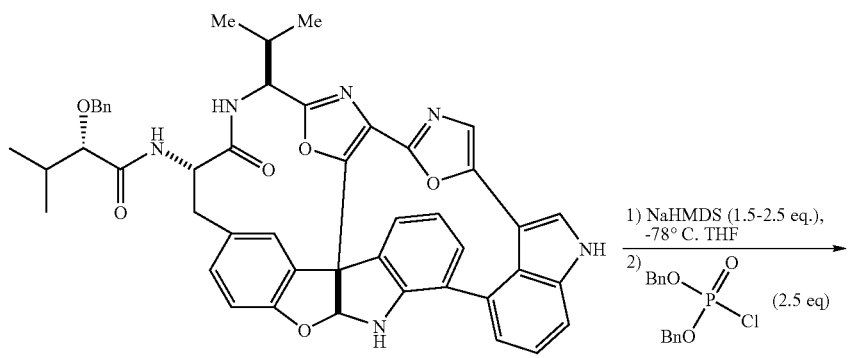

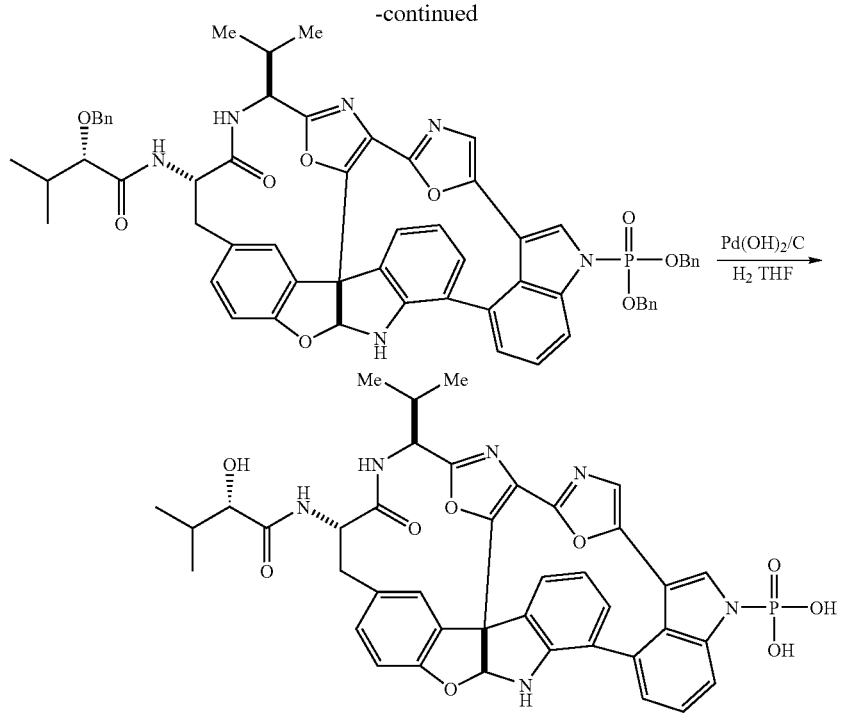

Scheme 7 provides a route to the preparation of compounds bearing a methylene linker between the indole nitrogen atom and the phosphate moiety. The indole nitrogen is alkylated with a formyl equivalent to install a hydroxymethylene moiety, which is mesylated and then further reacted with dibenzyl phosphate to install the protected phosphate group. Deprotection of the benzyl esters by hydrogenolysis provides the free acid, which can be converted to the mono-sodium or di-sodium salt by reaction with the appropriate amount of sodium hydroxide.

Scheme 7

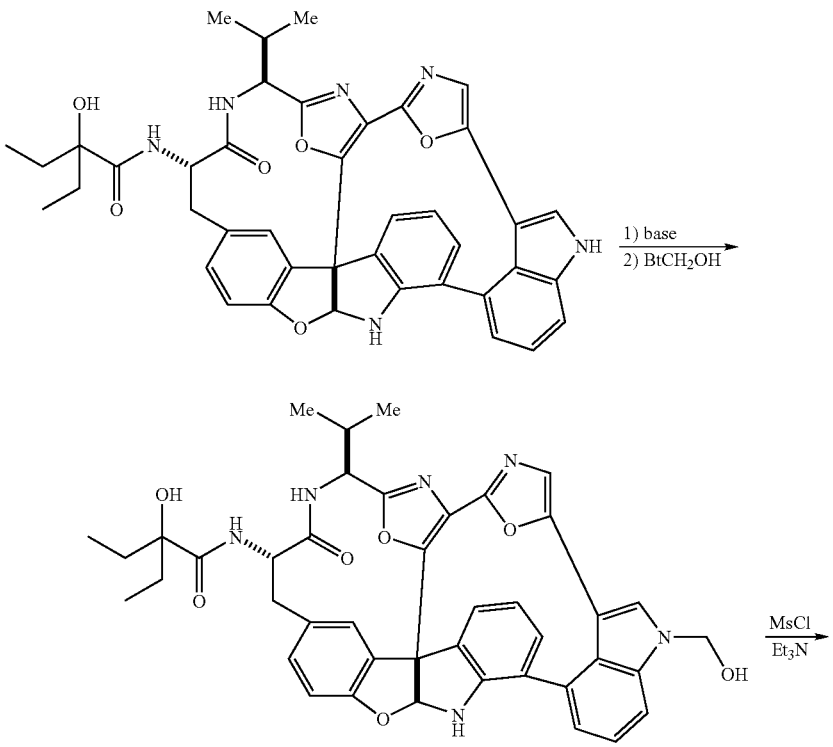

-continued
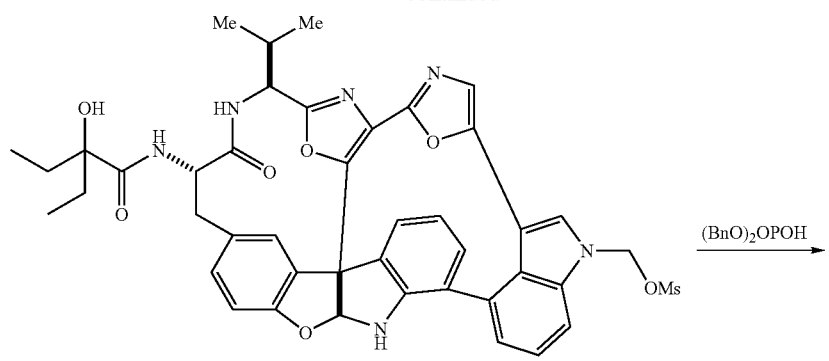
(BnO)₂OPOH →
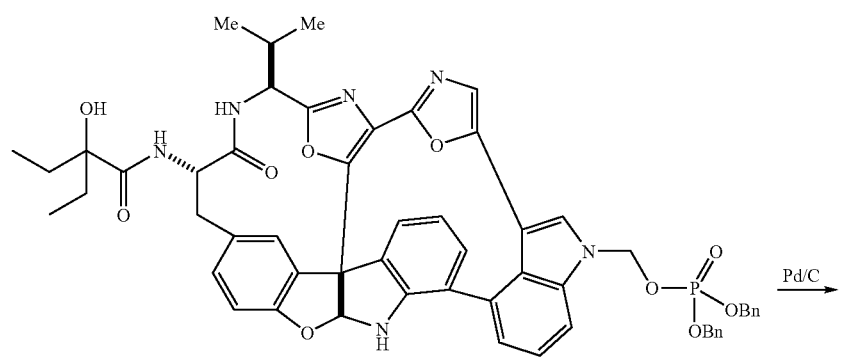
Pd/C →
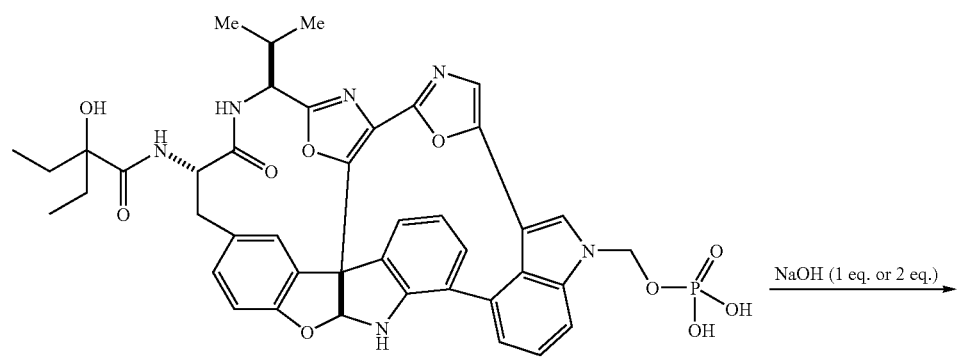
NaOH (1 eq. or 2 eq.) →
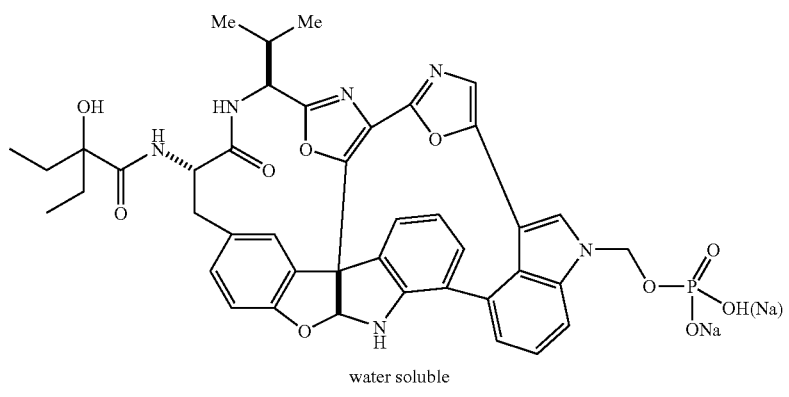
water soluble Unless otherwise specified, all documents referred to herein are incorporated by reference in their entirety.

The following examples are offered to illustrate but not to limit the invention.

In the examples described below, unless otherwise indicated all temperatures are set forth in degrees Celsius (° C.) and all parts and percentages are by weight. Reagents were purchased from commercial suppliers such as Aldrich Chemical Company or Lancaster Synthesis Ltd. and were used without further purification unless otherwise indicated.

$^1$H-NMR spectra were recorded on a Bruker or Varian instrument operating at 300, 400 or 500 MHz. $^1$H-NMR spectra were obtained as $CDCl_3$ solutions (reported in ppm), using chloroform as the reference standard (7.27 ppm), or in DMSO-d6 or $CD_3OD$ (3.4 and 4.8 ppm), or using tetramethylsilane (0.00 ppm) as an internal standard, when appropriate. Other NMR solvents were used as needed.

Mass spectrometry (MS) was conducted with various techniques. Mass spectra were typically obtained using liquid chromatograph electrospray ionization mass spectrometry, MS (ESP).

Where appropriate, the reactions were also assayed by HPLC. These synthetic pathways and experimental procedures utilize many common chemical abbreviations, such as $NaHCO_3$ (sodium bicarbonate), $Na_2CO_3$ (sodium carbonate), pTsOH (p-toluenesulfonic acid monohydrate), TLC (thin layer chromatography), $Na_2SO_4$ (sodium sulfate), $NaHSO_4$ (sodium bisulfate), MTBE (methyl t-butyl ether), THF (tetrahydrofuran), DMF (N,N-dimethylformamide), EtOAc (ethyl acetate), EDC (1-(3-dimethylaminopropyl)-3-ethylcarbodiimide hydrochloride), DHOBT (3,4-dihydro-3-hydroxy-4-oxo-1,2,3-benzotriazine), HOBT (1-hydroxybenzotriazole hydrate), DIEA (diisopropylethylamine), Pd/C (palladium on charcoal, 10% wt/wt), Bn (benzyl), and the like.

Example 1

7-Bromoindole

2-Bromonitrobenzene (1.10 kg, 5.45 mol) was dissolved in tetrahydrofuran (10 L) at room temperature. This solution was cooled with stirring in a bath maintained at −78° C. When the internal temperature reached −40° C., vinylmagnesium bromide (16.3 L, 16.3 mol) was added at such a rate as to maintain the internal temperature at −40° C. during the addition. Upon complete addition, the reaction was removed from the bath and allowed to warm slowly to −30° C. over the course of 45 minutes. This required occasional cooling. The −30° C. reaction solution was quenched by rapid addition of a slightly cool (~10° C.) solution of saturated aqueous $NH_4Cl$ (10 L). Slight foaming occurred. (Inverse quench into the ammonium chloride solution is also satisfactory.) This resulted in a biphasic mixture with some undissolved magnesium salts in the form of a gel. The mixture was stirred for 30 minutes and separated. The aqueous layer was back extracted with tetrahydrofuran (10 L). The combined organic layers were evaporated at reduced pressure with a bath temperature of 35° C. and the resulting dark oil was taken up in methylene chloride (5 L) and dried with $Na_2SO_4$. The mixture was filtered and concentrated. The resulting material was chromatographed, eluting with 2% ethyl acetate-hexanes to give 7-bromoindole (557 g, 52% yield) as an off-white solid. $^1$H NMR ($CDCl_3$): consistent with proposed structure.

Example 2

Cbz-Val-Ser-OH

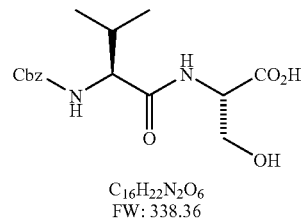

$C_{16}H_{22}N_2O_6$
FW: 338.36

L-Serine (104.19 g, 991 mmol) was dissolved in water (1440 mL) in a 4-L Erlenmeyer flask. Solid $NaHCO_3$ (83.25 g, 991 mmol was added and the mixture was stirred at room temperature to give a clear solution. Cbz-Val-OSu (300.0 g, 861 mmol) was added as a solution in 1,4-dioxane (1500 mL), with additional 1,4-dioxane (220 mL) used to rinse. The resulting cloudy mixture became clear after 1.5 h of stirring at 25° C. After 44 h, the mixture was divided into two equal portions. Methanol (700 mL) and 12 N aqueous HCl (42 mL, 504 mmol) was added to each portion, followed by EtOAc (1000 mL) and a solution of NaCl (100 g) dissolved in water (600 mL). The layers were separated and the organic layer was washed with saturated aqueous NaCl (350 mL). The aqueous layers were extracted in succession with EtOAc (1000 mL). The organic layers resulting from work-up of both portions of the reaction were combined, dried ($Na_2SO_4$), filtered, and evaporated to give a white solid (351 g). This material was suspended in $CH_2Cl_2$ (1500 mL) and stirred for 2 h. The mixture was filtered and the crystals were washed with $CH_2Cl_2$ (1000 mL) to give compound 2 as white crystals (262.3 g, 90% yield). $^1$H NMR (300 MHz, DMSO-d$_6$): consistent with proposed structure for compound 2. MS: m/z=339.1 (M+1).

Example 3

Cbz-Val-(7-Bromo-Trp)-OH

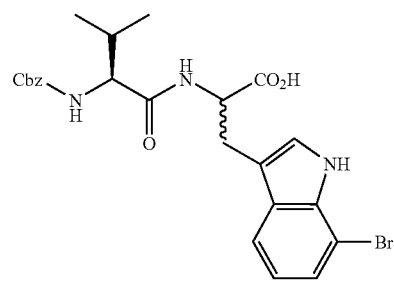

$C_{24}H_{26}BrN_3O_5$
FW: 516.38

Acetic acid (180 mL) was added to Cbz-Val-Ser-OH (42.89 g, 127 mmol) and 7-bromoindole (30.96 g, 158 mmol) in a round-bottom flask fitted with a mechanical stirrer, reflux condenser, and internal thermometer. Acetic anhydride (40 mL, 43 g, 420 mmol) was added and the mixture was heated to 80° C. over 40 min. Heating was continued at this temperature for 4 h. After cooling to room temperature and standing overnight, the mixture was diluted with ethyl ether (180 mL) and stirred for 30 min. The mixture was filtered and the crystals were washed with ethyl ether (250 mL). Drying of the crystals yielded compound 3 (42.49 g, 65% yield). $^1$H NMR (300 MHz, DMSO-$d_6$): consistent with proposed structure for compound 3. MS: m/z=516.0 (M+1).

Example 4

Cbz-Val-(7-Bromo-Trp)-OMe

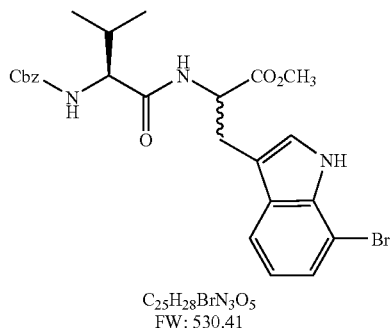

$C_{25}H_{28}BrN_3O_5$
FW: 530.41

Concentrated aqueous HCl (60 mL, 720 mmol) was added to a stirred suspension of starting material 3 (32.53 g, 63.0 mmol) in 2,2-dimethoxypropane (1200 mL, 1020 g, 9.8 mol). After stirring for 24 h at 25° C., most of the solvent was evaporated to give wet crystals. MTBE (250 mL) was added and the mixture was allowed to stand with occasional swirling over 3 h. Filtration and washing of the crystals with MTBE (100 mL) gave compound 4 (30.31 g, 91% yield). $^1$H NMR (300 MHz, DMSO-$d_6$): consistent with proposed structure for compound 4. MS: m/z=530.1 (M+1).

Example 5

Methyl 2-((S)-1-(benzyloxycarbonylamino)-2-methylpropyl)-5-(7-bromo-1H-indol-3-yl)oxazole-4-carboxylate

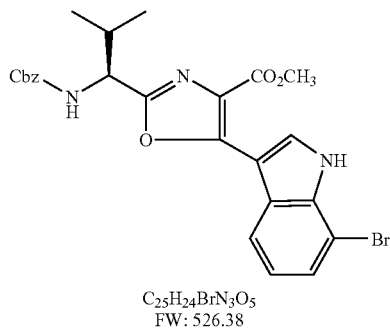

$C_{25}H_{24}BrN_3O_5$
FW: 526.38

A solution of DDQ (28.41 g, 125 mmol) in tetrahydrofuran (251 g, 282 mL) was added to starting material 4 (30.20 g, 56.9 mmol) in tetrahydrofuran (848 g, 954 mL) and the dark solution was heated to gentle reflux in an oil bath at 85° C. for 6 h. After cooling and standing overnight at room temperature, the solvent was removed on a rotary evaporator. Methanol (200 mL) was added and the solvent was evaporated to leave a brown crusty solid (91 g). Methanol (200 mL) was added and the solid was loosened with a spatula. The mixture was swirled until the appearance changed to a red liquid containing a yellow precipitate. The mixture was filtered and the precipitate was washed with methanol (60 mL). The pale gray crystals were air dried and then dried under vacuum to give compound 5 (17.98 g, 60% yield). $^1$H NMR (300 MHz, DMSO-$d_6$): consistent with proposed structure for compound 5. MS: m/z=526.0 (M+1).

Example 6

Methyl 2-((S)-1-amino-2-methylpropyl)-5-(7-bromo-1H-indol-3-yl)oxazole-4-carboxylate hydrobromide

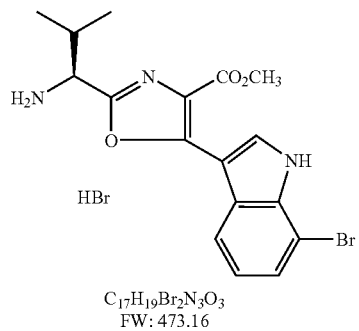

$C_{17}H_{19}Br_2N_3O_3$
FW: 473.16

Glacial acetic acid (25 mL) was added to starting material 5 (9.99 g, 19.0 mmol) in a 500-mL round-bottom flask fitted with a mechanical stirrer. The suspension was stirred at 25° C. and 33% HBr in acetic acid (50 mL) was added in one portion. The mixture became homogeneous and then a precipitate formed in 5-10 min. After 1 h, MTBE (235 mL) was added and stirring was continued at 25° C. for another 1 h 20 min. The mixture was filtered and the precipitate was washed with MTBE (150 mL). The cream-colored powder was dried under vacuum to give compound 6 (8.91 g, 99% yield). $^1$H NMR (300 MHz, DMSO-$d_6$): consistent with proposed structure for compound 6. MS: m/z=392.0 (M+1).

Example 7

Methyl 2-((S)-1-((S)-2-(benzyloxycarbonylamino)-3-(4-hydroxyphenyl)propanamido)-2-methylpropyl)-5-(7-bromo-1H-indol-3-yl)oxazole-4-carboxylate

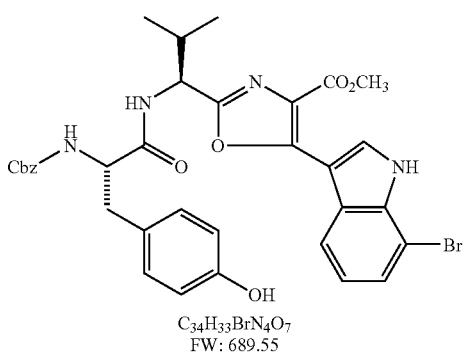

$C_{34}H_{33}BrN_4O_7$
FW: 689.55

DMF (100 mL) was added to the starting material 6 (9.16 g, 19.4 mmol), HOBt (3.17 g, 23.5 mmol), and Cbz-Tyr-OH (6.44 g, 20.4 mmol) in a round-bottom flask. Diisopropylethylamine (4.22 mL, 3.13 g, 129 mmol) was added, followed by EDC (4.15 g, 21.6 mmol). After stirring for 24 h at 25° C., the solution was diluted with EtOAc (500 mL) and the mixture was washed with 1 N aqueous HCl (250 mL), saturated aqueous sodium bicarbonate (250 mL), and saturated aqueous sodium chloride (250 mL). The solution was dried ($Na_2SO_4$), decanted, and evaporated to give a tan solid. This material was dissolved in 2-PrOH (180 mL) at 90° C. Hexanes (85 mL) were added and the solution was allowed to cool to room temperature. After standing overnight, the mixture was cooled to 5° C. for 4 h. The solid was separated by filtration and washed with 1:1 2-PrOH/hexanes (140 mL). This material, which at this point held residual solvent, was dried on a vacuum manifold to give compound 7 (11.58 g, 87% yield). $^1$H NMR (300 MHz, DMSO-$d_6$): consistent with proposed structure for compound 7. MS: m/z=689.0 (M+1).

Example 8

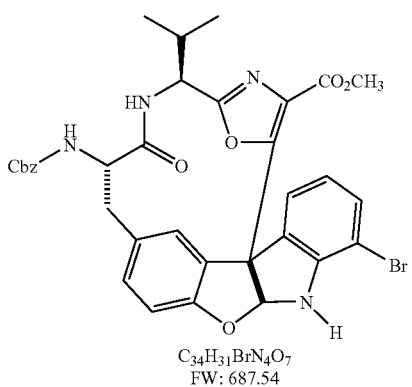

$C_{34}H_{31}BrN_4O_7$
FW: 687.54

An electrochemical cell was assembled using a 1500-mL beaker and a custom polypropylene rack which supported 24 vertical graphite rods (6.15 mm diameter×150 mm length). The rods were arranged in an approximately circular pattern with 7 mm between the sides of the rods. Electrical connections were made such that the electrodes were in an alternating pattern of two anodes and one cathode. The phenolic starting material 7 (5.00 g, 7.25 mmol) and $Et_4NBF_4$ (10.00 g, 46.1 mmol) were dissolved in DMF (1100 mL) in the beaker, and 0.5 N aq. KOH (15 mL, 7.5 mmol) was added, resulting in electrode immersion depth of 11 cm. The solution was stirred vigorously with a 4-bladed turbine (50 mm diameter, blades at 45° angle to shaft, approx. 500 rpm). The electrochemical reaction was carried out for 5.3 days at a constant potential of 1.7 volts. At that point approximately 1.26 amp-h of current had passed, and only 6.5% of the original SM remained as determined by HPLC integration at 220 nM. The reaction mixture was concentrated on a rotary evaporator (bath temp. ≦35° C.) and dried further on a vacuum manifold. The residue was partitioned between EtOAc (250 mL) and 1 N aq. HCl (100 mL). The organic layer was washed with saturated aq. $NaHCO_3$ (50 mL) and then saturated aq. NaCl (50 mL). The aq. layers were extracted in succession with EtOAc (100 mL). The combined organic layers were dried ($Na_2SO_4$), decanted and evaporated to give 4.85 g of crude product. Flash column chromatography on silica gel (50 g), eluting with 25% EtOAc in $CH_2Cl_2$ gave 1.87 g (38% yield) of compound 8 as a mixture of stereoisomers (81:19 as measured by HPLC integration at 220 nM).

Example 9

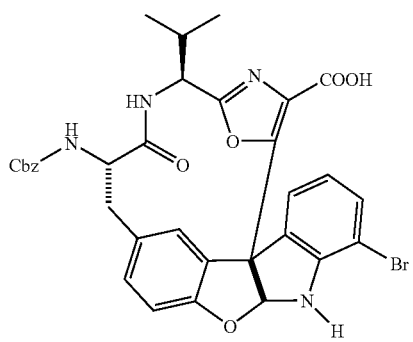

To a 1-L three-neck round-bottom flask equipped with a thermometer, an addition funnel and a magnetic stir bar was added the starting methyl ester (6.92 g, 10.03 mmol, containing ca. 80% of diastereomer 8) and methanol (240 mL). The solution was cooled to 5° C. in ice-water bath followed by addition of lithium hydroxide in water (2.40 g/44 mL, 100.3 mmol, 10 eq.) at 5-10° C. with stirring. After addition the reaction mixture became a slurry. The cooling bath was removed and the mixture was allowed to warm to room temperature. The precipitate disappeared gradually. After 4.5 h stirring at room temperature less than 2% of starting material remained as determined by LCMS. Ice (440 g) was added to the reaction mixture and HCl/$H_2O$ (1 N, 105 mL) was added dropwise from an addition funnel with vigorous stirring to acidify the 0° C. reaction mixture. The pH of the mixture was adjusted to 2.5-3.0. A pale yellow solid precipitated, which was extracted using EtOAc (400 mL). The aqueous phase was concentrated to remove most of the methanol and then extracted with EtOAc (2×100 mL). The combined organic layers was dried over $Na_2SO_4$ and concentrated to afford crude compound 9 (6.43 g, 9.6 mmol, as a ca. 80:20 mixture containing by-product hydantoin) which was used directly in the next step without further purification. $^1$H NMR (400 MHz, $CDCl_3$): consistent with proposed structure for compound 9. MS: m/z=673.2 (M+1).

Example 10

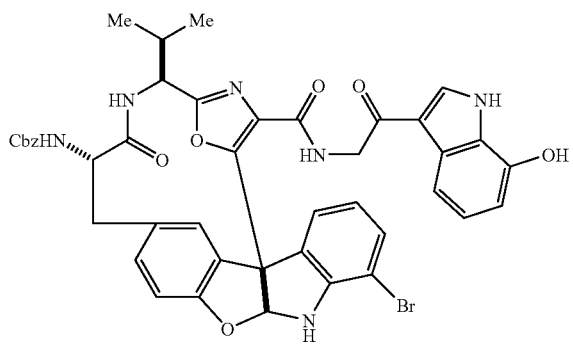

To a dry 250-mL round-bottom flask with magnetic stir bar was added DHOBt (545 mg, 3.34 mmol, 0.35 eq.), EDC.HCl (2.75 g, 14.32 mmol, 1.5 eq.), anhydrous DMF (130 mL) and TEA (2.0 mL, 14.32 mmol, 1.5 eq.). The resulting reagent mixture was stirred for 20 min. To another dry 500-mL round-bottom flask was added the crude compound 9 (6.43 g, 9.6 mmol), 2-amino-1-(7-hydroxy-1H-indol-3-yl)ethanone hydrochloride (3.25 g, 14.32 mmol, 1.5 eq.) and DMF (30 mL). Then TEA (2.0 mL, 14.32 mmol, 1.5 eq) was added dropwise followed by the addition of the reagent mixture above. The resulting reaction mixture was stirred for 6 h at 40-42° C. and cooled to room temperature overnight. About 4% of starting acid remained as determined by LCMS. Most of DMF was removed under vacuum at 45° C. Less than 1% of starting material remained. The residue was diluted with EtOAc (800 mL)/water (200 mL). Some undissolved brown solid was removed by filtration. The organic phase was separated and the aqueous phase was extracted by EtOAc (2×100 mL). The combined organic layers were washed by water (100 mL), 10% aqueous NaHSO$_4$ (100 mL), water (100 mL), saturated NaHCO$_3$ (100 mL), water (2×100 mL) and brine (100 mL), and then dried over Na$_2$SO$_4$. After concentration the crude compound 10 (8.4 g, 9.6 mmol) was obtained and used directly in next step without further purification. $^1$H NMR (400 MHz, CDCl$_3$): consistent with proposed structure for compound 10. MS: m/z=845.1 (M+1).

Example 11

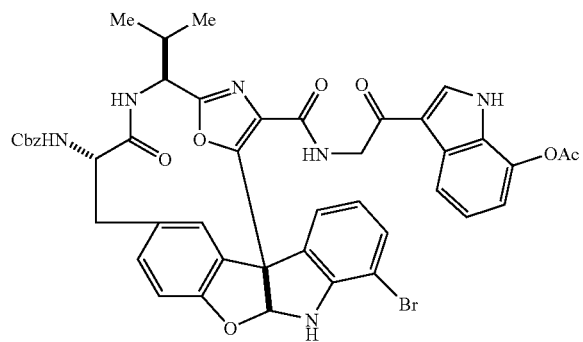

To a dry 500-mL flask containing crude compound 10 (8.4 g, 9.6 mmol) was added anhydrous tetrahydrofuran (40 mL) and anhydrous CH$_2$Cl$_2$ (150 mL). The resulting solution was cooled to 0° C. in ice-water bath. Acetic anhydride (2.69 mL, 28.65 mmol, 3.0 eq.) and pyridine (1.16 mL, 14.33 mmol, 1.5 eq.) were added sequentially at 0° C. Then the mixture was allowed to warm to room temperature and stirred under N$_2$. The reaction was monitored using LCMS. After 3.5 h only 2% of starting material was not consumed and 2% of over-acetylated product was formed. The reaction solution was diluted with ethyl acetate (700 mL) followed by washing with water (3×100 mL) and brine (100 mL) and drying over Na$_2$SO$_4$. After concentration, crude compound 11 was purified by flash chromatography eluting with a EtOAc-CH$_2$Cl$_2$ gradient (30/70 to 35/65) to afford desired compound 11 (4.56 g, 5.14 mmol, 51% yield over three steps) from compound 8 which was 80% pure. $^1$H NMR (400 MHz, CDCl$_3$): consistent with proposed structure for compound 11. MS: m/z=887.1 (M+1).

Example 12

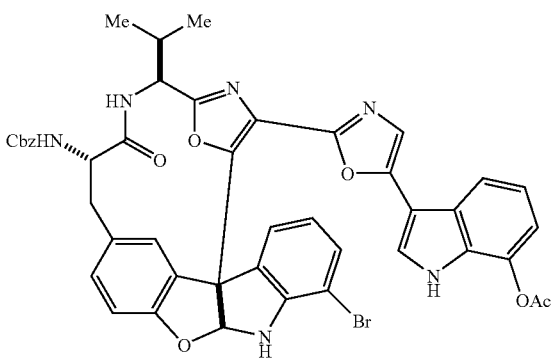

Triphenylphosphine (13.48 g, 51.4 mmol, 10 eq.) and hexachloroethane (12.17 g, 51.4 mmol, 10 eq.) were added to a dry 1-L three-neck round-bottom flask equipped with a thermometer, an addition funnel and a magnetic stir bar. Anhydrous CH$_2$Cl$_2$ (320 mL) was added and the resulting solution was cooled to 10° C. in ice-water bath under N$_2$. TEA (10.03 mL, 71.96 mmol, 14 eq.) was added slowly to the solution, followed by stirring for 10 min at 10° C. The solution of compound 11 (4.56 g, 5.14 mmol, 1 eq.) in anhydrous CH$_2$Cl$_2$ (160 mL) was added dropwise over 5 min. and the temperature was kept at 10-12° C. The reaction mixture was stirred at 10° C. for another 10 min, and TLC showed that no starting material left. The reaction mixture was cooled to −30° C. followed by addition of phosphate buffer (200 mL, pH=6.9, 0.5 M) to consume excess reagents. The resulting reaction mixture was stirred in cold room (4° C.) for 48 h. Most of triphenylphosphine was consumed as determined by LCMS. The organic phase was separated and the aqueous phase was extracted by CH$_2$Cl$_2$ (2×100 mL). Combined organic phase was washed by water (100 mL) and brine (100 mL) and dried over Na$_2$SO$_4$. All solvent was removed under reduced pressure on a rotary evaporator followed by the addition of ethyl acetate (40 mL) to precipitate triphenylphosphine oxide. After filtering and washing with CH$_2$Cl$_2$, the filtrate was concentrated. The crude compound 12 was purified by flash chromatography eluting with EtOAc/toluene (60/40; column 4×28 cm) to give desired compound 12 (3.41 g, 3.92 mmol, 76% yield). $^1$H NMR (400 MHz, CDCl$_3$): consistent with proposed structure for compound 12. MS: m/z=869.1 (M+1).

Example 13

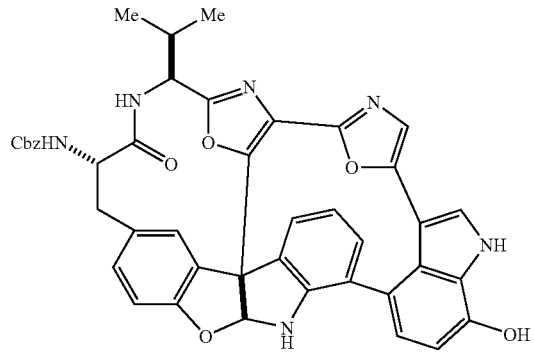

The solution of compound 12 (1.2 g, 1.38 mmol) in acetonitrile (400 mL) was added to a 500-mL flask of a Hanovia photoreactor in a photochemical safety cabinet. The solution was degassed by a stream of argon for 30 min. Then a pre-degassed aqueous solution of lithium hydroxide (83 mg/70 mL, 3.45 mmol, 2.5 eq.) was added by syringe. The resulting solution was degassed again for another 1 h. The door of cabinet was closed. Then the water flow (for cooling the UV lamp) was turned on and UV lamp (with Pyrex filter) was turned on. The reaction solution was irradiated with UV for 120 min followed by quenching with 70 mL of saturated NH₄Cl. The organic phase was separated and the aqueous phase was extracted with ethyl acetate (2×100 mL). The combined organic phase was washed with brine (100 mL) and dried over Na₂SO₄. This photoreaction protocol was performed three times using a total of 3.41 g (3.92 mmol) of starting material 12. All crude product was combined and purified by flash chromatography eluting with an EtOAc-CH₂Cl₂ gradient (40:60 to 55:45) to afford desired compound 13 (1.29 g, 1.72 mmol, 44% yield). $^1$H NMR (400 MHz, CDCl₃): consistent with proposed structure for compound 13. MS: m/z=747.2 (M+H⁺). Deacetylated starting material (865 mg, 1.05 mmol, 27% yield) was recovered.

Example 14

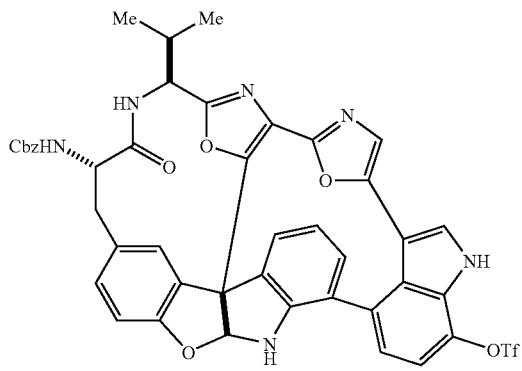

To a dry 250-mL two-neck round-bottom flask equipped with a thermometer containing compound 13 (1.29 g, 1.72 mmol) was added anhydrous CH₂Cl₂ (100 mL) and TEA (0.719 mL, 5.16 mmol, 3.0 eq.). The suspension was cooled to 0° C. in ice-brine bath followed by addition of the solution of trifluoromethanesulfonic anhydride (0.407 mL, 2.41 mmol, 1.4 eq.) in anhydrous CH₂Cl₂ (14 mL) dropwise at 0° C. The mixture was stirred at 0° C. under N₂ for 2 h and TLC showed that all starting material was consumed. Saturated NaHCO₃ (20 mL) was added to quench the reaction. The organic phase was separated, washed by water (30 mL) and brine (2×30 mL) and dried over Na₂SO₄. The solution was concentrated to afford crude compound 14 (1.50 g, 1.71 mmol) which was used directly in next step without further purification. $^1$H NMR (400 MHz, CDCl₃): consistent with proposed structure for compound 14. MS: m/z=879.2 (M+1).

Example 15

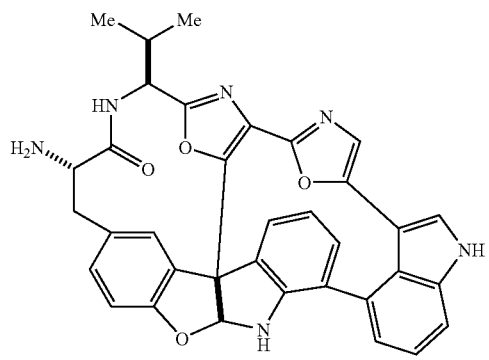

To a 250-mL round-bottom flask containing crude compound 14 (1.47 g, 1.67 mmol) was added methanol (75 mL) and TEA (0.838 mL, 6.0 mmol, 3.6 eq.). The flask was purged with N₂ flow for 10 min followed by addition of Pd(OH)₂/C (2.64 g, 20%, 3.76 mmol, 2.2 eq.) under N₂. H₂ balloon was added and the flask was purged with H₂ four times. Then hydrogen-filled balloon was opened to the reaction system. After 6.5 h stirring about 5% of starting material remained. The reaction was stopped. The reaction mixture was filtered through a pad of Celite and the black cake was washed with methanol (5×15 mL). The filtrate was concentrated and the residue was dissolved in CH₂Cl₂ (500 mL). The resulting solution was washed with water (3×100 mL), brine (100 mL), and dried over Na₂SO₄. The solution was concentrated to afford crude compound 15 (930 mg, 1.56 mmol) which was used directly in next step without further purification. $^1$H NMR (400 MHz, CD₃OD): consistent with proposed structure for compound 15. MS: m/z=597.2 (M+1).

Example 16

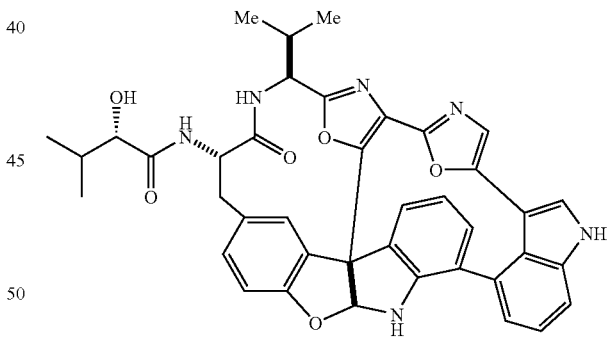

To a dry 100-mL round-bottom flask containing compound 15 (930 mg, 1.56 mmol) was added anhydrous tetrahydrofuran (45 mL). The solution of N-hydroxysuccinimide ester of (S)-2-hydroxy-3-methylbutyric acid (503 mg, 2.34 mmol, 1.5 eq.) in anhydrous tetrahydrofuran (4 mL) was added dropwise at room temperature under N₂. The resulting reaction solution was stirred for 18 h. Less than 5% of starting material remained. All solvent was evaporated under reduced pressure and the residue was dissolved in methanol (200 mL). The solution was cooled to 0° C. in ice-water bath followed by the addition of aqueous KOH (1 N, 7 mL) to consume excess reagent. The solution was stirred at 0° C. for 30 min. Then saturated NH₄Cl (40 mL) was added at 0° C. to neutralize the base. Most of the methanol was evaporated under reduced pressure and the residue was dissolved in EtOAc (500 mL) followed by washing with saturated NaHCO$_3$ (100 mL), water (2×100 mL) and brine (100 mL) and dried over Na$_2$SO$_4$. The solution was concentrated and the crude was purified by flash chromatography eluting with EtOAc/CH$_2$Cl$_2$ gradient (60/40, 70/30, 80/20 and pure EtOAc) to afford desired compound 16 (563 mg, 0.808 mmol, 48% combined yield over three steps from compound 13). $^1$H NMR (500 MHz, CD$_3$OD): consistent with proposed structure for compound 16. MS: m/z=697.2 (M+1).

Example 17

Methyl(S)-2-hydroxy-3-methylbutyrate

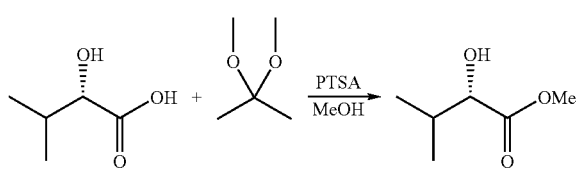

To a dry 15 mL flask was added (S)-(+)-2-hydroxy-3-methylbutyric acid (1.0 g, 8.47 mmol, 1 eq.), anhydrous methanol (1 mL), 2,2-dimethoxypropane (1.04 mL, 8.47 mmol, 1.0 eq.) and p-toluenesulfonic acid monohydrate (11 mg, 0.059 mmol, 0.007 eq.) under N2. The resulting solution was warmed to 45° C. and stirred for 18 hrs. The reaction was monitored by TLC. No starting material remained. All solvent was evaporated under reduced pressure. The residue was diluted with ethyl acetate (30 mL), and washed with saturated aqueous NaHCO$_3$ (10 mL), water (3×10 mL) and brine (10 mL). The organic layers were dried over Na$_2$SO$_4$ and concentrated to afford crude compound 17 (670 mg), which was used directly in the next step without further purification. $^1$H NMR (300 MHz, CDCl$_3$): consistent with proposed structure.

Example 18

(S)-methyl 2-(bis(benzyloxy)phosphoryloxy)-3-methylbutanoate

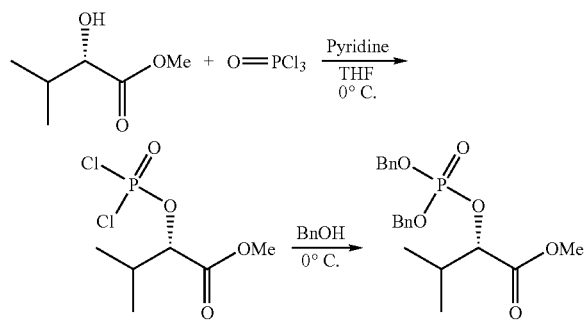

To a flame-dried 15 mL flask was added phosphorous oxychloride (209 µL, 2.25 mmol, 1.1 eq.), anhydrous tetrahydrofuran (2.3 mL) and anhydrous pyridine (330 µL, 4.08 mmol, 2.0 eq.) under N$_2$. A solution of compound 17 (from example 17), methyl(S)-2-hydroxy-3-methylbutyrate (270 mg, 2.04 mmol, 1.0 eq.) in anhydrous tetrahydrofuran (2.0 mL) was added dropwise over 1 hr at 0° C. A white precipitate formed. The resulting suspension was stirred for an additional 20 min at 0° C. Then a solution of benzyl alcohol (464 µL, 4.5 mmol, 2.2 eq.) with anhydrous pyridine (478 µL, 5.92 mmol, 2.9 eq.) in anhydrous tetrahydrofuran (3.0 mL) was added at 0° C. The reaction mixture was stirred at room temperature overnight followed by filtration through a fritted glass funnel, and washing with ethyl acetate (2×5 mL). The combined organic layers were evaporated under reduced pressure. The residue was diluted with ethyl acetate (50 mL), and washed with 10% NaHSO$_4$ (20 mL), water (2×10 mL), sat NaHCO$_3$ (20 mL), water (20 mL) and brine (10 mL). The organic layers was dried over Na$_2$SO$_4$ and evaporated to dryness. The crude product was purified by flash chromatography eluting with EtOAc-toluene (10:90) to afford the desired compound methyl(S)-methyl-2-(bis(benzyloxy)phosphoryloxy)-3-methylbutanoate, compound 18 (35 mg, 0.089 mmol, 4.3% yield over two steps). $^1$H NMR (300 MHz, CDCl$_3$): consistent with proposed structure. MS: m/z=393.0 (M+1).

Example 19

(S)-methyl 2-(bis(benzyloxy)phosphoryloxy)-3-methylbutanoate

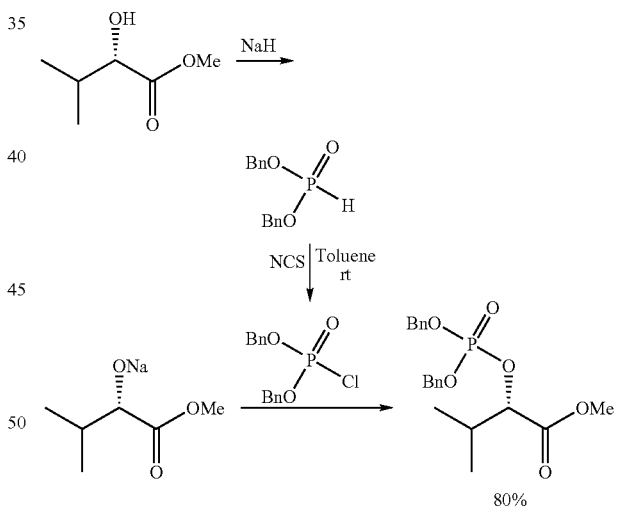

Step 1: Dibenzyl Phosphoryl Chloride

To a flame-dried 50 mL flask was added chlorosuccinimide (757 mg, 5.67 mmol), anhydrous toluene (15.0 mL) and dibenzyl phosphite (1.26 mL, 5.67 mmol). The resulting mixture was stirred at rt under N$_2$ for 3 hrs. The mixture was filtered through a dry fritted funnel in an anhydrous atmosphere and the filtrate was concentrated under reduced pressure. The crude product was used in the subsequent reaction without any purification.

Step 2: (S)-methyl 2-(bis(benzyloxy)phosphoryloxy)-3-methylbutanoate

To a dry 50 mL flask was added NaH (with mineral oil, 60%, 265 mg, 5.67 mmol). The NaH was washed with anhydrous hexanes (2×5 mL) to remove the mineral oil followed by the addition of anhydrous $CH_2Cl_2$ (15 mL). The mixture was cooled in dry ice-acetonitrile bath for 20 min. Then the solution of methyl(S)-2-hydroxy-3-methylbutyrate (681 mg, 5.15 mmol) in anhydrous $CH_2Cl_2$ (8 mL) was added dropwise at −40° C. over 10 min. After the resulting mixture was stirred for 10 min, the fresh reagent, dibenzyl phosphoryl chloride (prepared in step 1), in $CH_2Cl_2$ (5 mL) was added dropwise at −40° C. over 10 min. The mixture was stirred at the same temperature for 1 hr. Ethyl acetate (150 mL) was added to dilute the reaction mixture, which was washed with water (2×30 mL), brine (2×30 mL), and dried over $Na_2SO_4$. After concentration under reduced pressure, the crude was purified by flash chromatography eluting with $EtOAc-CH_2Cl_2$ (4:96 to 6:94)) to afford the desired compound methyl(S)-methyl-2-(bis(benzyloxy)phosphoryloxy)-3-methylbutanoate, 19 (1.619 g, 4.13 mmol, 80% yield). $^1H$ NMR (300 MHz, $CDCl_3$): consistent with proposed structure. MS: m/z=393.0 (M+1).

Example 20

(S)-2-(bis(benzyloxy)phosphoryloxy)-3-methylbutanoic Acid

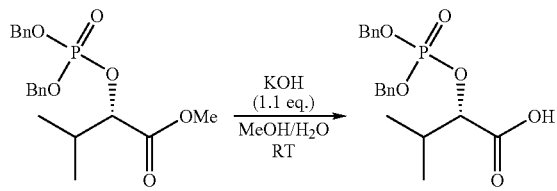

To a 50 mL flask containing (S)-methyl2-(bis(benzyloxy)phosphoryloxy)-3-methylbutanoate (699 mg, 1.78 mmol, 1.0 eq.) (prepared as in Example 18 or 19) was added methanol (9.2 mL). All starting material dissolved. Then a solution of potassium hydroxide in water (1 N, 3.56 mL, 3.56 mmol, 2.0 eq.) was added at ice-bath temperature. The resulting mixture was stirred at room temperature for 40 hrs. The reaction was monitored by LC-MS, and almost no starting remained. The reaction mixture was diluted with water (15 mL) and neutralized by hydrochloric acid (1 N, 3.6 mL, 3.6 mmol, 2.02 eq.) to reach pH 3 at 0° C. which was extracted by ethyl acetate (3×30 mL). The combined organic phase was washed with water (30 mL), brine (30 mL), and dried over $Na_2SO_4$ and concentrated under reduced pressure to afford crude compound 20, (S)-2-(bis(benzyloxy)phosphoryloxy)-3-methylbutanoic acid (650 mg) which was used directly in the next step without further purification. MS: m/z=379.0 (M+1).

Example 21

Coupling of the Diazonamide Core with the Phosphate-Containing Side Chain

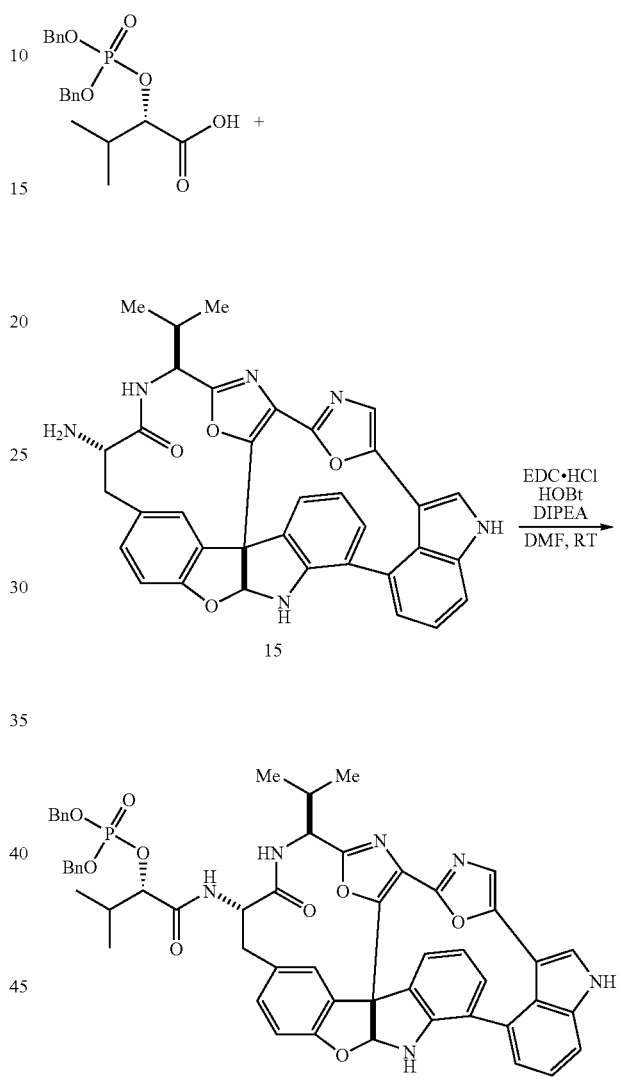

To a dry 50 mL flask containing (S)-2-(bis(benzyloxy)phosphoryloxy)-3-methylbutanoic acid (435 mg, 1.15 mmol, 1.2 eq.) was added compound 15 (571 mg, 0.96 mmol, 1.0 eq.), dimethylformamide (10 mL) and hydroxybenzotriazole (143 mg, 1.056 mmol, 1.1 eq.). After all solid dissolved, EDC.HCl (202 mg, 1.056 mmol, 1.1 eq.) were added. The resulting mixture was stirred at rt for 48 hrs. The reaction mixture was diluted with ethyl acetate (100 mL), washed with water (30 mL), 10% $NaHSO_4$ (30 mL), water (30 mL), sat $NaHCO_3$ (30 mL), water (2×30 mL), and brine (30 mL). The organic layers were dried over $Na_2SO_4$ and concentrated. The crude product was purified by flash chromatography eluting with EtOAc-toluene (70:30 to 80:20) to afford the desired compound 21 (540 mg, 0.564 mmol, 59% yield). MS: m/z=957.2 (M+1).

Example 22

Deprotection of the Di-Benzyl Ester

Preparation of Free Acid

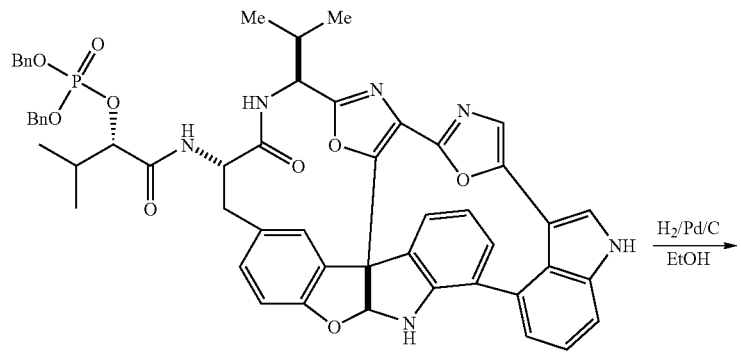

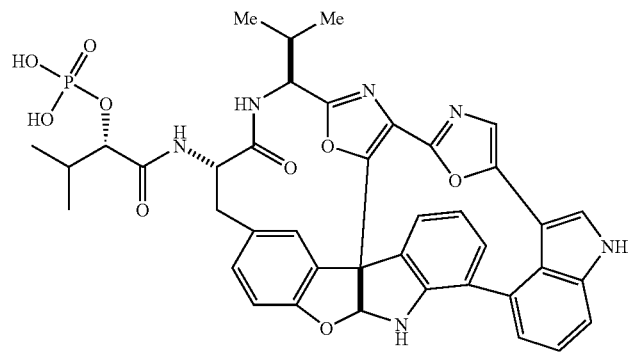

To a 15 mL flask containing the di-benzyl ester compound 21 above (23 mg, 0.024 mmol, 1.0 eq.) was added ethanol (2 mL). All solid dissolved. Pd/C (10%, 8.0 mg, 0.0075 mmol, 0.3 eq.) was added under $N_2$. The mixture was purged with $H_2$ four times. Then a hydrogen-filled balloon was used to saturate the reaction system. After 2 hrs stirring at room temperature, no starting material remained, and the reaction was stopped. The mixture was filtered through a pad of Celite, and the Pd/C cake was washed with ethanol (4×1 mL). The combined filtrate was evaporated under reduced pressure and dried under high vacuum. The residue was dissolved in deionized water (20 mL) and the solution was divided to two parts of equal volume. One part was filtered through a 0.45 μm nylon filter and the filtrate (pH=5-6) was lyophilized to afford 8 mg of compound 22 as the free acid. $^1$H NMR (500 MHz, $CD_3OD$): consistent with proposed structure. MS: m/z=777.2 (M+1). The other part was converted to the mono sodium salt, as described in Example 23.

Example 23

Conversion of Free Acid to Monosodium Salt

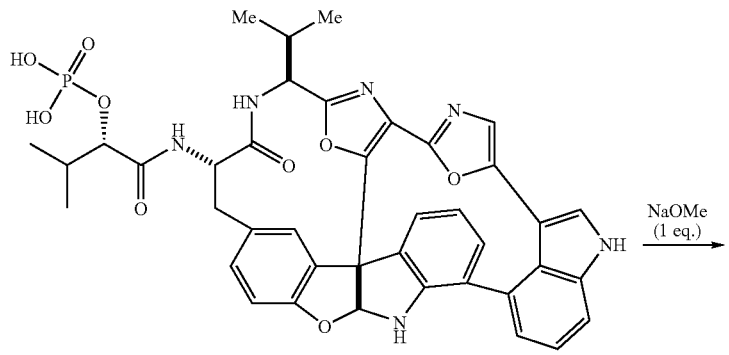

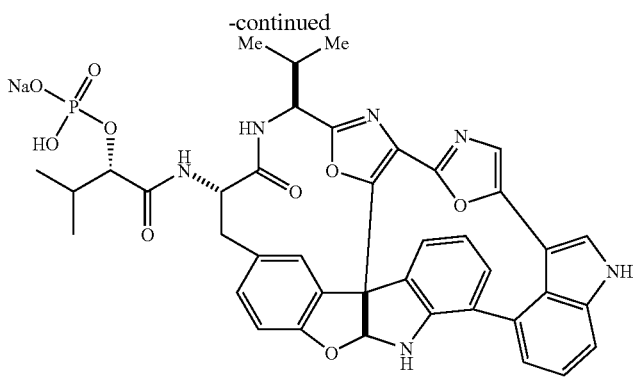

The second part of the product of Example 22 was neutralized with a solution of NaOMe in MeOH (0.5 M, 24 μL, 0.012 mmol, 1.0 eq.). The resulting aqueous solution was filtered through a 0.45 μm nylon filter and the filtrate lyophilized to afford 8 mg of the mono-sodium salt, compound 23. The combined yield of this deprotection reaction was 81%. MS: m/z=777.2 (M+1). 5 mg of the mono-sodium salt was shown to dissolve in 1 mL of de-ionized water.

Example 24

Methyl(S)-2-benzyloxy-3-methylbutanoate

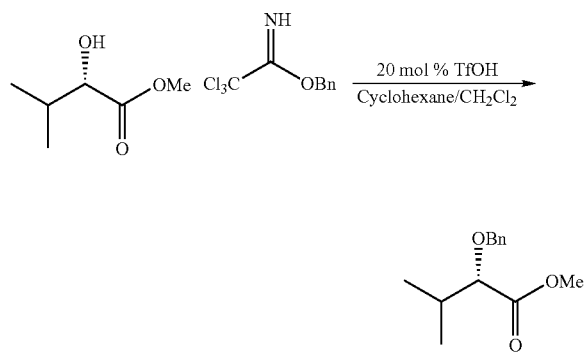

To a flame-dried 50 mL flask was added methyl(S)-2-hydroxy-3-methylbutyrate (330 mg, 2.5 mmol), anhydrous $CH_2Cl_2$ (1.5 mL), cyclohexane (3 mL). The reaction flask was cooled to 0° C., and benzyl 2,2,2-trichloroacetimidate (0.464 mL, 2.5 mmol) was added with stirring. To the resulting solution was added trifluoromethanesulfonic acid (0.044 mL, 0.5 mmol). After addition was completed, the reaction was warmed to room temperature and was stirred for 17 hrs. The reaction was monitored by $^1$H NMR, and most of SM was consumed. The reaction mixture was filtered, and collected solid was rinsed with cyclohexane (2×10 mL). The filtrate was washed with saturated $NaHCO_3$ (5 mL), water (2×5 ml), brine (5 mL), dried over $Na_2SO_4$ and concentrated under reduced pressure. The crude oil was purified by flash chromatography eluting with EtOAc-Hexanes (0.5:99.5) to afford the desired compound methyl (S)-methyl-2-benzyloxy-3-methylbutanoate (319 mg, 1.44 mmol, 57% yield). $^1$H NMR (300 MHz, $CDCl_3$): consistent with proposed structure.

Example 25

(S)-2-benzyloxy-3-methylbutanoic Acid

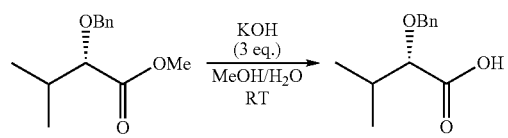

To a 50 mL flask containing methyl(S)-2-benzyloxy-3-methylbutanoate (309 mg, 1.39 mmol, 1.0 eq.) (prepared as in Example 24) was added methanol (9 mL). All starting material dissolved. Then a solution of potassium hydroxide in water (1 N, 4.2 mL, 4.2 mmol, 3.0 eq.) was added at ice-water bath temperature. The resulting mixture was stirred at room temperature for 3 days. The reaction was monitored by LC-MS, and almost no SM remained. The reaction mixture was diluted with water (15 mL) and most of methanol was removed under reduced pressure. The aqueous layer was extracted by ether (2×10 mL), and neutralized by hydrochloric acid (1 N, 4.2 mL, 4.2 mmol, 3.0 eq.) to reach pH 3 at 0° C. The cloudy aqueous layer was extracted by ether (5×20 mL). The combined organic phase was washed with brine (30 mL), dried over $Na_2SO_4$ and concentrated under reduced pressure to afford crude product (S)-2-benzyloxy-3-methylbutanoic acid (260 mg, 1.25 mmol, 90%). $^1$H NMR (300 MHz, $CDCl_3$): consistent with proposed structure.

Example 26

Coupling of the Diazonamide Core with (S)-2-benzyloxy-3-methylbutanoic Acid

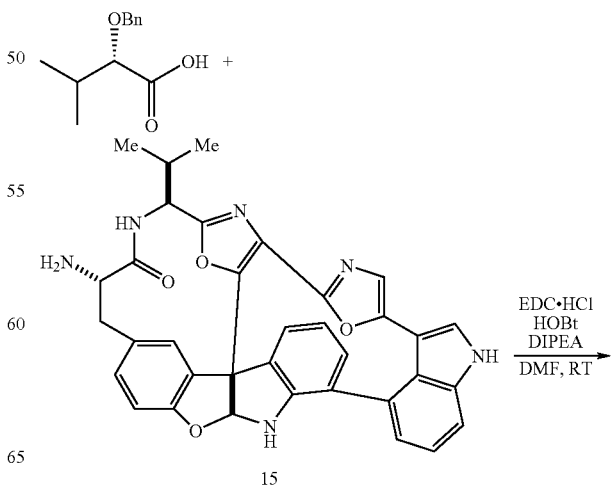

15

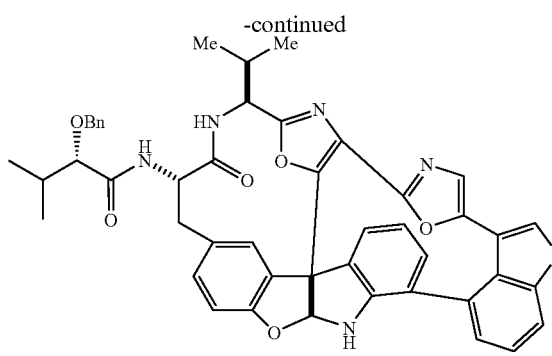

To a dry 15 mL flask containing (S)-2-benzyloxy-3-methylbutanoic acid (181 mg, 0.872 mmol, 1.3 eq.) was added compound 15 (400 mg, 0.670 mmol, 1.0 eq.), dimethylformamide (5 mL) and hydroxybenzotriazole (100 mg, 0.737 mmol, 1.1 eq.). After all solid dissolved, EDC.HCl (141 mg, 0.737 mmol, 1.1 eq.) were added followed by the addition of DIPEA (0.117 mL, 0.670 mmol, 1.0 eq.). The resulting mixture was stirred at rt for 24 hrs. The reaction mixture was diluted with ethyl acetate (70 mL), washed with water (20 mL), 10% $NaHSO_4$ (20 mL), water (20 mL), sat $NaHCO_3$ (20 mL), water (2×20 mL), and brine (20 mL). The organic layers were dried over $Na_2SO_4$ and concentrated. The crude product was purified by flash chromatography eluting with EtOAc-$CH_2Cl_2$ (30:70 to 45:55) to afford the desired compound 26 (370 mg, 0.47 mmol, 70% yield). MS: m/z=787.2 (M+1).

Example 27

Phosphorylation of Indole Ring

Step 1: Dibenzyl Phosphoryl Chloride

To a flame-dried 50 mL flask was added chlorosuccinimide (757 mg, 5.67 mmol), anhydrous toluene (15.0 mL) and dibenzyl phosphite (1.26 mL, 5.67 mmol). The resulting mixture was stirred at rt under $N_2$ for 3 hrs. The mixture was filtered through a dry fritted funnel in an anhydrous atmosphere and the filtrate was concentrated under reduced pressure. The crude product was used in the subsequent reaction without any purification.

Step 2: Phosphorylation of the Indole Ring

To a dry 100 mL flask containing compound 26 (370 mg, 0.470 mmol, 1.0 eq.) was added anhydrous THF (50 mL). All solid dissolved. The solution was cooled in acetone-dry ice bath for 30 min. The reagent NaHMDS in THF (1 M, 1.081 mL, 1.081 mmol, 2.3 eq.) was added dropwise at −78° C. over 5 min. After the resulting mixture was stirred for 10 min at −78° C., the fresh reagent, dibenzyl phosphoryl chloride prepared in step 1, in $CH_2Cl_2$ (0.167 M, 6.9 mL, 1.15 mmol, 2.4 eq.) was added dropwise at −78° C. over 10 min. The mixture was stirred at the same temperature for 30 min. The reaction was monitored by LC-MS. Almost no SM remained and about 5% of over-phosphated product was formed. The cool reaction mixture was poured to water (100 mL), and the desired product was extracted by EtOAc (2×100 ml), washed with water (3×50 ml), brine (50 mL), and dried over $Na_2SO_4$. After concentration under reduced pressure, the crude was purified by flash chromatography eluting with EtOAc-$CH_2Cl_2$ (30:60) to afford the desired compound 27 (354 mg, 0.338 mmol, 72% yield). MS: m/z=1047.2 (M+1).

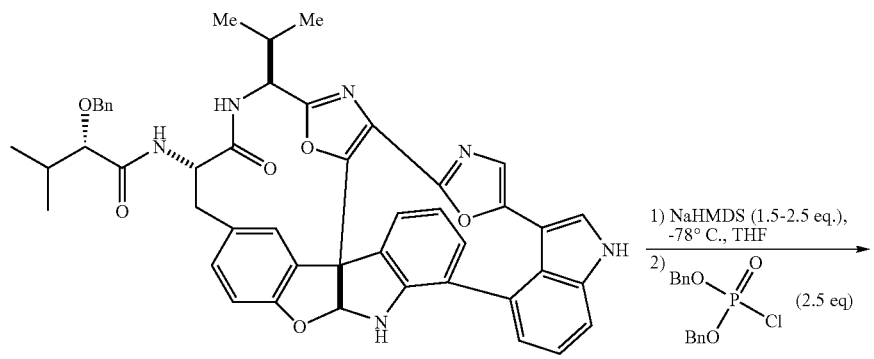

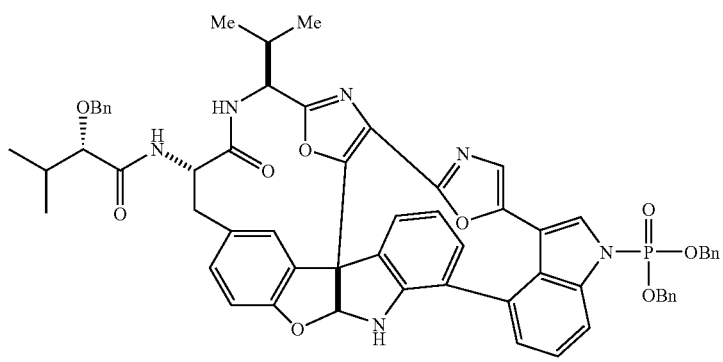

Example 28

Deprotection of the Di-Benzyl Phosphate

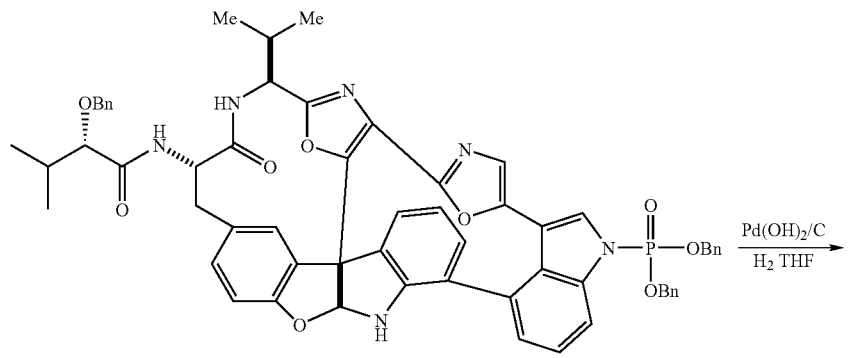

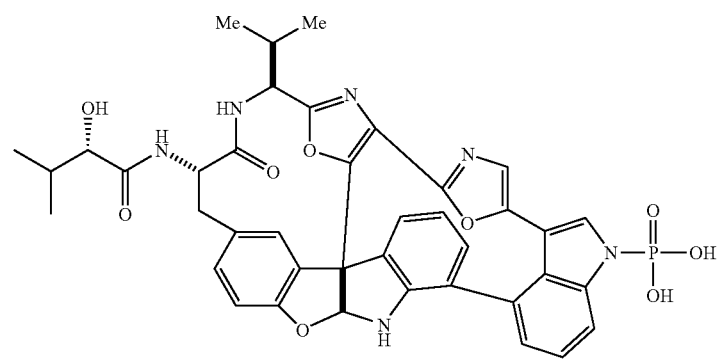

To a 100 mL flask containing the di-benzyl phosphate compound 27 (334 mg, 0.319 mmol, 1.0 eq.) was added THF (35 mL). All solid dissolved. Pd(OH)$_2$/C (20%, 223 mg, 0.319 mmol, 1.0 eq.) was added under N$_2$. The mixture was purged with H$_2$ four times. Then a hydrogen-filled balloon was used to saturate the reaction system. After 8 hrs stirring at room temperature, almost no starting material remained, and the reaction was stopped. The mixture was filtered through a pad of Celite, and the Pd(OH)$_2$/C cake was washed with THF (4×10 mL). The combined filtrate was evaporated under reduced pressure and dried under high vacuum. De-ionized water (100 mL) was added and the mixture was sonicated for 10 min, which was filtered through a syringe filter (0.45 μm). The filtrate (pH=5-6) was lyophilized to afford the desired compound 28 (125 mg, 0.161 mmol, 50% yield). $^1$H NMR (400 MHz, CD$_3$OD): consistent with proposed structure for the phosphoric acid derivative. MS: m/z=777.0 (M+1).

Example 29

Phosphamide Formation

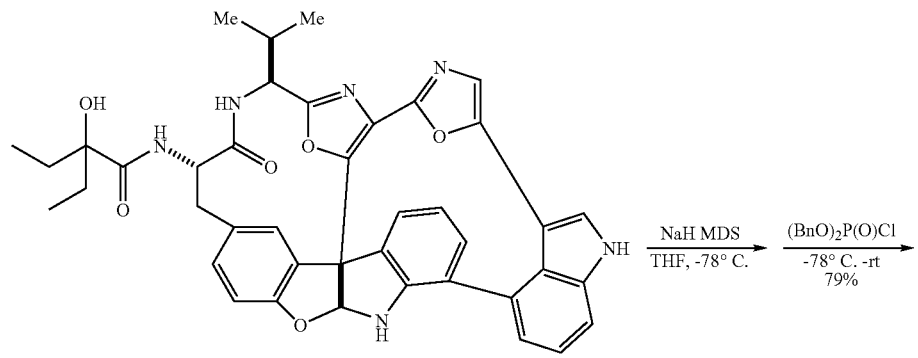

-continued

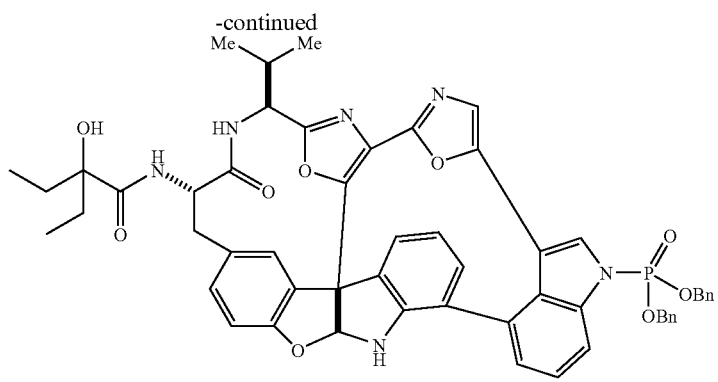

To a 200 mL dry flask containing the indole starting material (prepared by a modification of Example 35) (324 mg, 0.456 mmol) was added anhydrous tetrahydrofuran (60 mL). This solution was cooled in acetone/dry ice bath for 20 min. The solution of sodium hexamethyldisilazide in tetrahydrofuran (1 M, 684 uL, 0.684 mmol) was added to the solution above dropwise under $N_2$ over 5 min. The yellow reaction mixture was stirred at −78° C. for 30 min. Then a solution of freshly prepared $(BnO)_2P(O)Cl$ in $CH_2Cl_2$ (0.184 M, 3.7 mL, 0.684 mmol) was added dropwise. After stirring for 1 hour at −78° C., the mixture was quenched by phosphate buffer (pH=6.9, 30 mL) followed by extraction with ethyl acetate (2×100 mL). The organic phase was washed with brine (2×50 mL), and dried over $Na_2SO_4$. After concentration, the crude was purified via PTLC (7% $MeOH/CH_2Cl_2$) to afford the desired compound 29 (350 mg, 79% yield). The structure was confirmed by LCMS [m/z=970.8 (M+H$^+$)].

Example 30

Deprotection of Benzyl Group of the Phosphamide

To a 100 mL round-bottom flask containing the phosphamide from Example 29 (350 mg, 0.360 mmol) was added MeOH (15 mL). The flask was purged with $N_2$ flow for 10 min followed by addition of Pd/C (10%, 38 mg, 0.036 mmol) under $N_2$. An hydrogen balloon was added and the flask was purged with hydrogen 4 times. Then the hydrogen balloon was left open to the reaction system. After 90 min. stirring no starting material remained by LC-MS. The reaction was stopped. The reaction mixture was filtered through a pad of Celite and the black cake was washed with MeOH (4×2 mL). The combined filtrate was used in next step. The structure of compound 30 was confirmed by LC-MS [m/z=790.7 (M+H$^+$)].

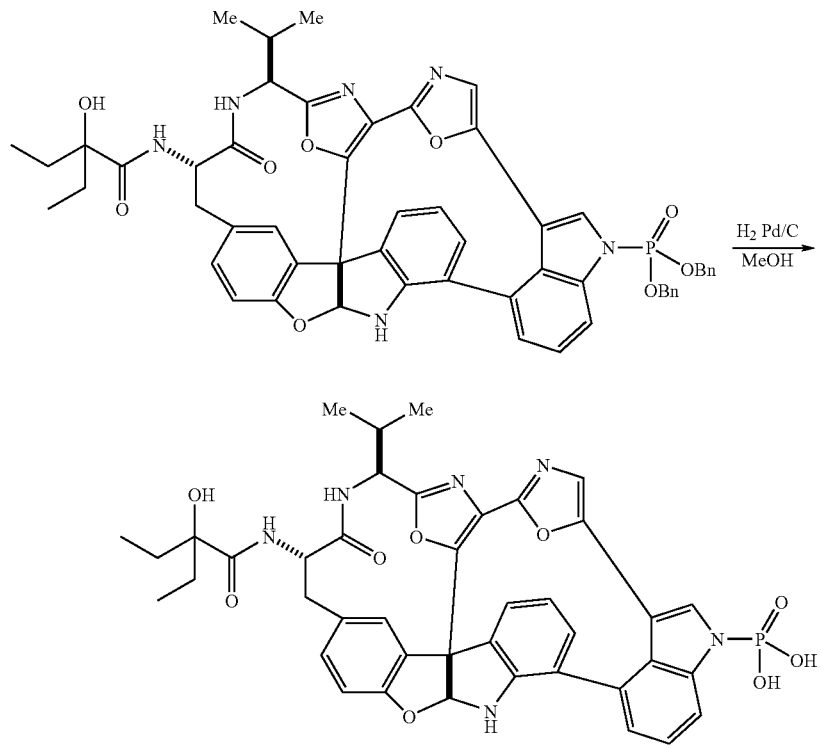

Example 31

Formation of the Mono-Sodium Salt

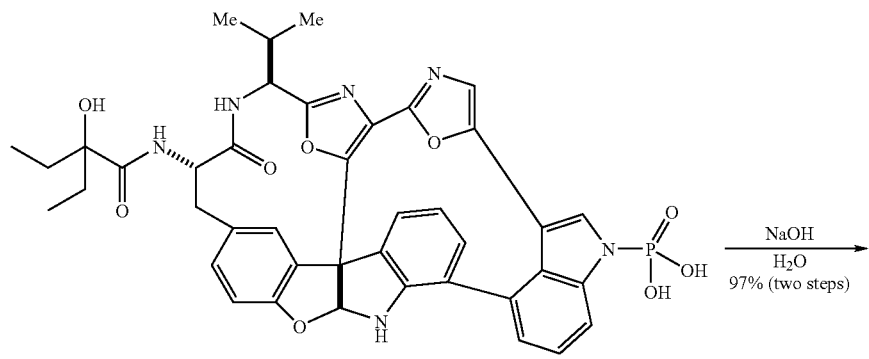

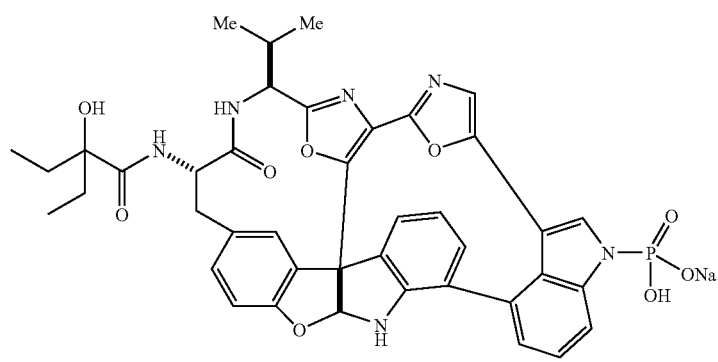

To the combined filtration above was added a stock solution of NaOH in water (14.4 mg/mL, 1 mL, 0.360 mmol). The resulting solution was concentrated to remove most of MeOH at room temperature. Then the residue was diluted with DI water (100 mL). This solution was filtered through a syringe filter (0.45 um) to remove tiny particles. The filtrate was lyophilized to afford the desired compound monosodium salt, 31 (285 mg, 97% yield for two steps). The solubility of the monosodium salt in water is 20 mg/mL, and this aqueous solution is stable for more than 48 hours at room temperature.

Example 32

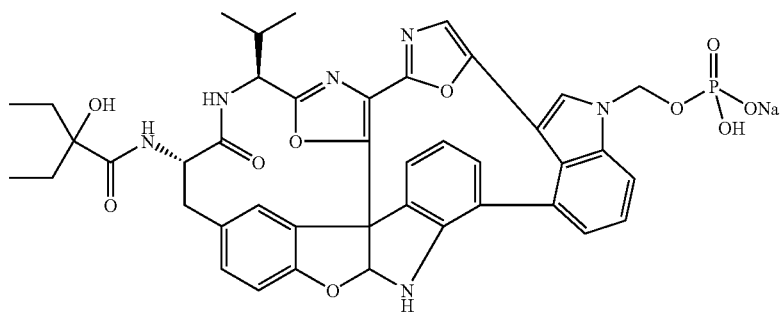

Compound 32 is prepared according to the route provided in Scheme 7.

Example 33

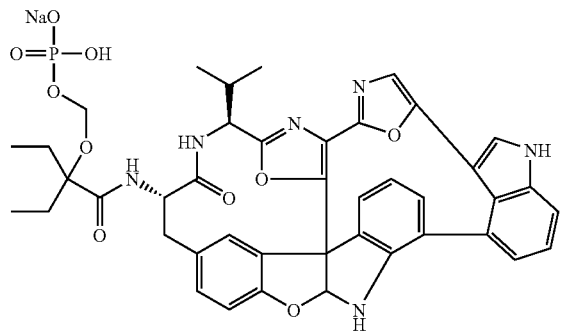

Compound 33 is prepared according to a modification of the route provided in Example 21, by reaction of the diazonamide core with an appropriately functionalized 2-ethyl-2-hydroxybutyric acid derivative.

Example 34

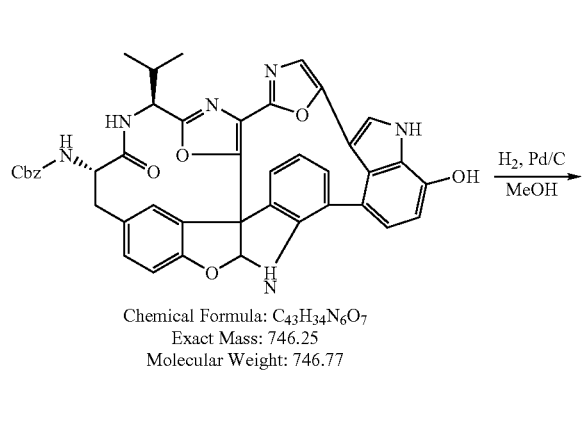

Chemical Formula: $C_{43}H_{34}N_6O_7$
Exact Mass: 746.25
Molecular Weight: 746.77

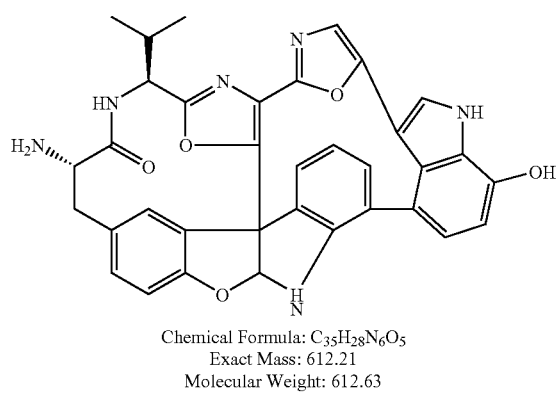

Chemical Formula: $C_{35}H_{28}N_6O_5$
Exact Mass: 612.21
Molecular Weight: 612.63

To a 50 mL flask containing compound 13 (153 mg, 0.21 mmol) and Pd/C (10%, 30 mg) was added methanol (5 mL) and TEA (86 μL, 0.62 mmol, 3.0 eq) under $N_2H_2$ was purged via a $H_2$ balloon and the mixture was stirred at room temperature. After 3 h, released $H_2$, the reaction mixture was filtered through a 0.45 μL filter. The filtrate was concentrated and the residue was used directly in next step without further purification. The structure of compound 34 was confirmed by LC-MS.

Example 35

Coupling with 2-ethyl-2-hydroxybutyric Acid

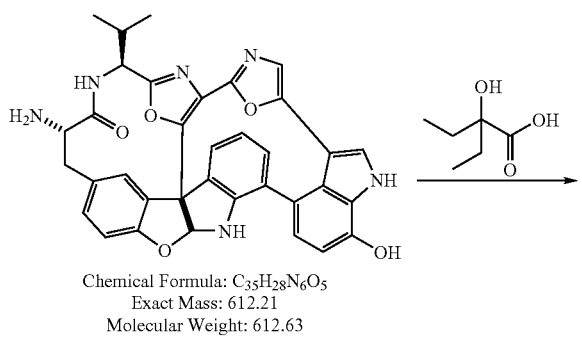

Chemical Formula: $C_{35}H_{28}N_6O_5$
Exact Mass: 612.21
Molecular Weight: 612.63

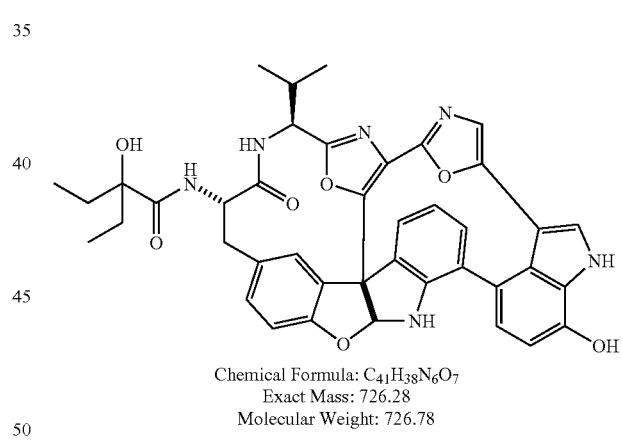

Chemical Formula: $C_{41}H_{38}N_6O_7$
Exact Mass: 726.28
Molecular Weight: 726.78

To a solution of starting material, compound 34 (84 mg, 0.14 mmol), 2-ethyl-2-hydroxybutyric acid (21.8 mg, 0.165 mmol, 1.2 eq) and HOBt (22.2 mg, 0.165 mmol, 1.2 eq) in DMF (3 mL) was added EDIPA (36 μL, 0.206 mmol, 1.5 eq), followed by added EDC (31.5 mg, 0.165 mmol, 1.2 eq) at room temperature. After stirred for 12 h, the reaction solution was diluted with EtOAc (100 mL), and washed with 1N HCl (20 mL), water (20 mL), saturated $NaHCO_3$ (20 mL) and brine (20 mL). Dried over $Na_2SO_4$, the solution was concentrated and the crude was purified by flash chromatography eluting with $MeOH/CH_2Cl_2$ gradient (5/95) to afford desired compound 35. The structure was confirmed by LC-MS.

Example 36

Phosphate Formation

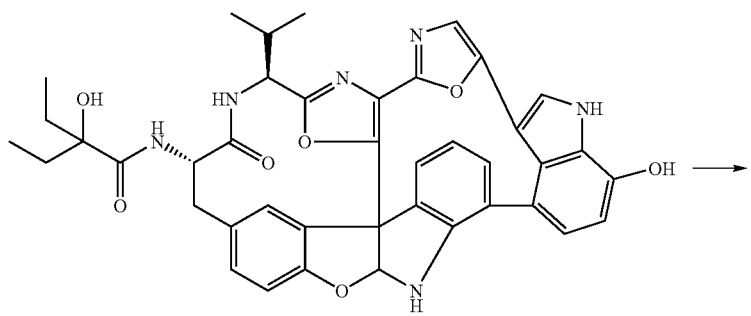

Chemical Formula: C$_{41}$H$_{38}$N$_6$O$_7$
Exact Mass: 726.28
Molecular Weight: 726.78

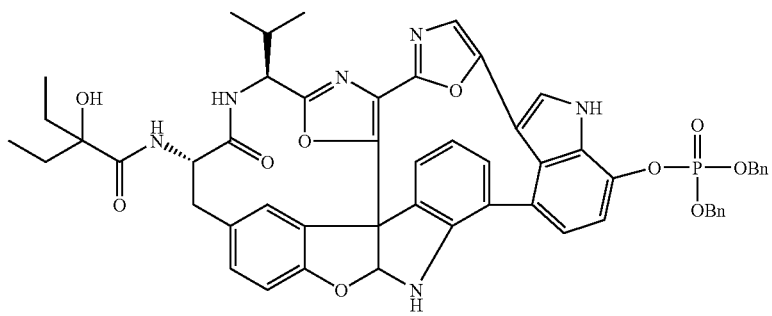

Chemical Formula: C$_{55}$H$_{51}$N$_6$O$_{10}$P
Exact Mass: 986.34
Molecular Weight: 987.00

To a solution of the compound 35 (29 mg, 0.041 mmol), DMAP (0.5 mg, 0.004 mmol, 0.1 eq) in MeCN (3 mL) at −30° C. under N$_2$ protection was added CCl$_4$ 150 mL, followed by EDIPA (14 μL, 0.082 mmol, 2 eq). After 5 min, dibenzylphophite (11 μL, 0.049 mmol, 1.2 eq) was added and the reaction was stirred at −15 to −25° C. for 45 min. Removed ice-acetone-dry ice bath, allowed reaction mixture stirred at room temperature for 10 min. Quenched with 0.5 M KH$_2$PO$_4$ solution (10 mL), and the product was extracted with EtOAc. After dried under Na$_2$SO$_4$, filtered then concentrated. The pure desired compound 36 was obtained after column. The structure confirmed by LC-MS.

Example 37

Deprotection of Benzyl Group of the Phosphate

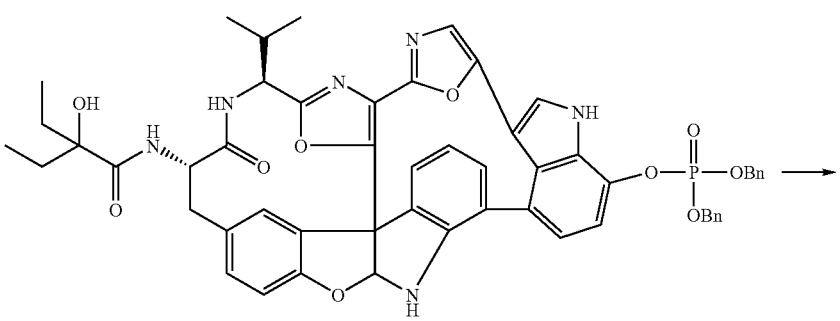

Chemical Formula: C$_{55}$H$_{51}$N$_6$O$_{10}$P
Exact Mass: 986.34
Molecular Weight: 987.00

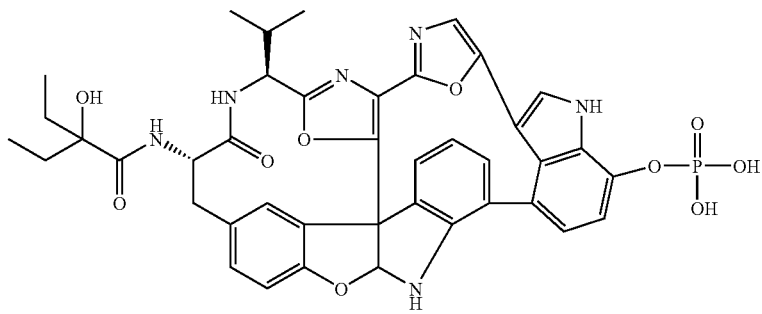

Chemical Formula: $C_{41}H_{39}N_6O_{10}P$
Exact Mass: 806.25
Molecular Weight: 806.76

To a 50 mL flask containing starting material compound 36 (28 mg, 0.029 mmol) and Pd/C (10%, 6 mg), was added methanol (5 mL) under $N_2H_2$ was purged via a $H_2$ balloon and the mixture was stirred at room temperature. After 2 h, released $H_2$, the reaction mixture was filtered through a 0.45 μL filter. The filtrate was concentrated and the desired compound 37 was obtained. The structure was confirmed by LC-MS.

Example 38

Formation of Sodium Salt

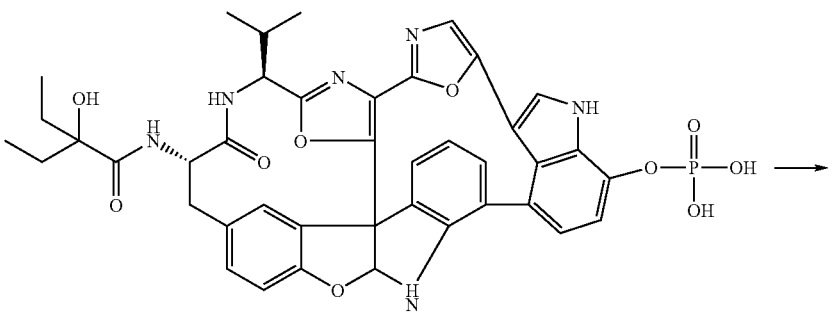

Chemical Formula: $C_{41}H_{39}N_6O_{10}P$
Exact Mass: 806.25
Molecular Weight: 806.76

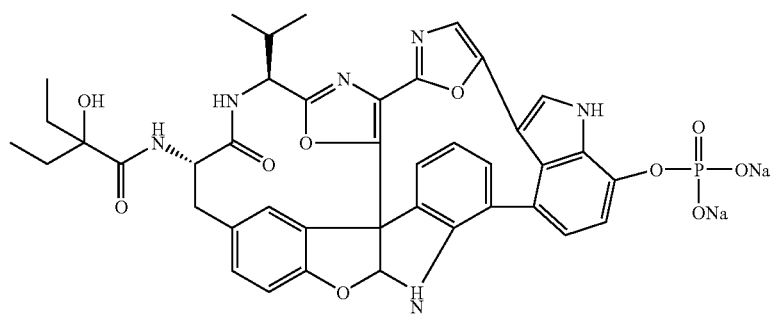

Chemical Formula: $C_{41}H_{37}N_6Na_2O_{10}P$
Exact Mass: 850.21
Molecular Weight: 850.72

To a solution of compound 37 (16.8 mg, 0.021 mmol) in methanol (2 mL) was added MeONa (0.5 m solution in methanol, 84 μL, 2 eq) at room temperature under $N_2$. After stirred 30 min, solvent was removed. Added water 3 mL, and the solution was filtered through a 0.45 μL filter. Dried filtrate under vacuum, the desired compound 38 was obtained. The structure was confirmed by LC-MS.

Example 39

Xenograft Tumor Model

Compound 22 (prepared according to Example 22) and Compound 28 (prepared according to Example 28) were tested in a HCC461 human NSCLC xenograft tumor model in mice.

Protocol:
Preparation of Tumor Cells
1. Hcc461 cells were cultured in complete RPMI medium and excluded any contamination
2. When cells are 70-80% confluent, medium was removed and cells were washed with serum free media, trypsinized, harvested and washed with serum free media for three times by centrifuge. After final washing, cells were counted and mixed with matrigel at 1:1 ration in volume. Cells were suspended in a volume that 200 PI contains required number of cells per injection.

Preparation of Mice
1. Mice should be 4-6 weeks old.
2. Allow 3-5 days acclimatization period after mice have arrived.

Preparation of the Injection
1. Clean and sterilize the inoculation area of the mice with iodine solutions and ethanol.
2. Take cells with 1-cc syringe.
3. Inject cells ($1 \times 10^7$) with 27 gauge needles subcutaneously (s.c.) into the lower flank of the mice.
4. Therapy was started after 1 week when the tumors have reached an average volume of ~250 $mm^3$.
5. Tumor diameters are measured with digital calipers, and the tumor volume in $mm^3$ is calculated by the formula:

Volume=(width)$^2$×length/2

Treatment
1. Compound 22 and Compound 28 were dissolved in water at concentration of 5 mg/ml and diluted to working solution with D5W before injection. Compound 16 was administered at 20 mg/kg in a mixture of 5% ethanol-5% cremaphor-90% saline.
2. Each tumor bearing mouse was injected with Compound 22 at 20 mg/kg, Compound 28 at 20 mg/kg or at 10 mg/kg, or Compound 16 at 20 mg/kg via tail vein and continually injected with the same method for a total of 6 times, on days 7, 9, 11, 14, 16, and 18 post tumor-cell injection.

Results

The activity of Compound 22 at 20 mpk versus Compound 16 at 20 mpk in HCC461 NSCLC mouse xenograft model is provided in FIG. 1.

The activity of Compound 28 at 20 mpk and at 10 mpk versus Compound 16 at 20 mpk in HCC461 NSCLC mouse xenograft model is provided in FIG. 2.

Example 40

Exemplary Embodiments of the Invention

The following embodiments are offered to illustrate but not to limit the invention.

1. A compound of Formula I:

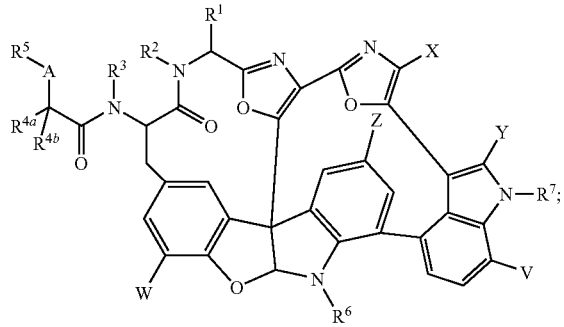

or a pharmaceutically acceptable salt, ester or conjugate thereof;
wherein $R^1$ is H, or C1-C8 alkyl, C2-C8 alkenyl, C2-C8 alkynyl, or a heteroform of one of these, C6-C12 aryl, C7-C20 arylalkyl, C5-C12 heteroaryl, or C6-C20 heteroarylalkyl, each of which may be optionally substituted;
$R^2$ is H or C1-C4 alkyl; or
$R^1$ and $R^2$ may be taken together with the atoms to which they are attached to form an optionally substituted 5- to 7-membered azacyclic ring, optionally containing an additional heteroatom selected from N, O and S as a ring member;
$R^3$ is H or C1-C4 alkyl;
each of $R^{4a}$ and $R^{4b}$ is independently H, or C1-C8 alkyl, C2-C8 alkenyl, C2-C8 alkynyl, or a heteroform of one of these, C6-C12 aryl, C7-C20 arylalkyl, C5-C12 heteroaryl, or C5-C20 heteroarylalkyl, each of which may be optionally substituted; or
$R^{4a}$ and $R^{4b}$ may be taken together with the carbon to which they are attached to form a C3-C8 cycloalkyl or a C3-C8 heterocyclyl ring, each of which may be optionally substituted;
$R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, alkylsulfonyl, arylsulfonyl, trialkylsilyl, or alkoxycarbonyl, each of which may be optionally substituted;
V is H, halo, or $OR^{10}$, where $R^{10}$ is H, C1-C6 acyl, C6-C12 aroyl, alkylsulfonyl, arylsulfonyl, —$PO_3H_2$, —$SO_3H$, —$C(O)CR^8{}_2NH_2$, —C(O)-L-COOH, or -L-O—$PO_3H_2$;
each of $R^5$ and $R^7$ is independently H, or C1-C8 alkyl, C1-C8 heteroalkyl, C6-C14 arylalkyl, C6-C14 heteroarylalkyl, C1-C6 acyl, C6-C12 aroyl, alkylsulfonyl, arylsulfonyl, trialkylsilyl, or alkoxycarbonyl, each of which may be optionally substituted; or —$PO_3H_2$, —$SO_3H$, —$C(O)CR^8{}_2NH_2$, —C(O)-L-COOH, or -L-O—$PO_3H_2$;
each $R^8$ is independently H or C1-C8 alkyl, C2-C8 alkenyl, C2-C8 alkynyl, or a heteroform of one of these, C6-C12 aryl, C7-C20 arylalkyl, C5-C12 heteroaryl, or C6-C20 heteroarylalkyl, each of which may be optionally substituted; and
L is a C1-C4 alkylene or C2-C4 alkenylene linker;
provided at least one of $R^5$, $R^7$ and $R^{10}$ is —$PO_3H_2$, —$SO_3H$, —$C(O)CR^8{}_2NH_2$, —C(O)-L-COOH, or -L-O—$PO_3H_2$;
A is O or NR, where R is hydrogen or C1-4 alkyl;
each of W and Z is independently H, halo, OH or C1-C4 alkoxy; and
each of X and Y is independently H, halo, C1-C8 alkyl, C2-C8 alkenyl, C2-C8 alkynyl, C6-C12 aryl, or C5-C12 heteroaryl, each of which may be optionally substituted, or COOR$^9$ or CONR$^9_2$, where each R$^9$ is independently H or C1-C4 alkyl.

2. The compound of embodiment 1, having the Formula II, III-A, III-B, IV-A or IV-B

II

III-A

III-B

IV-A

IV-B or a pharmaceutically acceptable salt, ester or conjugate thereof.

3. The compound of embodiment 1 or 2, wherein R$^1$ is a C1-C4 alkyl group.

4. The compound of embodiment 1, 2, or 3, wherein R$^2$ is H or methyl.

5. The compound of embodiment 1 or 2, wherein R$^1$ and R$^2$ are taken together with the atoms to which they are attached to form an optionally substituted 5- to 7-membered azacyclic ring, optionally containing an additional heteroatom selected from N, O and S as a ring member;

6. The compound of any one of embodiments 1 to 5, wherein R$^3$ is H.

7. The compound of any one of embodiments 1 to 6, wherein each of R$^{4a}$ and R$^{4b}$ is a C1-C4 alkyl.

8. The compound of any one of embodiments 1 to 7, wherein each of R$^{4a}$ and R$^{4b}$ is ethyl.

9. The compound of any one of embodiments 1 to 6, wherein at least one of R$^{4a}$ and R$^{4b}$ is H.

10. The compound of embodiment 9, wherein one of R$^{4a}$ and R$^{4b}$ is H, and the other is a C1-C4 alkyl.

11. The compound of any one of embodiments 1 to 6, 9 or 10, wherein one of R$^{4a}$ and R$^{4b}$ is H, and the other is isopropyl.

12. The compound of any one of embodiments 1 to 6, wherein R$^{4a}$ and R$^{4b}$ are taken together with the carbon to which they are attached to form a C3-C8 cycloalkyl or a C3-C8 heterocyclyl ring, each of which may be optionally substituted.

13. The compound of any one of embodiments 1 to 12, wherein A is O.

14. The compound of any one of embodiments 1 to 13, wherein R$^5$ is —PO$_3$H$_2$, or a salt or ester form thereof.

15. The compound of any one of embodiments 1 to 13, wherein R$^5$ is -L-O—PO$_3$H$_2$, or a salt or ester form thereof.

16. The compound of embodiment 15, wherein L is methylene linker.

17. The compound of any one of embodiments 1 to 13, wherein R$^5$ is —C(O)-L-COOH, or a salt or ester form thereof.

18. The compound of embodiment 17, wherein L is an ethylene or an ethenylene linker.

19. The compound of any one of embodiments 1 to 13, wherein R$^5$ is —SO$_3$H, or a salt or ester form thereof.

20. The compound of any one of embodiments 1 to 13, wherein R$^5$ is —C(O)CR$^8_2$NH$_2$, or a salt form thereof.

21. The compound of any one of embodiments 1 to 13, wherein R$^5$ is H or acetyl.

22. The compound of any one of embodiments 1 to 21, wherein R$^6$ is H.

23. The compound of any one of embodiments 1 to 22, wherein $R^7$ is H.

24. The compound of any one of embodiments 1 to 22, wherein $R^7$ is —$PO_3H_2$ or a salt or ester form thereof.

25. The compound of embodiment 24, wherein $R^5$ is H or acetyl.

26. The compound of embodiment 24, wherein $R^5$—$PO_3H_2$ or a salt or ester form thereof.

27. The compound of any one of embodiments 1 to 22, wherein $R^7$ is -L-O—$PO_3H_2$, or a salt or ester form thereof.

28. The compound of embodiment 27, wherein L is methylene linker.

29. The compound of any one of embodiments 1 to 22, wherein $R^7$ is —C(O)-L-COOH, or a salt or ester form thereof.

30. The compound of embodiment 29, wherein L is an ethylene or an ethenylene linker.

31. The compound of any one of embodiments 1 to 22, wherein $R^7$ is —$SO_3H$, or a salt or ester form thereof.

32. The compound of any one of embodiments 1 to 22, wherein $R^7$ is —$C(O)CR^8{}_2NH_2$, or a salt form thereof.

33. The compound of any one of embodiments 1 to 32, wherein V is H.

34. The compound of any one of embodiments 1 to 32, wherein V is $OR^{10}$.

35. The compound of embodiment 34, where $R^{10}$ is H or acetyl.

36. The compound of embodiment 34, where $R^{10}$ is —$PO_3H_2$, —$SO_3H$, —$C(O)CR^8{}_2NH_2$, —C(O)-L-COOH, or -L-O—$PO_3H_2$, or a salt or ester form thereof.

37. The compound of embodiment 36, where $R^{10}$ is —$PO_3H_2$ or a salt or ester form thereof.

38. The compound of any one of embodiments 1 to 37, wherein W is H.

39. The compound of any one of embodiments 1 to 38, wherein Z is H or halo.

40. The compound of any one of embodiments 1 to 39, wherein X is H, halo, COO $R^9$ or $CONR^9{}_2$, where each $R^9$ is independently H or C1-C4 alkyl.

41. The compound of any one of embodiments 1 to 40, wherein Y is H, halo, $COOR^9$ or $CONR^9{}_2$, where each $R^9$ is independently H or C1-C4 alkyl.

42. The compound of any one of embodiments 1 to 41, wherein at least one of X and Y is halo.

43. The compound of embodiment 42, wherein said halo is chloro.

44. The compound of embodiment 42, wherein each of X and Y is chloro.

45. A compound having the structure:

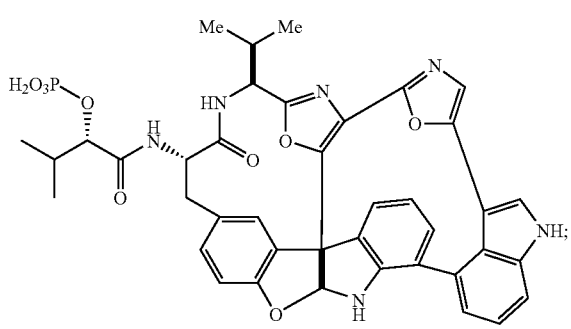

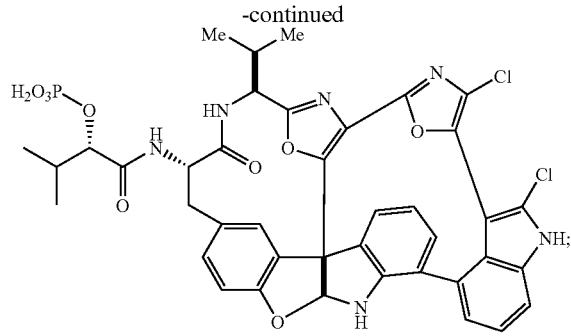

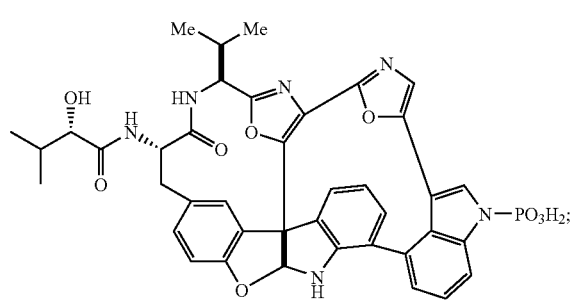

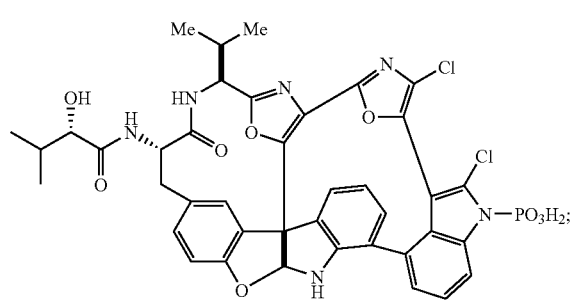

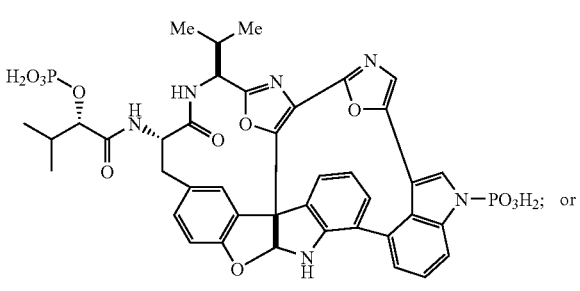

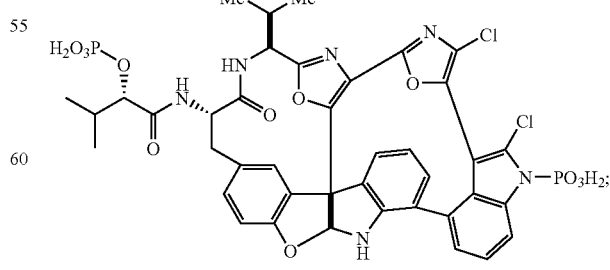

or a pharmaceutically acceptable salt, ester or conjugate thereof.

46. A compound having the structure:

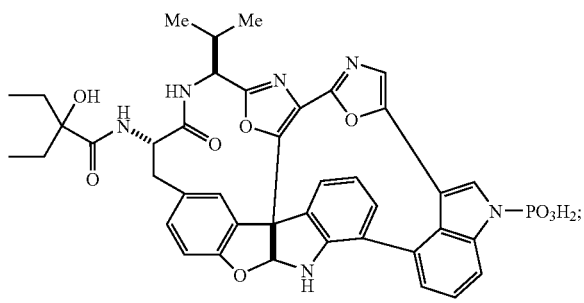

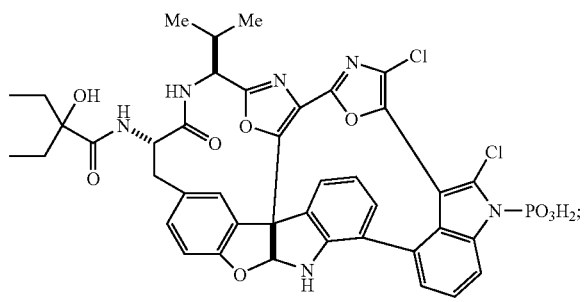

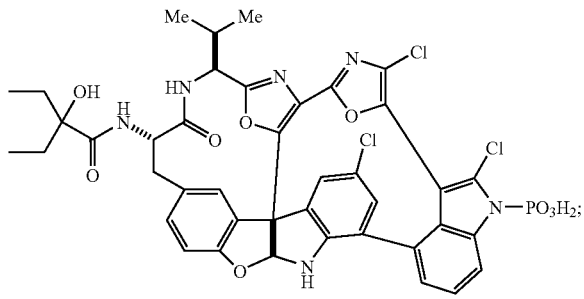

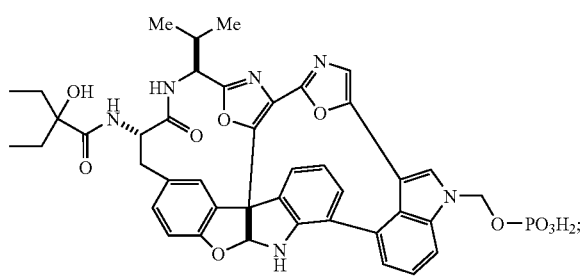

or a pharmaceutically acceptable salt, ester or conjugate thereof.

47. A compound having the structure:

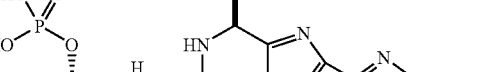

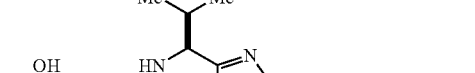

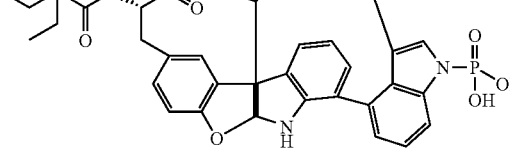

or a pharmaceutically acceptable salt, ester or conjugate thereof.

48. The compound of any one of embodiments 1 to 47 in the form of a pharmaceutically acceptable salt.

49. The compound of any one of embodiments 1 to 47 in the form of a pharmaceutically acceptable ester.

50. The conjugate of any one of embodiments 1 to 47, wherein the compound of is coupled to a targeting agent.

51. The compound of any one of embodiments 1 to 50, having aqueous solubility of greater than 1 mg/mL; or greater than 2.5 mg/mL; or greater than 5 mg/mL.

52. The compound of any one of embodiments 1 to 51, having aqueous solubility of greater than 5 mg/mL.

53. A pharmaceutical composition comprising a compound of any one of embodiments 1 to 52 and at least one pharmaceutically acceptable excipient.

54. A method of treating a cell proliferative disorder, comprising administering to a subject in need thereof a therapeutically effective amount of a compound of any one of embodiments 1 to 53 or salt, ester, conjugate or pharmaceutical composition thereof.

55. The method of embodiment 54, wherein the subject is human.

56. The method of embodiment 54 or 55, wherein the cell proliferative disorder is cancer.

57. The method of embodiment 54 to 56, wherein the cell proliferative disorder is cancer selected from breast cancer, ovarian cancer, lung cancer, colon cancer, rectal cancer, prostate cancer, pancreatic cancer, melanoma or glioma.

58. The method of any one of embodiments 54 to 57, wherein the cell proliferative disorder is breast cancer.

59. The method of embodiment 58, wherein the breast cancer is resistant to paclitaxel.

60. A method to reduce cell proliferation in a system, comprising administering to said system an effective amount of a compound of any one of embodiments 1 to 53 or salt, ester, conjugate or pharmaceutical composition thereof.

61. The method of embodiment 60, wherein the system is a tissue or a cell.

The invention claimed is:
1. A compound of Formula I:

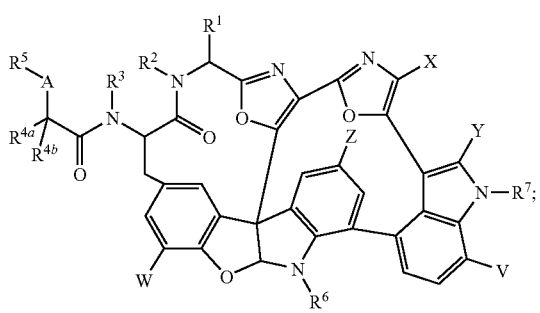

or a pharmaceutically acceptable salt thereof;
wherein $R^1$ is H, or C1-C8 alkyl, C2-C8 alkenyl, C6-C12 aryl, or C7-C20 arylalkyl;
$R^2$ is H or C1-C4 alkyl;
$R^3$ is H or C1-C4 alkyl;
each of $R^{4a}$ and $R^{4b}$ is independently H, or C1-C8 alkyl, C2-C8 alkenyl, C2-C8 alkynyl, C6-C12 aryl, or C7-C20 arylalkyl; or
$R^{4a}$ and $R^{4b}$ may be taken together with the carbon to which they are attached to form a C3-C8 cycloalkyl;
$R^6$ is H, or C1-C8 alkyl, C6-C14 arylalkyl, optionally fluorinated C1-C6 acyl, C6-C12 aroyl, alkylsulfonyl, arylsulfonyl, trialkylsilyl, or alkoxycarbonyl;
V is H, halo, or $OR^{10}$, where $R^{10}$ is H, C1-C6 acyl, C6-C12 aroyl, alkylsulfonyl, arylsulfonyl, —$PO_3H_2$, —$SO_3H$, —$C(O)CR^8_2NH_2$, —C(O)-L-COOH, or -L-O—$PO_3H_2$;

each of $R^5$ and $R^7$ is independently H, or C1-C8 alkyl, C6-C14 arylalkyl, C1-C6 acyl, C6-C12 aroyl, alkylsulfonyl, arylsulfonyl, trialkylsilyl, or alkoxycarbonyl, or —$PO_3H_2$, —$SO_3H$, —$C(O)CR^8_2NH_2$, —C(O)-L-COOH, or -L-O—$PO_3H_2$;
each $R^8$ is independently H or C1-C8 alkyl, C2-C8 alkenyl, C2-C8 alkynyl, C6-C12 aryl, C7-C20 arylalkyl; and
L is a C1-C4 alkylene or C2-C4 alkenylene linker;
provided at least one of $R^5$, $R^7$ and $R^{10}$ is —$PO_3H_2$, —$SO_3H$, —$C(O)CR^8_2NH_2$, —C(O)-L-COOH, or -L-O—$PO_3H_2$;
A is O or NR, where R is hydrogen or C1-4 alkyl;
each of W and Z is independently H, halo, OH or C1-C4 alkoxy; and
each of X and Y is independently H, halo, C1-C8 alkyl, C2-C8 alkenyl, C2-C8 alkynyl, C6-C12 aryl, or $COOR^9$ or $CONR^9_2$, where each $R^9$ is independently H or C1-C4 alkyl.

2. The compound of claim 1, wherein $R^1$ is a C1-C4 alkyl group.

3. The compound of claim 1, wherein each of $R^{4a}$ and $R^{4b}$ is a C1-C4 alkyl.

4. The compound of claim 1, wherein each of $R^{4a}$ and $R^{4b}$ is ethyl.

5. The compound of claim 1, wherein one of $R^{4a}$ and $R^{4b}$ is H, and the other is a C1-C4 alkyl.

6. The compound of claim 1, wherein $R^{4a}$ and $R^{4b}$ are taken together with the carbon to which they are attached to form a C3-C8 cycloalkyl.

7. The compound of claim 1, wherein A is O.

8. The compound of claim 7, wherein $R^5$ is —$PO_3H_2$, or a salt form thereof.

9. The compound of claim 7, wherein $R^5$ is -L-O—$PO_3H_2$, or a salt form thereof.

10. The compound of claim 9, wherein L is methylene linker.

11. The compound of claim 1, wherein $R^7$ is —$PO_3H_2$ or a salt form thereof.

12. The compound of claim 11, wherein $R^5$ is H or acetyl.

13. The compound of claim 11, wherein $R^5$—$PO_3H_2$ or a salt form thereof.

14. The compound of claim 1, wherein $R^7$ is -L-O—$PO_3H_2$, or a salt form thereof.

15. The compound of claim 14, wherein L is methylene linker.

16. The compound of claim 1, wherein V is H.

17. The compound of claim 1, wherein V is $OR^{10}$, and $R^{10}$ is H or acetyl.

18. The compound of claim 1, wherein V is $OR^{10}$, and $R^{10}$ is —$PO_3H_2$ or a salt form thereof.

19. A compound having the formula:

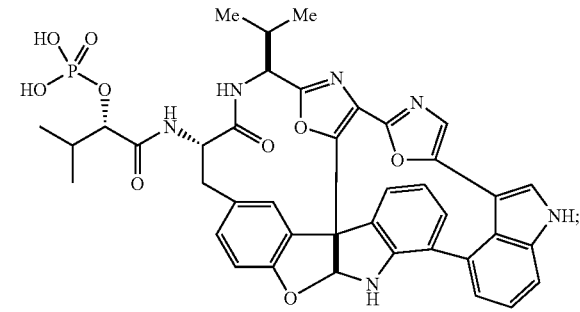

-continued

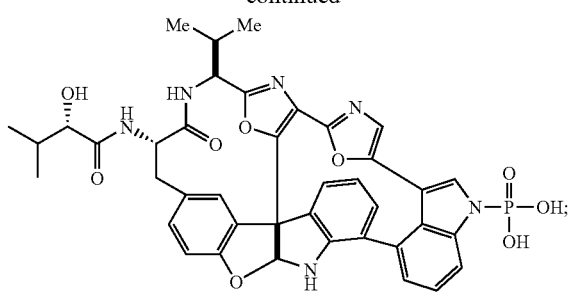

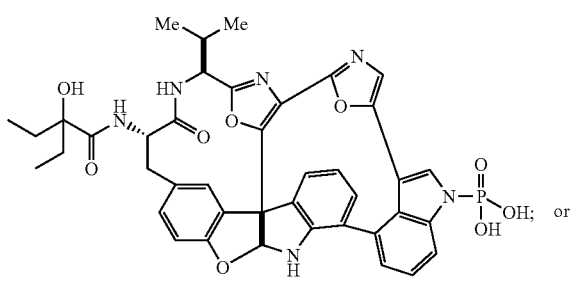

or

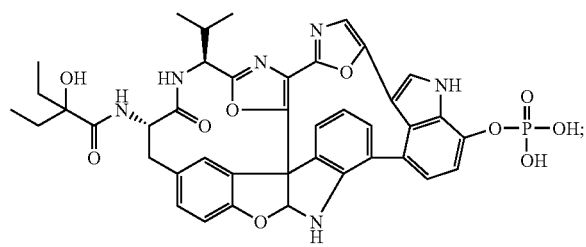

or a pharmaceutically acceptable salt thereof.

20. The compound of claim 1 in the form of a pharmaceutically acceptable salt.

21. The compound of claim 1, wherein the compound of Formula I is coupled to a targeting agent.

22. A pharmaceutical composition comprising a compound of claim 1 and at least one pharmaceutically acceptable excipient.

23. The compound of claim 1, having the Formula II,

II

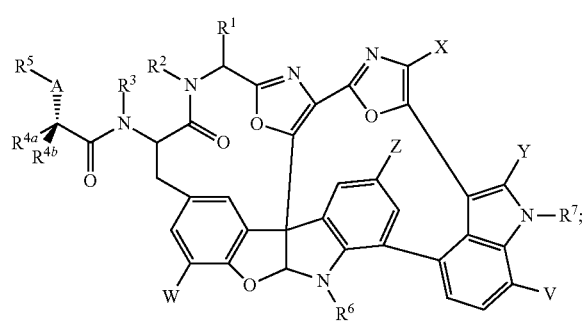

or a pharmaceutically acceptable salt thereof.

24. The compound of claim 1, having the Formula III-A,

III-A

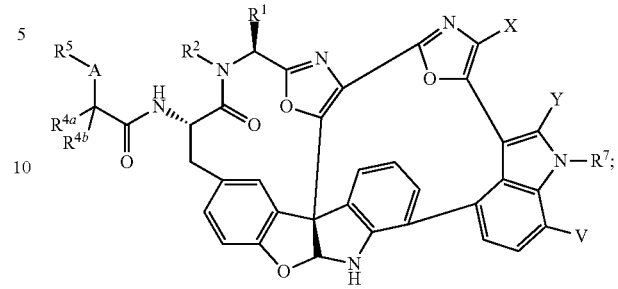

or a pharmaceutically acceptable salt thereof.

25. The compound of claim 1, having the Formula III-B,

III-B

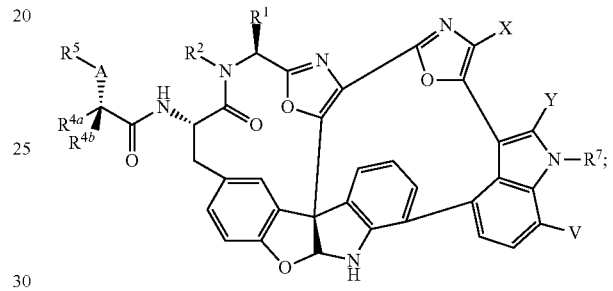

or a pharmaceutically acceptable salt thereof.

26. The compound of claim 1, having the Formula IV-A,

IV-A

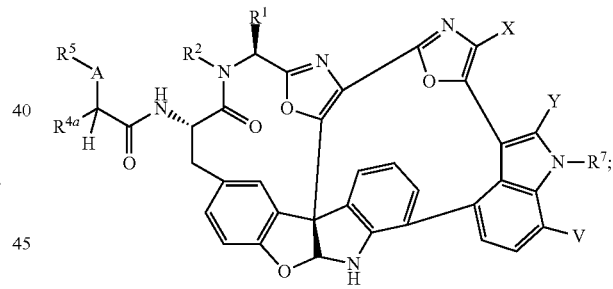

or a pharmaceutically acceptable salt thereof.

27. The compound of claim 1, having the Formula IV-B

IV-B

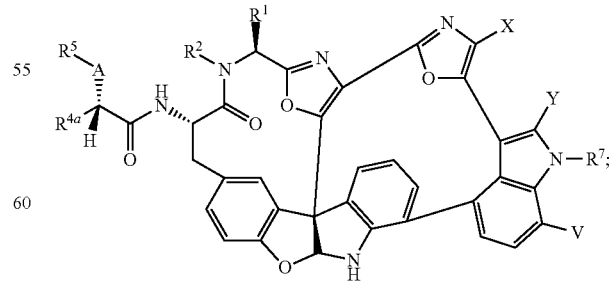

or a pharmaceutically acceptable salt thereof.

* * * * *